(12) United States Patent
Kesteleyn et al.

(10) Patent No.: US 10,913,716 B2
(45) Date of Patent: Feb. 9, 2021

(54) SUBSTITUTED INDOLINE DERIVATIVES AS DENGUE VIRAL REPLICATION INHIBITORS

(71) Applicants: Janssen Pharmaceuticals, Inc., Titusville, NJ (US); Katholieke Universiteit Leuven, Leuven (BE)

(72) Inventors: Bart Rudolf Romanie Kesteleyn, Berlare (BE); Pierre Jean-Marie Bernard Raboisson, Rosieres (BE); Jean-François Bonfanti, Ande (FR); Dorothée Alice Marie-Eve Bardiot, Heverlee (BE); Arnaud Didier M Marchand, Bierbeek (BE)

(73) Assignees: Janssen Pharmaceuticals, Inc., Titusville, NJ (US); Katholieke Universiteit Leuven, Leuven (BE)

( * ) Notice: Subject to any disclaimer, the term of this patent is extended or adjusted under 35 U.S.C. 154(b) by 283 days.

(21) Appl. No.: 16/088,459

(22) PCT Filed: Mar. 31, 2017

(86) PCT No.: PCT/EP2017/057663
§ 371 (c)(1),
(2) Date: Sep. 26, 2018

(87) PCT Pub. No.: WO2017/167953
PCT Pub. Date: Oct. 5, 2017

(65) Prior Publication Data
US 2020/0339511 A1 Oct. 29, 2020

(30) Foreign Application Priority Data
Mar. 31, 2016 (EP) .................................... 16163281

(51) Int. Cl.
| | | |
|---|---|---|
| *C07D 209/26* | (2006.01) | |
| *A61K 31/405* | (2006.01) | |
| *A61K 35/76* | (2015.01) | |
| *A61P 31/14* | (2006.01) | |
| *A61K 45/06* | (2006.01) | |

(52) U.S. Cl.
CPC .......... *C07D 209/26* (2013.01); *A61K 31/405* (2013.01); *A61K 35/76* (2013.01); *A61K 45/06* (2013.01); *A61P 31/14* (2018.01)

(58) Field of Classification Search
CPC ..... C07D 209/26; A61P 31/14; A61K 31/405; A61K 35/76; A61K 45/06
USPC ..................................................... 424/218.1
See application file for complete search history.

(56) References Cited

U.S. PATENT DOCUMENTS

| | | |
|---|---|---|
| 7,601,735 B2 | 10/2009 | Tyms et al. |
| 8,299,056 B2 | 10/2012 | Bahmanyar et al. |
| 8,524,764 B2 | 9/2013 | Canales et al. |
| 8,884,030 B2 | 11/2014 | Canales et al. |
| 8,993,604 B2 | 3/2015 | Byrd et al. |
| 9,029,376 B2 | 5/2015 | Byrd et al. |
| 9,522,923 B2 | 12/2016 | Richards et al. |
| 9,944,598 B2 | 4/2018 | Kesteleyn et al. |
| 10,029,984 B2 | 7/2018 | Kesteleyn et al. |
| 10,064,870 B2 | 9/2018 | Rajagopalan et al. |
| 10,071,961 B2 | 9/2018 | Vandyck et al. |
| 10,117,850 B2 | 11/2018 | Griffioen et al. |
| 10,206,902 B2 | 2/2019 | Kesteleyn et al. |
| 10,323,026 B2 | 6/2019 | Ikeda et al. |
| 2005/0239821 A1 | 10/2005 | Neyts et al. |
| 2006/0194835 A1 | 8/2006 | Dugourd et al. |
| 2006/0211698 A1 | 9/2006 | Botyanszki et al. |
| 2008/0318338 A1 | 12/2008 | Kamal et al. |
| 2013/0023532 A1 | 1/2013 | Casillas et al. |
| 2016/0297810 A1 | 10/2016 | Bardiot et al. |
| 2017/0002006 A1 | 1/2017 | Corte et al. |
| 2017/0096429 A1 | 4/2017 | Corte et al. |
| 2017/0281633 A1 | 10/2017 | Boylan et al. |
| 2017/0281766 A1 | 10/2017 | Wiltzius |
| 2017/0283500 A1 | 10/2017 | Wiltzius et al. |
| 2017/0298017 A1 | 10/2017 | Kesteleyn et al. |
| 2018/0256544 A1 | 9/2018 | Kesteleyn et al. |
| 2018/0256545 A1 | 9/2018 | Kesteleyn et al. |
| 2018/0346419 A1 | 12/2018 | Kesteleyn et al. |
| 2019/0104738 A1 | 4/2019 | Narine et al. |
| 2019/0112266 A1 | 4/2019 | Kesteleyn et al. |

(Continued)

FOREIGN PATENT DOCUMENTS

| | | | |
|---|---|---|---|
| JP | 2012206959 A | | 10/2012 |
| WO | 1999021559 A1 | | 5/1999 |
| WO | 02089780 A2 | | 11/2002 |

(Continued)

OTHER PUBLICATIONS

Japanese Office Action dated Jun. 2, 2020 from Japanese Patent Appln. No. JP2017-243354 (English language translation).
ACS on STN Registry No. 920950-24-9, Feb. 14, 2007.
ACS on STN Registry No. 920926-40-5, Feb. 14, 2007.
ACS on STN Registry No. 920888-80-8, Feb. 14, 2007.
ACS on STN Registry No. 920870-55-9, Feb. 14, 2007.
ACS on STN Registry No. 920827-69-6, Feb. 14, 2007.
ACS on STN Registry No. 920696-97-5, Feb. 13, 2007.

(Continued)

*Primary Examiner* — Kristin A Vajda

(57) ABSTRACT

The present invention concerns substituted indoline compounds, methods to prevent or treat dengue viral infections by using said compounds and also relates to said compounds for use as a medicine, more preferably for use as a medicine to treat or prevent dengue viral infections. The present invention furthermore relates to pharmaceutical compositions or combination preparations of the compounds, to the compositions or preparations for use as a medicine, more preferably for the prevention or treatment of dengue viral infections. The invention also relates to processes for preparation of the compounds.

16 Claims, No Drawings
Specification includes a Sequence Listing.

(56) References Cited

U.S. PATENT DOCUMENTS

2019/0183931 A1 6/2019 Bakker et al.

FOREIGN PATENT DOCUMENTS

| WO | 03050295 A2 | 6/2003 |
|---|---|---|
| WO | 2009149054 A1 | 12/2009 |
| WO | WO 2010/021878 A1 | 2/2010 |
| WO | 2010027500 A1 | 3/2010 |
| WO | 2010091413 A1 | 8/2010 |
| WO | 2011037643 A2 | 3/2011 |
| WO | 2011088303 A1 | 7/2011 |
| WO | 2011120025 A1 | 9/2011 |
| WO | WO 2013/045516 A1 | 4/2013 |
| WO | 2016050841 A1 | 4/2016 |
| WO | 2016053455 A1 | 4/2016 |
| WO | 2017079216 A1 | 5/2017 |
| WO | 2017167832 A1 | 10/2017 |
| WO | 2017167950 A1 | 10/2017 |
| WO | 2017167952 A1 | 10/2017 |
| WO | 2017167953 A1 | 10/2017 |
| WO | 2017171100 A1 | 10/2017 |
| WO | 2017173206 A1 | 10/2017 |
| WO | 2017173256 A1 | 10/2017 |
| WO | 2017173384 A1 | 10/2017 |
| WO | 2017173410 A1 | 10/2017 |
| WO | 2018178238 A1 | 10/2018 |
| WO | 2018178240 A1 | 10/2018 |
| WO | 2018215315 A1 | 11/2018 |
| WO | 2018215316 A1 | 11/2018 |

OTHER PUBLICATIONS

ACS on STN Registry No. 931079-09-3, Apr. 20, 2007.
ACS on STN Registry No. 931007-71-5, Apr. 19, 2007.
ACS on STN Registry No. 930910-25-1, Apr. 19, 2007.
ACS on STN Registry No. 930724-99-5, Apr. 18, 2007.
ACS on STN Registry No. 930463-83-5, Apr. 17, 2007.
ACS on STN Registry No. 925399-60-6, Mar. 7, 2007.
ACS on STN Registry No. 920694-81-1, Feb. 13, 2007.
ACS on STN Registry No. 920668-38-8, Feb. 13, 2007.
ACS on STN Registry No. 879164-92-8, Apr. 4, 2006.
ACS on STN Registry No. 878462-38-5, Mar. 29, 2006.
ACS on STN Registry No. 853320-15-7, Jun. 30, 2005.
Prasad L. Polavarapu, et al., Intrinsic Rotation and Molecular Structure, Chirality 15: S143-S149 (2003).
Ian Stansfield et al., Development of carboxylic acid replacements in indole-N-acetamide inhibitors of hepatitis C virus NS5B polymerase, Bioorganic & Medicinal Chemistry Letters 17 (2007) 5143-5149, ScienceDirect (2007), www.sciencedirect.com, internet.
Boltromeyuk V.V., Obshchaya khimiya (General Chemistry), Minsk, Vysheyshaya shkola, 2012, p. 65) (translation).
Banker, et al., (1996) Modern Pharmaceuticals, 3rd Edition, Revised and Expanded, p. 596.
Wolff et al., Burger's Medicinal Chemistry and Drug Discovery, 5th Ed. part 1, p. 975-977 (1995).
Prevention, Dengue, Centers for Disease Control and Prevention (Sep. 27, 2012) https://www.cdc.govidengue/prevention/index.html, internet.
Lidia Moreira Lima et al., Bioisosterism: A Useful Strategy for Molecular Modification and Drug Design, Current Medicinal Chemistry, Bentham Science Publishers Ltd. (2005) 12, pp. 23-49.
N.C.B.I.: "qHTS for inhibitors of binding or entry into cells for Marburg Virus," Pubchem Bioassay Record AID 540276, Jul. 2011, 13 pages, XP55641386, Retrieved from the Internet: https://pubchem.ncbi.nlm.nih.gov/bioassay/540276.
EP Search Report dated Nov. 19, 2019 from European Patent Appln. No. EP 19183201.3.
"Solvation," Wikipedia, at internet address: https://en.wikipedia.org/wiki/Solvation, web page last edited on Mar. 13, 2019, 6 pages.
Examination Report dated Jan. 7, 2020 from Indian Patent Appln. No. 201727014547.

SEQUENCE LISTING

<160> NUMBER OF SEQ ID NOS: 6

<210> SEQ ID NO 1
<211> LENGTH: 19
<212> TYPE: DNA
<213> ORGANISM: Dengue virus

<400> SEQUENCE: 1
cggttagagg agacccctc                                                19

<210> SEQ ID NO 2
<211> LENGTH: 21
<212> TYPE: DNA
<213> ORGANISM: Dengue virus

<400> SEQUENCE: 2
gagacagcag gatctctggt c                                             21

<210> SEQ ID NO 3
<211> LENGTH: 28
<212> TYPE: DNA
<213> ORGANISM: Dengue virus

<400> SEQUENCE: 3
aaggactaga ggttagagga gaccccc                                       28

<210> SEQ ID NO 4
<211> LENGTH: 18
<212> TYPE: DNA
<213> ORGANISM: Dengue virus

<400> SEQUENCE: 4
ggccaggtca tcaccatt                                                 18

<210> SEQ ID NO 5
<211> LENGTH: 21
<212> TYPE: DNA
<213> ORGANISM: Dengue virus

<400> SEQUENCE: 5
atgtccacgt cacacttcat g                                             21

<210> SEQ ID NO 6
<211> LENGTH: 21
<212> TYPE: DNA
<213> ORGANISM: Dengue virus

<400> SEQUENCE: 6
ttccgctgcc ctgaggctct c                                             21

SUBSTITUTED INDOLINE DERIVATIVES AS DENGUE VIRAL REPLICATION INHIBITORS

This application is a national stage application of PCT/EP2017/057663, filed Mar. 31, 2017, which claims priority benefit of Application No. EP16163281.5 filed Mar. 31, 2016. The complete disclosures of the aforementioned related patent applications are hereby incorporated herein by reference for all purposes.

The present invention relates to substituted indoline derivatives, methods to prevent or treat dengue viral infections by using said compounds and also relates to said compounds for use as a medicine, more preferably for use as a medicine to treat or prevent dengue viral infections. The present invention furthermore relates to pharmaceutical compositions or combination preparations of the compounds, to the compositions or preparations for use as a medicine, more preferably for the prevention or treatment of dengue viral infections. The invention also relates to processes for preparation of the compounds.

BACKGROUND OF THE INVENTION

Flaviviruses, which are transmitted by mosquitoes or ticks, cause life-threatening infections in man, such as encephalitis and hemorrhagic fever. Four distinct, but closely related serotypes of the flavivirus dengue are known, so-called DENV-1, -2, -3, and -4. Dengue is endemic in most tropical and sub-tropical regions around the world, predominantly in urban and semi-urban areas. According to the World Health Organization (WHO), 2.5 billion people of which 1 billion children are at risk of DENV infection (WHO, 2002). An estimated 50 to 100 million cases of dengue fever [DF], half a million cases of severe dengue disease (i.e. dengue hemorrhagic fever [DHF] and dengue shock syndrome [DSS]), and more than 20,000 deaths occur worldwide each year. DHF has become a leading cause of hospitalization and death amongst children in endemic regions. Altogether, dengue represents the most common cause of arboviral disease. Because of recent large outbreaks in countries situated in Latin America, South-East Asia and the Western Pacific (including Brazil, Puerto Rico, Venezuela, Cambodia, Indonesia, Vietnam, Thailand), numbers of dengue cases have risen dramatically over the past years. Not only is the number of dengue cases increasing as the disease is spreading to new areas, but the outbreaks tend to be more severe.

Although progress is being made in the development of vaccines against dengue with the availability of the Dengvaxia® vaccine, many difficulties are encountered. These include the existence of a phenomenon referred to as antibody-dependent enhancement (ADE). Recovery from an infection by one serotype provides lifelong immunity against that serotype but confers only partial and transient protection against a subsequent infection by one of the other three serotypes. Following infection with another serotype, pre-existing heterologous antibodies form complexes with the newly infecting dengue virus serotype but do not neutralize the pathogen. Instead, virus entry into cells is believed to be facilitated, resulting in uncontrolled virus replication and higher peak viral titers. In both primary and secondary infections, higher viral titers are associated with more severe dengue disease. Since maternal antibodies can easily pass on to infants by breast feeding, this might be one of the reasons that children are more affected by severe dengue disease than adults.

In locations with two or more serotypes circulating simultaneously, also referred to as hyper endemic regions, the risk of serious dengue disease is significantly higher due to an increased risk of experiencing a secondary, more severe infection. Moreover, in a situation of hyper-endemicity, the probability of the emergence of more virulent strains is increased, which in turn augments the probability of dengue hemorrhagic fever (DHF) or dengue shock syndrome.

The mosquitoes that carry dengue, including *Aedes aegypti* and *Aedes albopictus* (tiger mosquito), are moving north on the globe. According to the United States (US) Centers for Disease Control and Prevention (CDC), both mosquitoes are currently omnipresent in southern Texas. The spread north of dengue-carrying mosquitoes is not confined to the US, but has also been observed in Europe.

Dengvaxia©, the dengue vaccine produced by Sanofi Pasteur was first approved in Mexico and has received in the meantime approval in more countries. Nevertheless, the vaccine leaves considerable room for improvement due to limited efficacy, especially against DENV-1 and -2, low efficacy in flavivirus-naïve subjects and the lengthy dosing schedule.

Despite these shortcomings, the vaccine is a game changer in endemic settings as it will offer protection to a large part of the population, but likely not to very young infants, who bear the largest burden of dengue. In addition, the dosing schedule and very limited efficacy in flavivirus-naïve subjects make it unsuitable and likely not worthwhile/cost-effective for travelers from non-endemic areas to dengue-endemic areas. The above mentioned shortcomings of the dengue vaccines are the reason why there is a need for a pre-exposure prophylactic dengue antiviral.

Furthermore, today, specific antiviral drugs for the treatment or prevention of dengue fever virus infection are not available. Clearly, there is still a great unmet medical need for therapeutics for the prevention or treatment of viral infections in animals, more in particular in humans and especially for viral infections caused by Flaviviruses, more in particular Dengue virus. Compounds with good anti-viral potency, no or low levels of side-effects, a broad spectrum activity against multiple Dengue virus serotypes, a low toxicity and/or good pharmacokinetic or -dynamic properties are highly needed.

WO-2010/021878 discloses 2-phenylpyrrolidine and indoline derivatives as cold menthol receptor antagonists for treatment of inflammatory and central diseases.

WO-2013/045516 discloses indole or indoline derivatives for use in the treatment of dengue viral infections.

The present invention now provides compounds, substituted indoline derivatives, which show high potent activity against all four (4) serotypes of the Dengue virus.

SUMMARY OF THE INVENTION

The present invention is based on the unexpected finding that at least one of the above-mentioned problems can be solved by the current compounds of the invention.

The present invention provides compounds which have been shown to possess potent antiviral activity against all four (4) serotypes currently known. The present invention furthermore demonstrates that these compounds efficiently inhibit proliferation of Dengue virus (DENV). Therefore, these compounds constitute a useful class of potent compounds that can be used in the treatment and/or prevention of viral infections in animals, mammals and humans, more specifically for the treatment and/or prevention of infections with Dengue viruses.

The present invention furthermore relates to the use of such compounds as medicines and to their use for the manufacture of medicaments for treating and/or preventing viral infections, in particular with viruses belonging to the family of the Dengue viruses in animals or mammals, more in particular in humans. The invention also relates to methods for the preparation of all such compounds and to pharmaceutical compositions comprising them in an effective amount.

The present invention also relates to a method of treatment or prevention of dengue viral infections in humans by the administration an effective amount of one or more such compounds, or a pharmaceutically acceptable salt thereof optionally in combination with one or more other medicines, like another antiviral agent, to a patient in need thereof.

One aspect of the invention is the provision of compounds having formula (I), a stereoisomeric form, a pharmaceutically acceptable salt, solvate or polymorph thereof:

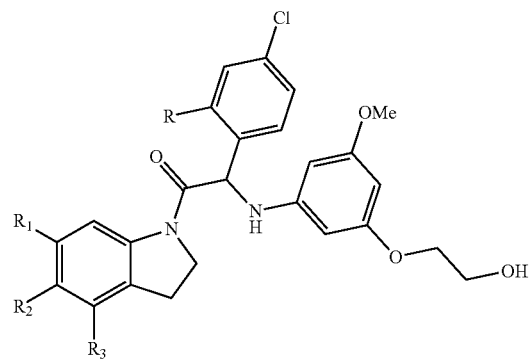

I wherein the compounds are selected from the group comprising:

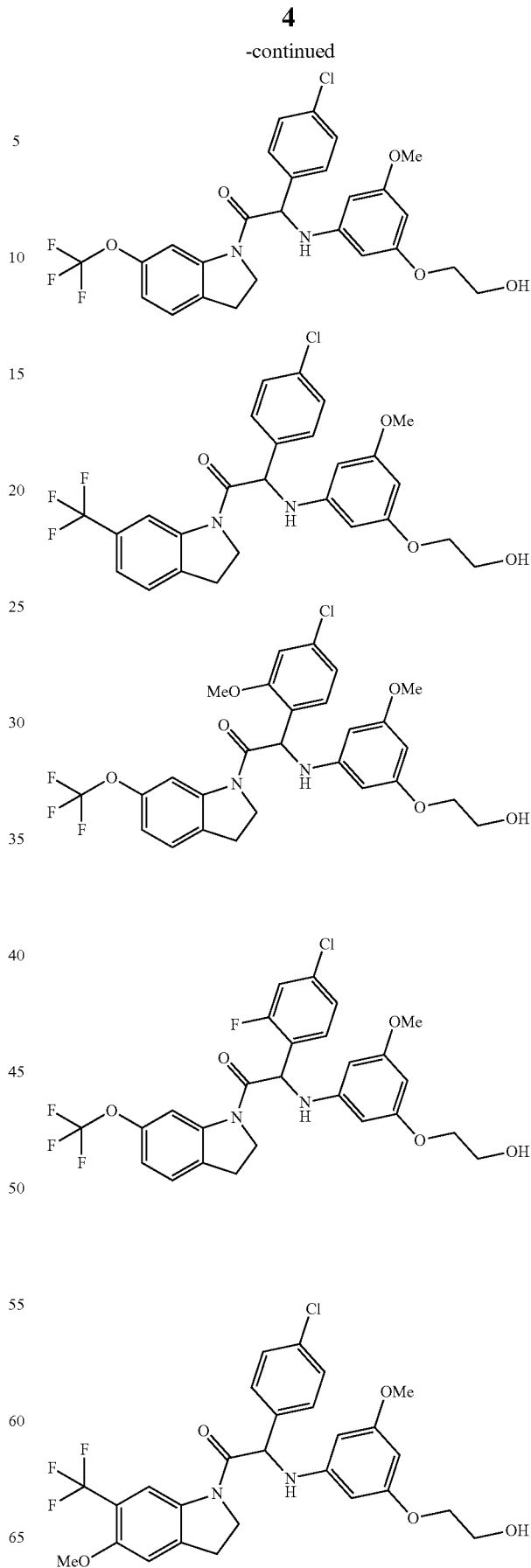

-continued

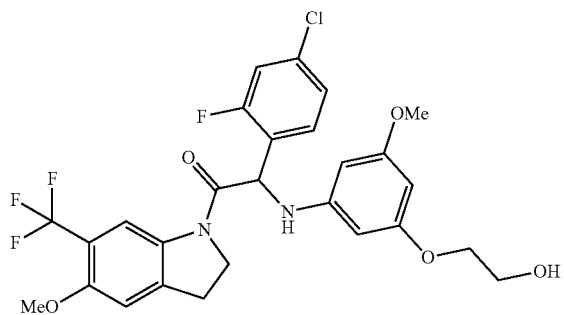
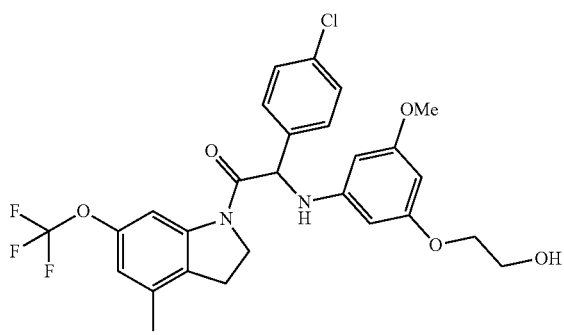
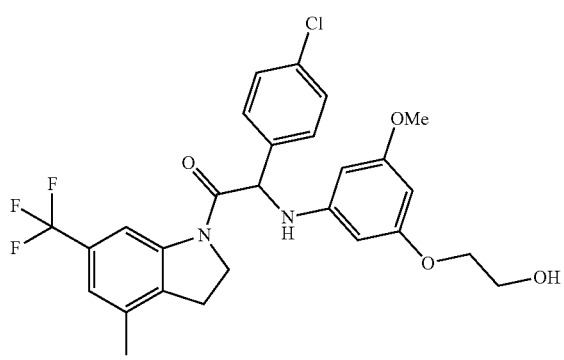
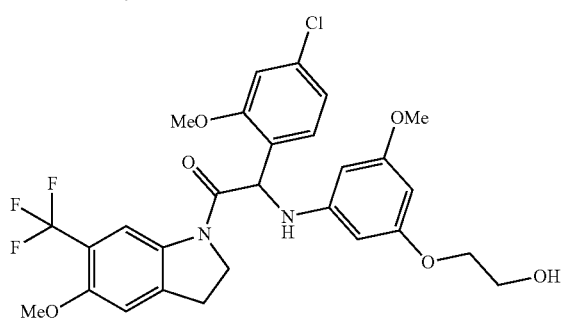
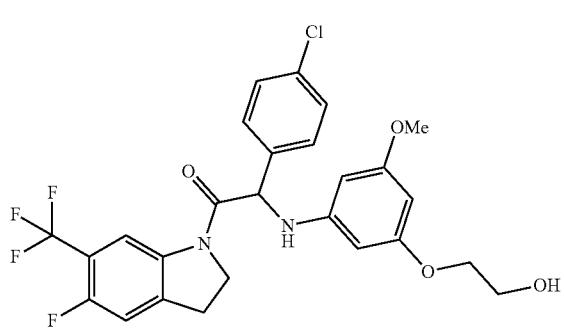

-continued

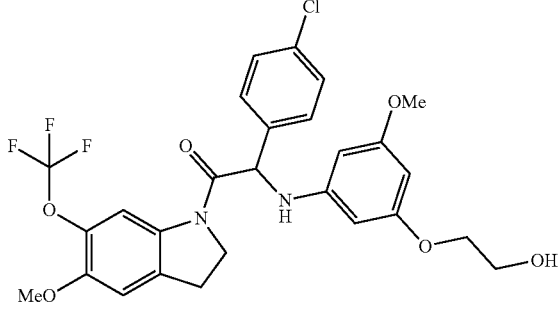

In an alternative embodiment, the present invention relates to a compound having formula (I)

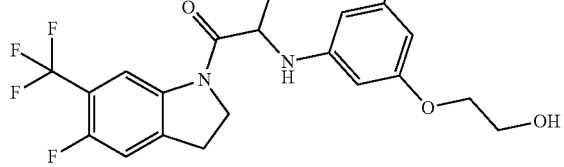

a stereoisomeric form, a pharmaceutically acceptable salt, solvate or polymorph thereof, wherein
$R_1$ is trifluoromethyl, $R_2$ is hydrogen, $R_3$ is hydrogen, and R is methoxy; or
$R_1$ is trifluoromethyl, $R_2$ is hydrogen, $R_3$ is hydrogen, and R is fluoro; or
$R_1$ is trifluoromethoxy, $R_2$ is hydrogen, $R_3$ is hydrogen, and R is hydrogen; or
$R_1$ is trifluoromethyl, $R_2$ is hydrogen, $R_3$ is hydrogen, and R is hydrogen; or
$R_1$ is trifluoromethoxy, $R_2$ is hydrogen, $R_3$ is hydrogen, and R is methoxy; or
$R_1$ is trifluoromethoxy, $R_2$ is hydrogen, $R_3$ is hydrogen, and R is fluoro; or
$R_1$ is trifluoromethyl, $R_2$ is methoxy, $R_3$ is hydrogen, and R is hydrogen; or
$R_1$ is trifluoromethyl, $R_2$ is methoxy, $R_3$ is hydrogen, and R is fluoro; or
$R_1$ is trifluoromethoxy, $R_2$ is hydrogen, $R_3$ is methyl, and R is hydrogen; or
$R_1$ is trifluoromethyl, $R_2$ is hydrogen, $R_3$ is methyl, and R is hydrogen; or
$R_1$ is trifluoromethyl, $R_2$ is methoxy, $R_3$ is hydrogen, and R is methoxy; or
$R_1$ is trifluoromethyl, $R_2$ is fluoro, $R_3$ is hydrogen, and R is hydrogen; or
$R_1$ is trifluoromethoxy, $R_2$ is methoxy, $R_3$ is hydrogen, and R is hydrogen.

Part of the current invention is also a pharmaceutical composition comprising a compound mentioned above or a stereoisomeric form, a pharmaceutically acceptable salt, solvate or polymorph thereof together with one or more pharmaceutically acceptable excipients, diluents or carriers.

Pharmaceutically acceptable salts of said compounds include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral or rectal administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of the invention used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

The present disclosure is also intended to include any isotopes of atoms present in the compounds of the invention. For example, isotopes of hydrogen include tritium and deuterium and isotopes of carbon include C-13 and C-14.

The present compounds used in the current invention may also exist in their stereochemically isomeric form, defining all possible compounds made up of the same atoms bonded by the same sequence of bonds but having different three-dimensional structures, which are not interchangeable. Unless otherwise mentioned or indicated, the chemical designation of compounds encompasses the mixture of all possible stereochemically isomeric forms, which said compounds might possess.

Said mixture may contain all diastereomers and/or enantiomers of the basic molecular structure of said compound. All stereochemically isomeric forms of the compounds used in the present invention either in pure form or in admixture with each other are intended to be embraced within the scope of the present invention including any racemic mixtures or racemates.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of compounds and intermediates used in this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The compounds of formula (I) of the present invention all have at least one chiral carbon atom as indicated in the figure below by the carbon atom labelled with

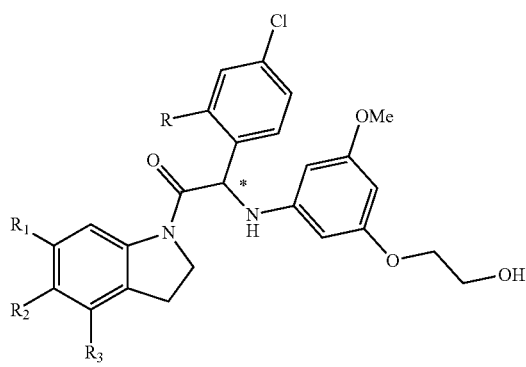

I

Due to the presence of said chiral carbon atom, a "compound of formula (I)" can be the (R)-enantiomer, the (S)-enantiomer, the racemic form, or any possible combination of the two individual enantiomers in any ratio. When the absolute (R)- or (S)-configuration of an enantiomer is not known, this enantiomer can also be identified by indicating whether the enantiomer is dextrorotatory (+)- or levorotatory (−)- after measuring the specific optical rotation of said particular enantiomer.

In an aspect the present invention relates to a first group of compound of formula (I) wherein the compounds of formula (I) have the (+) specific rotation.

In a further aspect the present invention relates to a second ground of compounds of formula (I) wherein the compounds of formula (I) have the (−) specific rotation.

EXAMPLES

LC/MS Methods

High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). For molecules with multiple isotopic patterns (Br, Cl), the reported value is the one obtained for the lowest isotope mass. All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica.

LC/MS Method codes (Flow expressed in mL/min; column temperature (T) in ° C.; Run time in minutes)

| Method code | Instrument | Column | Mobile phase | Gradient | Flow Col T | Run time (min) |
|---|---|---|---|---|---|---|
| LC-A | Waters: Acquity ® UPLC ® - DAD-Quattro Micro ™ | Waters BEH C18 (1.7 μm, 2.1 × 100 mm) | A: 95% $CH_3COONH_4$ 7 mM/5% $CH_3CN$, B: $CH_3CN$ | 84.2% A for 0.49 min, to 10.5% A in 2.18 min, held for 1.94 min, back to 84.2% A in 0.73 min, held for 0.73 min. | 0.343 mL/min / 40° C. | 6.2 |
| LC-B | Waters: Acquity ® H Clsss - DAD and SQD2TM | Waters BEH C18 (1.7 μm, 2.1 × 100 mm) | A: 95% $CH_3COONH_4$ 7 mM/5% $CH_3CN$, B: $CH_3CN$ | 84.2% A/15.8% B to 10.5% A in 2.18 min, held for 1.96 min, back to 84.2% A/15.8% B in 0.73 min, held for 0.49 min. | 0.343 mL/min / 40° C. | 6.1 |

SFC/MS Methods

The SFC measurement was performed using an Analytical Supercritical fluid chromatography (SFC) system composed by a binary pump for delivering carbon dioxide ($CO_2$) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Analytical SFC/MS Methods (Flow expressed in mL/min; column temperature (T) in ° C.; Run time in minutes, Backpressure (BPR) in bars.

| Method code | column | mobile phase | gradient | Flow/ Col T | Run time/ BPR |
|---|---|---|---|---|---|
| SFC-A | Daicel Chiralcel ® OD column (5 µm, 150 × 4.6 mm) | A:CO$_2$ B: MeOH | 40% B hold 7 min | 3/35 | 7/100 |
| SFC-B | Daicel Chiralcel ® OD-3 column (3 µm, 100 × 4.6 mm) | A:CO$_2$ B: EtOH (+0.3% iPrNH$_2$) | 40% B hold 3 min | 3.5/35 | 3/103 |
| SFC-C | Daicel Chiralpak ® IA column (5 µm, 150 × 4.6 mm) | A:CO$_2$ B: EtOH (+0.3% iPrNH$_2$) | 40% B hold 7 min | 3.5/35 | 3/103 |
| SFC-D | Daicel Chiralcel ® OJ-H column (5 µm, 150 × 4.6 mm) | A:CO$_2$ B: EtOH (+0.3% iPrNH$_2$) | 40% B hold 7 min | 3/35 | 7/100 |
| SFC-E | Daicel Chiralpak ® IC-3 column (3 µm, 100 × 4.6 mm) | A:CO$_2$ B: iPrOH (+0.3% iPrNH$_2$) | 30% B hold 5 min | 3.5/35 | 3/103 |
| SFC-F | Daicel Chiralcel ® OD column (5 µm, 150 × 4.6 mm) | A:CO$_2$ B: EtOH (+0.3% iPrNH$_2$) | 30% B hold 7 min | 3/35 | 7/100 |
| SFC-G | Daicel Chiralpak ® IA column (5 µm, 150 × 4.6 mm) | A:CO$_2$ B: iPrOH (+0.3% iPrNH$_2$) | 50% B hold 7 min | 3/35 | 7/100 |
| SFC-H | Daicel Chiralpak ® IA column (5 µm, 150 × 4.6 mm) | A:CO$_2$ B: EtOH (+0.3% iPrNH$_2$) | 30% B hold 7 min | 3/35 | 7/100 |
| SFC-I | Daicel Chiralpak ® IA column (5 µm, 150 × 4.6 mm) | A:CO$_2$ B: EtOH (+0.3% iPrNH$_2$) | 50% B hold 7 min | 3.5/35 | |
| SFC-J | Daicel Chiralpak ® IC column (5 µm, 150 × 4.6 mm) | A:CO$_2$ B: EtOH (+0.3% iPrNH$_2$) | 40% B hold 7 min | 3/35 | 7/100 |

Melting Points

Values are either peak values or melt ranges, and are obtained with experimental uncertainties that are commonly associated with this analytical method.

DSC823e (Indicated as DSC)

For a number of compounds, melting points were determined with a DSC823e (Mettler-Toledo). Melting points were measured with a temperature gradient of 10° C./minute. Maximum temperature was 300° C.

Optical Rotations:

Optical rotations were measured on a Perkin-Elmer 341 polarimeter with a sodium lamp and reported as follows: [α]° (A, c g/100 ml, solvent, T° C.). $[α]_λ^T=(100α)/(l×c)$: where l is the path length in dm and c is the concentration in g/100 ml for a sample at a temperature T (° C.) and a wavelength A (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 ml).

Example 1: Synthesis of 2-(4-chloro-2-methoxyphenyl)-2-((3-(2-hydroxyethoxy)-5-methoxyphenyl)amino)-1-(6-(trifluoromethyl)indolin-1-yl)ethanone (Compound 1) and Chiral Separation into Enantiomers 1A and 1B

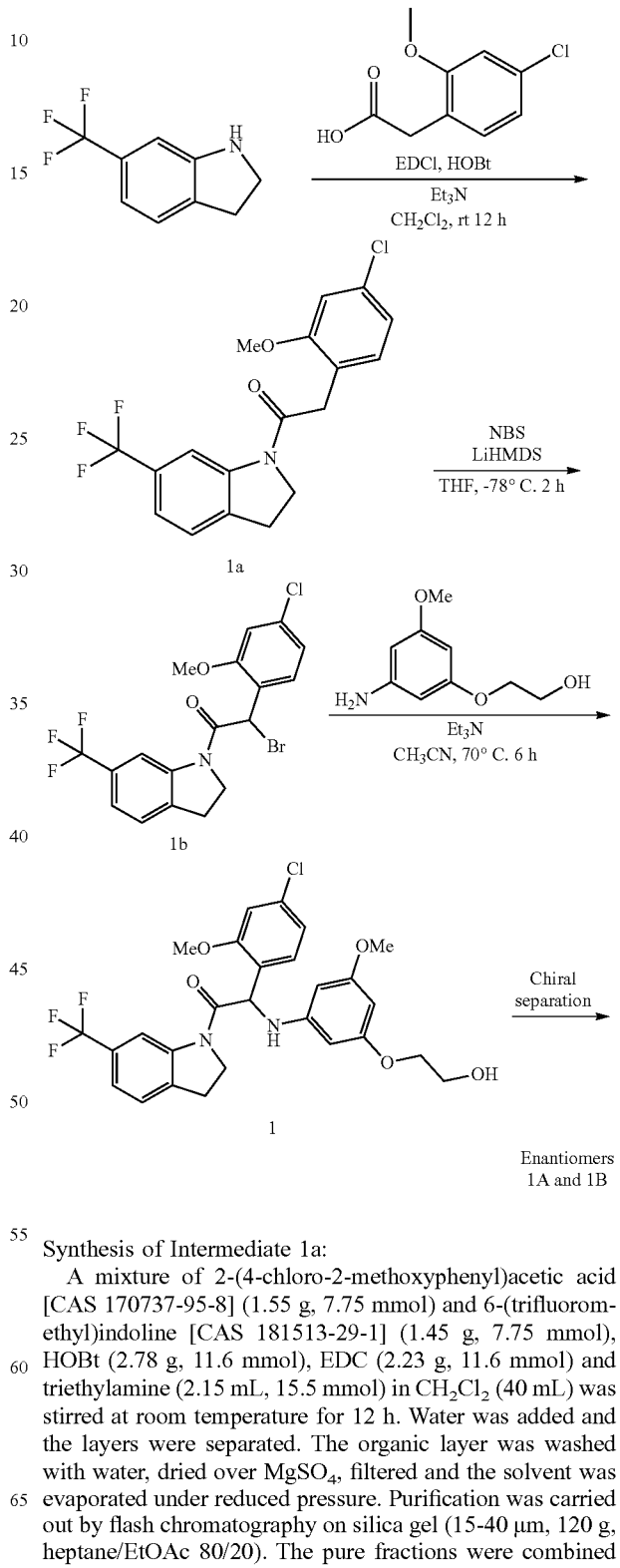

Enantiomers 1A and 1B

Synthesis of Intermediate 1a:

A mixture of 2-(4-chloro-2-methoxyphenyl)acetic acid [CAS 170737-95-8] (1.55 g, 7.75 mmol) and 6-(trifluoromethyl)indoline [CAS 181513-29-1] (1.45 g, 7.75 mmol), HOBt (2.78 g, 11.6 mmol), EDC (2.23 g, 11.6 mmol) and triethylamine (2.15 mL, 15.5 mmol) in CH$_2$Cl$_2$ (40 mL) was stirred at room temperature for 12 h. Water was added and the layers were separated. The organic layer was washed with water, dried over MgSO$_4$, filtered and the solvent was evaporated under reduced pressure. Purification was carried out by flash chromatography on silica gel (15-40 µm, 120 g, heptane/EtOAc 80/20). The pure fractions were combined and evaporated to dryness to give 2-(4-chloro-2-methoxyphenyl)-1-(6-(trifluoromethyl)-indolin-1-yl)ethanone 1a (1.66 g).

Synthesis of Intermediate 1b:

At −78° C., under a N₂ flow, LiHMDS 1M in THF (8.98 mL, 8.98 mmol) was added dropwise to a mixture of 2-(4-chloro-2-methoxyphenyl)-1-(6-(trifluoromethyl)-indolin-1-yl)ethanone 1a (1.66 g, 4.49 mmol) in THF (18 mL). The mixture was stirred for 15 min at −78° C. and a solution of NBS (879 mg, 4.94 mmol) in THF (7 mL) was added dropwise. After stirring for 2 h at −78° C., the reaction was quenched by the addition of a saturated aqueous solution of NH₄Cl. The mixture was extracted with EtOAc, dried over MgSO₄, filtered, and the solvent was evaporated under reduced pressure. Purification was carried out by flash chromatography on silica gel (15-40 μm, 40 g, heptane/EtOAc 80/20). The pure fractions were combined and evaporated to dryness to give 2-bromo-2-(4-chloro-2-methoxyphenyl)-1-(6-(trifluoromethyl)indolin-1-yl)ethanone 1b (1.23 g).

Synthesis of Compound 1 and Chiral Separation into Enantiomers 1A and 1B:

A mixture of 2-bromo-2-(4-chloro-2-methoxyphenyl)-1-(6-(trifluoromethyl)indolin-1-yl)ethanone 1b (1.2 g, 2.68 mmol), 2-(3-amino-5-methoxyphenoxy)ethanol [CAS 725237-16-1] (735 mg, 4.01 mmol) and triethylamine (558 μL, 4.01 mmol) in CH₃CN (50 mL) was stirred at 70° C. for 6 h. The mixture was concentrated under reduced pressure, diluted with EtOAc and washed with 1N HCl. The organic phase was separated, dried over MgSO₄, filtered, and the solvent was evaporated under reduced pressure. The residue was purified by flash chromatography on silica gel (15-40 μm, 40 g, CH₂Cl₂/MeOH 97.5/2.5). The pure fractions were combined and evaporated to dryness to give racemic 2-(4-chloro-2-methoxyphenyl)-2-((3-(2-hydroxyethoxy)-5-methoxyphenyl)amino)-1-(6-(trifluoromethyl)indolin-1-yl)-ethanone (Compound 1, 900 mg) after crystallization from CH₃CN. This batch was combined with 2 other batches (total amount: 1.84 g). The enantiomers were separated via Preparative Chiral SFC (Stationary phase: Chiralcel® OD-H 5 μm 250×30 mm, Mobile phase: 55% CO₂, 45% MeOH). The first eluted enantiomer was further purified by flash chromatography on silica gel (15-40 μm, 40 g, CH₂Cl₂/MeOH 99.5/0.5). The pure fractions were combined and evaporated to dryness to give, after solidification in petroleum ether/CH₃CN/diisopropyl ether, Enantiomer 1A (540 mg). The second eluted enantiomer was further purified by flash chromatography on silica gel (15-40 μm, 40 g, CH₂Cl₂/MeOH 99.5/0.5). The pure fractions were combined and evaporated to dryness to give, after solidification in petroleum ether/CH₃CN/diisopropyl ether, Enantiomer 1B (560 mg).

Compound 1:

¹H NMR (500 MHz, DMSO-d₆) δ ppm 3.24 (m, 2H) 3.59-3.67 (m, 5H) 3.78-3.87 (m, 2H) 3.90 (s, 3H) 3.98-4.07 (m, 1H) 4.33-4.42 (m, 1H) 4.79 (br t, J=4.7 Hz, 1H) 5.60 (d, J=8.5 Hz, 1H) 5.76 (s, 1H) 5.87 (br s, 2H) 6.44 (br d, J=8.5 Hz, 1H) 7.03 (dd, J=8.2, 1.9 Hz, 1H) 7.15 (d, J=1.6 Hz, 1H) 7.32 (d, J=8.5 Hz, 1H) 7.39 (d, J=7.9 Hz, 1H) 7.46 (d, J=7.9 Hz, 1H) 8.36 (s, 1H) LC/MS (method LC-A): $R_t$ 3.35 min, MH⁺ 551

Melting point: 194° C.

Enantiomer 1A:

¹H NMR (500 MHz, DMSO-d₆) δ ppm 3.16-3.30 (m, 2H) 3.57-3.67 (m, 5H) 3.79-3.88 (m, 2H) 3.90 (s, 3H) 4.03 (td, J=10.3, 7.1 Hz, 1H) 4.37 (td, J=10.1, 6.6 Hz, 1H) 4.79 (t, J=5.4 Hz, 1H) 5.61 (d, J=8.5 Hz, 1H) 5.77 (t, J=1.9 Hz, 1H) 5.87 (br s, 2H) 6.44 (d, J=8.8 Hz, 1H) 7.03 (dd, J=8.2, 2.2 Hz, 1H) 7.15 (d, J=1.9 Hz, 1H) 7.32 (d, J=8.2 Hz, 1H) 7.39 (d, J=7.9 Hz, 1H) 7.46 (d, J=7.6 Hz, 1H) 8.37 (s, 1H) LC/MS (method LC-A): $R_t$ 3.34 min, MH⁺ 551 $[\alpha]_D^{20}$: −26.5° (c 0.3091, DMF)

Chiral SFC (method SFC-A): $R_t$ 1.45 min, MH⁺ 551, chiral purity 100%.

Enantiomer 1B:

¹H NMR (500 MHz, DMSO-d₆) δ ppm 3.20-3.30 (m, 2H) 3.58-3.68 (m, 5H) 3.80-3.88 (m, 2H) 3.91 (s, 3H) 4.03 (td, J=10.2, 7.1 Hz, 1H) 4.38 (td, J=10.2, 6.6 Hz, 1H) 4.80 (t, J=5.5 Hz, 1H) 5.61 (d, J=8.8 Hz, 1H) 5.77 (t, J=2.0 Hz, 1H) 5.88 (br s, 2H) 6.45 (d, J=8.5 Hz, 1H) 7.04 (dd, J=8.2, 1.9 Hz, 1H) 7.15 (d, J=1.9 Hz, 1H) 7.32 (d, J=8.2 Hz, 1H) 7.39 (d, J=7.6 Hz, 1H) 7.47 (d, J=7.9 Hz, 1H) 8.37 (s, 1H) LC/MS (method LC-A): $R_t$ 3.34 min, MH⁺ 551

$[\alpha]_D^{20}$: +28.8° (c 0.2845, DMF)

Chiral SFC (method SFC-A): $R_t$ 3.64 min, MH⁺ 551, chiral purity 100%.

Example 2.1: Synthesis of 2-(4-chloro-2-fluorophenyl)-2-((3-(2-hydroxyethoxy)-5-methoxyphenyl)amino)-1-(6-(trifluoromethyl)indolin-1-yl)ethanone (Compound 2)

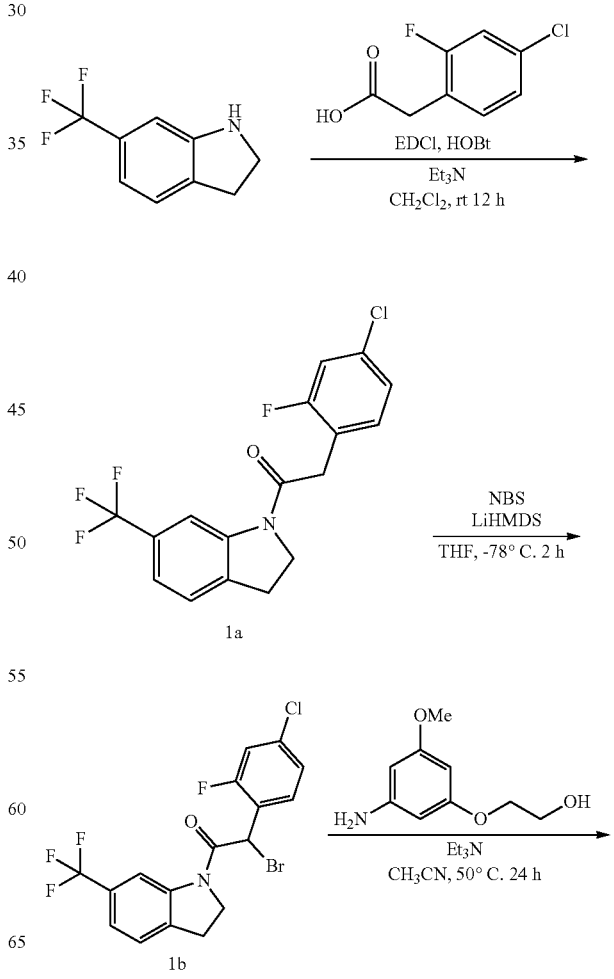

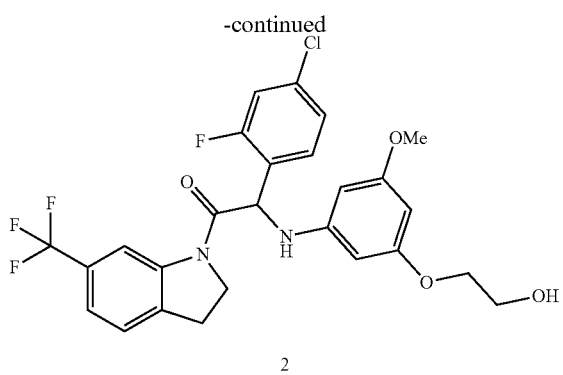

Synthesis of Intermediate 2a:

A mixture of 2-(4-chloro-2-fluorophenyl)acetic acid [CAS 194240-75-0] (504 mg, 2.67 mmol) and 6-(trifluoromethyl)indoline [CAS 181513-29-1] (500 mg, 2.67 mmol), HOBt (541 mg, 4 mmol), EDCI (768 mg, 4 mmol) and triethylamine (743 µL, 5.34 mmol) in CH$_2$Cl$_2$ (6 mL) was stirred at room temperature for 12 h. Water was added and the layers were separated. The organic layer was washed with water, dried over MgSO$_4$, filtered, and the solvent was evaporated under reduced pressure to give 2-(4-chloro-2-fluorophenyl)-1-(6-(trifluoromethyl)indolin-1-yl)ethanone 2a (1.04 g). The compound was used as such in the next step.

Synthesis of intermediate 2b:

At −78° C., under a N$_2$ flow, LiHMDS 1M in THF (5.5 mL, 5.5 mmol) was added dropwise to a solution of 2-(4-chloro-2-fluorophenyl)-1-(6-(trifluoromethyl)indolin-1-yl)ethanone 2a (980 mg, 2.74 mmol) in THF (8 mL). The reaction mixture was stirred for 15 min at −78° C. and a solution of NBS (536 mg, 3.01 mmol) in THF (5 mL) was added dropwise. After stirring for 2 h at −78° C., the reaction was quenched by the addition of a saturated aqueous solution of NH$_4$Cl. The mixture was extracted with EtOAc, dried over MgSO$_4$, filtered and the solvent was evaporated under reduced pressure to give 2-bromo-2-(4-chloro-2-fluorophenyl)-1-(6-(trifluoromethyl)indolin-1-yl)ethanone 2b (1.3 g). The compound was used as such in the next step.

Synthesis of Compound 2:

A mixture of 2-bromo-2-(4-chloro-2-fluorophenyl)-1-(6-(trifluoromethyl)indolin-1-yl)-ethanone 2b (500 mg, 1.15 mmol), 2-(3-amino-5-methoxyphenoxy)ethanol [CAS 725237-16-1] (315 mg, 1.72 mmol) and triethylamine (296 µL, 1.72 mmol) in CH$_3$CN (5 mL) was stirred at 50° C. for 24 h. The mixture was concentrated under reduced pressure, diluted with EtOAc and washed with 1N HCl. The organic phase was separated, dried over MgSO$_4$, filtered and the solvent was evaporated under reduced pressure. The residue was purified by flash chromatography on silica gel (15-40 µm, 24 g, heptane/EtOAc gradient 70/30 to 50/50). The pure fractions were combined and evaporated to dryness to give 2-(4-chloro-2-fluoro-phenyl)-2-((3-(2-hydroxyethoxy)-5-methoxyphenyl)amino)-1-(6-(trifluoromethyl)-indolin-1-yl)ethanone (Compound 2, 136 mg) after crystallization from Et$_2$O.

Compound 2:

$^1$H NMR (400 MHz, DMSO-d$_6$) δ ppm 3.20-3.28 (m, 2H) 3.57-3.69 (m, 5H) 3.79-3.91 (m, 2H) 4.03-4.13 (m, 1H) 4.39-4.49 (m, 1H) 4.78 (br s, 1H) 5.71 (d, J=9.1 Hz, 1H) 5.77-5.82 (m, 1H) 5.93 (d, J=2.0 Hz, 2H) 6.59 (d, J=9.1 Hz, 1H) 7.32 (dd, J=8.3, 1.8 Hz, 1H) 7.38-7.51 (m, 4H) 8.36 (s, 1H) LC/MS (method LC-A): R$_t$ 3.36 min, MH$^+$ 539 Melting point: 168° C.

Example 2.2: Synthesis of 2-(4-chloro-2-fluorophenyl)-2-((3-(2-hydroxyethoxy)-5-methoxyphenyl)amino)-1-(6-(trifluoromethyl)indolin-1-yl)ethanone (Compound 2) and Chiral Separation into Enantiomers 2A and 2B

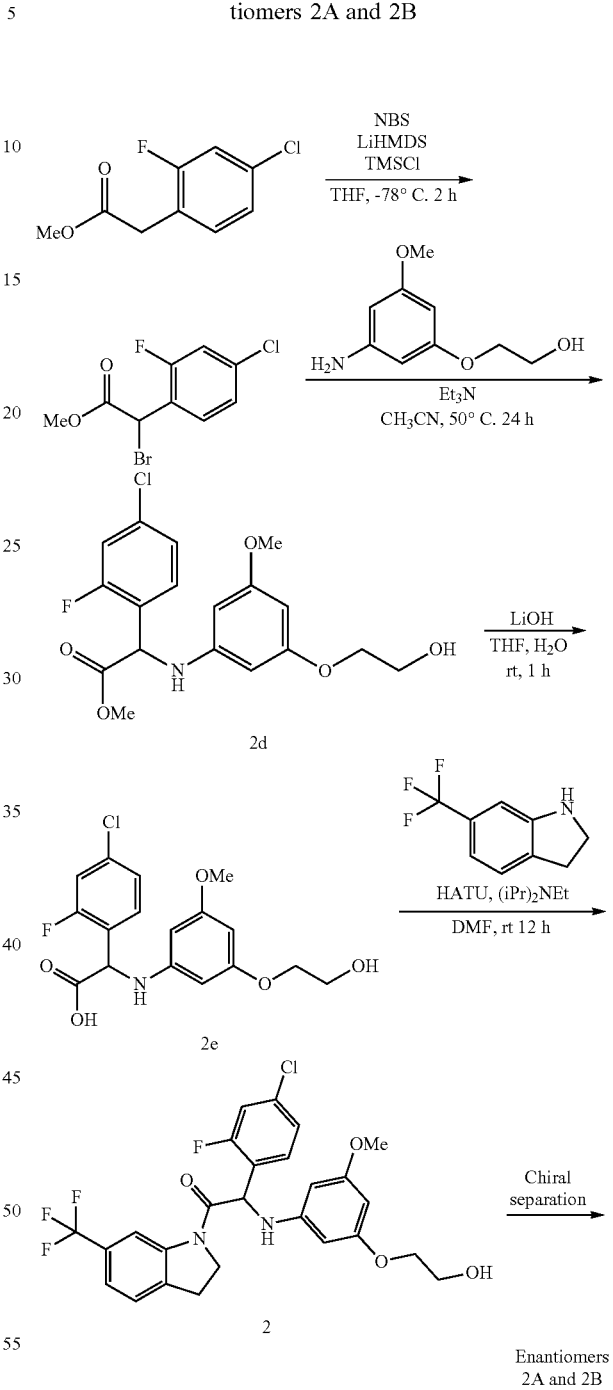

Synthesis of Intermediate 2c:

At −78° C., under a N$_2$ flow, LiHMDS 1M in THF (38.5 mL, 38.5 mmol) was added dropwise to a mixture of methyl 2-(4-chloro-2-fluorophenyl)acetate [CAS 917023-04-2] (3.9 g, 19.3 mmol) in THF (120 mL). A solution of TMSCl (3.9 mL, 30.8 mmol) in THF (30 mL) was added dropwise. The mixture was stirred for 15 min at −78° C. and a solution of NBS (3.77 g, 21.2 mmol) in THF (50 mL) was added dropwise. After stirring for 2 h at −78° C., the reaction was quenched by the addition of a saturated aqueous solution of NH₄Cl. The mixture was extracted with EtOAc, dried over MgSO₄, filtered and the solvent was evaporated under reduced pressure to give methyl 2-bromo-2-(4-chloro-2-fluorophenyl)acetate 2c (5.4 g). The compound was used as such in the next step.

Synthesis of intermediate 2d:

A mixture of methyl 2-bromo-2-(4-chloro-2-fluorophenyl)acetate 2c (4 g, 12.8 mmol), 2-(3-amino-5-methoxyphenoxy)ethanol [CAS 725237-16-1] (2.1 g, 11.6 mmol), triethylamine (2.4 mL, 17.4 mmol) in CH₃CN (80 mL) was stirred at 50° C. for 12 h. The mixture was concentrated under reduced pressure, diluted with EtOAc and washed with water. The organic phase was separated, dried over MgSO₄, filtered and the solvent was evaporated under reduced pressure. The compound was purified by flash chromatography on silica gel (15-40 μm, 80 g, CH₂Cl₂/MeOH 99.5/0.5). The pure fractions were combined and evaporated to dryness to give methyl 2-(4-chloro-2-fluorophenyl)-2-((3-(2-hydroxyethoxy)-5-methoxyphenyl)amino)acetate 2d (2.1 g).

Synthesis of intermediate 2e:

A mixture of methyl 2-(4-chloro-2-fluorophenyl)-2-((3-(2-hydroxyethoxy)-5-methoxyphenyl)amino)acetate 2d (1 g, 2.6 mmol) and LiOH (330 mg, 7.8 mmol) in THF/water (1/1) (40 mL) was stirred at room temperature for 1 h. The mixture was diluted with water. The aqueous layer was slowly acidified with 3N HCl and extracted with EtOAc. The combined organic layers were dried over MgSO₄, filtered, and the solvent was evaporated under reduced pressure to give 2-(4-chloro-2-fluorophenyl)-2-((3-(2-hydroxyethoxy)-5-methoxyphenyl)amino)acetic acid 2e (2.7 g). The compound was used as such in the next step.

Synthesis of Compound 2 and chiral separation into Enantiomers 2A and 2B:

HATU (1.85 g, 4.87 mmol) was added to a mixture of 6-(trifluoromethyl)indoline [CAS 181513-29-1] (607 mg, 3.24 mmol), 2-(4-chloro-2-fluorophenyl)-2-((3-(2-hydroxyethoxy)-5-methoxyphenyl)amino)acetic acid 2e (1.2 g, 3.24 mmol) and diisopropylethylamine (1.6 mL, 9.74 mmol) in DMF (35 mL). The resulting mixture was stirred at room temperature for 12 h. The mixture was diluted with water and the precipitate was filtered off. The solids were washed with water and taken up in EtOAc. The organic solution was washed with a 10% solution of K₂CO₃ in water and brine, dried over MgSO₄, filtered, and the solvent was evaporated under reduced pressure. The residue was purified by flash chromatography on silica gel (15-40 μm, 80 g, CH₂Cl₂/MeOH 99.5/0.5). A second purification was performed via achiral SFC (Stationary phase: 2-Ethylpyridine 5 μm 150× 30 mm, Mobile phase: 70% CO₂, 30% MeOH) to afford 2-(4-chloro-2-fluorophenyl)-2-((3-(2-hydroxyethoxy)-5-methoxyphenyl)amino)-1-(6-(trifluoromethyl)indolin-1-yl)-ethanone (Compound 2, 550 mg) as a racemic mixture. This batch was combined with another batch (total amount: 950 mg). The enantiomers were separated via Preparative Chiral SFC (Stationary phase: Chiralpak® IA 5 μm 250×20 mm, Mobile phase: 70% CO₂, 30% iPrOH (+0.3% iPrNH₂)) to give, after solidification in petroleum ether/diisopropyl ether, the first eluted Enantiomer 2A (384 mg) and the second eluted Enantiomer 2B (375 mg).

Enantiomer 2A:

¹H NMR (500 MHz, DMSO-d₆) δ ppm 3.20-3.29 (m, 2H) 3.60-3.68 (m, 5H) 3.85 (dq, J=10.6, 5.2 Hz, 2H) 4.08 (td, J=10.1, 7.3 Hz, 1H) 4.40-4.48 (m, 1H) 4.80 (t, J=5.5 Hz, 1H) 5.71 (d, J=8.8 Hz, 1H) 5.80 (t, J=2.0 Hz, 1H) 5.93 (d, J=1.9 Hz, 2H) 6.61 (d, J=8.8 Hz, 1H) 7.33 (dd, J=8.2, 1.9 Hz, 1H) 7.38-7.51 (m, 4H) 8.36 (s, 1H)

LC/MS (method LC-A): R$_t$ 3.34 min, MH⁺ 539

$[\alpha]_D^{20}$: −26.4° (c 0.2691, DMF)

Chiral SFC (method SFC-B): R$_t$ 0.83 min, MH⁺ 539, chiral purity 100%.

Enantiomer 2B:

¹H NMR (500 MHz, DMSO-d₆) δ ppm 3.21-3.29 (m, 2H) 3.60-3.68 (m, 5H) 3.85 (tq, J=10.4, 5.0 Hz, 2H) 4.04-4.12 (m, 1H) 4.40-4.48 (m, 1H) 4.80 (t, J=5.5 Hz, 1H) 5.71 (d, J=8.8 Hz, 1H) 5.78-5.81 (m, 1H) 5.93 (d, J=1.6 Hz, 2H) 6.61 (d, J=8.8 Hz, 1H) 7.33 (dd, J=8.5, 1.9 Hz, 1H) 7.39-7.52 (m, 4H) 8.36 (s, 1H)

LC/MS (method LC-A): R$_t$ 3.34 min, MH⁺ 539

$[\alpha]_D^{20}$: +27.3° (c 0.2564, DMF)

Chiral SFC (method SFC-B): R$_t$ 1.69 min. MH⁺ 539, chiral purity 99.07%.

Example 3.1: Synthesis of 2-(4-chlorophenyl)-2-((3-(2-hydroxyethoxy)-5-methoxy-phenyl)amino)-1-(6-(trifluoromethoxy)indolin-1-yl)ethanone (Compound 3) and Chiral Separation into Enantiomers 3A and 3B

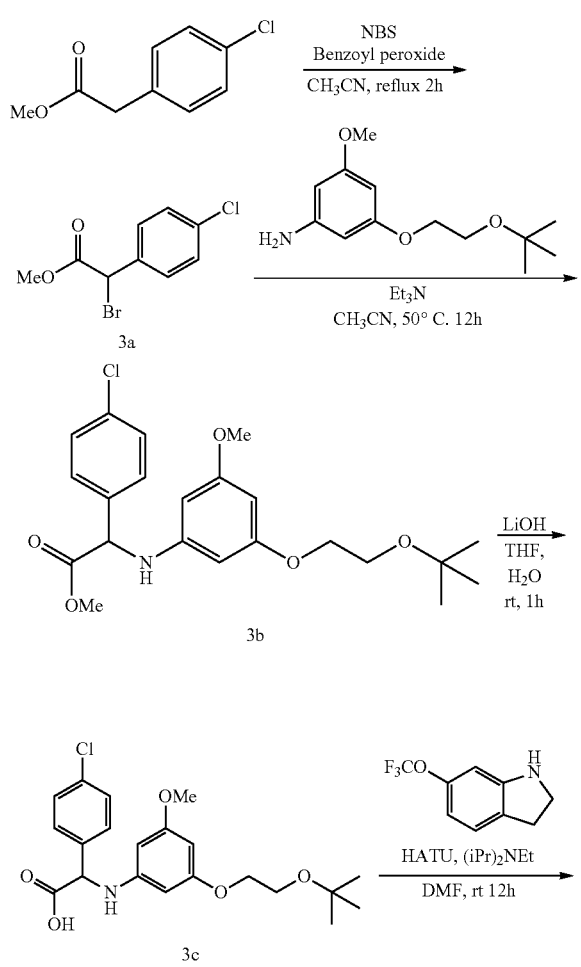

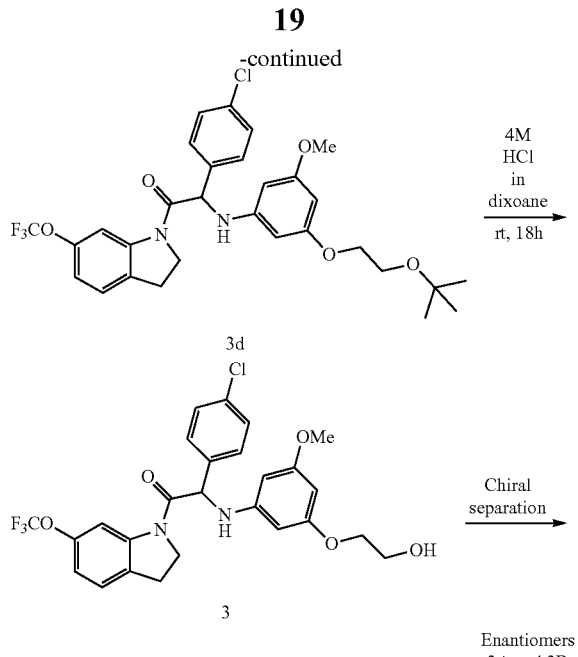

Synthesis of Intermediate 3a:

Benzoyl peroxide (5 mg) was added to a mixture of methyl 2-(4-chlorophenyl)-acetate [CAS 52449-43-1] (5.0 g, 29.7 mmol) and NBS (4.82 g, 27.1 mmol) in CH$_3$CN (80 mL). The mixture was heated under reflux for 48 h and the solvent was evaporated under reduced pressure. The mixture was taken up in cyclohexane/EtOAc 80/20 and the precipitate was filtered off and discarded (succinimide). The filtrate was concentrated under reduced pressure to give methyl 2-bromo-2-(4-chlorophenyl)acetate 3a (7.2 g). The compound was used as such in the next step.

Synthesis of Intermediate 3b:

A mixture of methyl 2-bromo-2-(4-chlorophenyl)acetate 3a (6 g, 3.80 mmol), 3-(2-(tert-butoxy)ethoxy)-5-methoxyaniline [CAS 1428973-39-0] (4.63, 4.05 mmol), triethylamine (4.04 mL, 29.0 mmol) in CH$_3$CN (30 mL) was stirred at 50° C. for 12 h. The mixture was concentrated under reduced pressure, diluted with EtOAc and washed with water. The organic phase was separated, dried over MgSO$_4$, filtered, and the solvent was evaporated under reduced pressure. The compound was purified by flash chromatography on silica gel (15-40 μm, 40 g, heptane/EtOac 90/10). The pure fractions were combined and evaporated to dryness to give methyl 2-((3-(2-(tert-butoxy)ethoxy)-5-methoxyphenyl) amino)-2-(4-chlorophenyl)-acetate 3b (4.8 g).

Synthesis of intermediate 3c:

A mixture of methyl 2-((3-(2-(tert-butoxy)ethoxy)-5-methoxyphenyl)amino)-2-(4-chlorophenyl)acetate 3b (4.8 g, 11.4 mmol) and LiOH (1.43 mg, 34.1 mmol) in THF/water (1/1) (50 mL) was stirred at room temperature for 1 h. The mixture was diluted with water. The aqueous layer was slowly acidified with 3N HCl and extracted with EtOAc. The combined organic layers were dried over MgSO$_4$, filtered, and the solvent was evaporated under reduced pressure to give 2-((3-(2-(tert-butoxy)ethoxy)-5-methoxyphenyl)amino)-2-(4-chlorophenyl)acetic acid 3c (4.6 g). The compound was used as such in the next step.

Synthesis of intermediate 3d:

HATU (2.10 g, 5.52 mmol) was added to a mixture of 6-(trifluoromethoxy)indoline [CAS 953906-76-8] (747 mg, 3.68 mmol), 2-((3-(2-(tert-butoxy)ethoxy)-5-methoxy-phenyl)amino)-2-(4-chlorophenyl)acetic acid 3c (1.5 g, 3.68 mmol) and diisopropylethylamine (1.82 mL, 11.03 mmol) in DMF (30 mL). The resulting mixture was stirred at room temperature for 12 h. The mixture was diluted with water and extracted with EtOAc. The organic layer was separated, dried over MgSO$_4$, filtered and the solvent was evaporated under reduced pressure. Purification was carried out by flash chromatography on silica gel (15-40 μm, 40 g, heptane/EtOAc 85/15). The pure fractions were combined and evaporated to dryness to give 2-((3-(2-(tert-butoxy)ethoxy)-5-methoxyphenyl)amino)-2-(4-chloro-phenyl)-1-(6-(trifluoromethoxy)indolin-1-yl)ethanone 3d (1.33 g).

Synthesis of Compound 3 chiral separation into Enantiomers 3A and 3B:

A mixture of 2-((3-(2-(tert-butoxy)ethoxy)-5-methoxyphenyl)amino)-2-(4-chloro-phenyl)-1-(6-(trifluoromethoxy)indolin-1-yl)ethanone 3d (1.33 g, 2.24 mmol) in 4M HCl in dioxane (25 mL) was stirred at room temperature for 18 h. The mixture was diluted with water and was basified with K$_2$CO$_3$. The aqueous layer was extracted with EtOAc. The organic layer was washed with water, dried over MgSO$_4$, filtered, and the solvent was evaporated under reduced pressure. Purification was carried out by flash chromatography on silica gel (15-40 μm, 40 g, CH$_2$Cl$_2$/MeOH/NH$_4$OH 99/1/0.1). The pure fractions were combined and evaporated to dryness to afford 2-(4-chlorophenyl)-2-((3-(2-hydroxyethoxy)-5-methoxyphenyl)amino)-1-(6-(trifluoromethoxy) indolin-1-yl)ethanone 3 (1 g) as a racemic mixture. The enantiomers were separated via Preparative Chiral SFC (Stationary phase: Chiralpak® IA 5 μm 250×20 mm, Mobile phase: 55% CO$_2$, 40% EtOH (+0.3% iPrNH$_2$), 5% CH$_2$Cl$_2$). The enantiomers were further separated via preparative chiral SFC (Stationary phase: Chiralcel® OD-H 5 μm 250× 30 mm, Mobile phase: 50% CO$_2$, 50% EtOH (+0.3% iPrNH$_2$)) to give, after solidification in petroleum ether/diisopropyl ether, the first eluted Enantiomer 3A (294 mg) and the second eluted Enantiomer 3B (244 mg).

Compound 3:

$^1$H NMR (500 MHz, DMSO-d$_6$) δ ppm 3.08-3.25 (m, 2H) 3.58-3.68 (m, 5H) 3.79-3.89 (m, 2H) 4.00-4.11 (m, 1H) 4.47-4.57 (m, 1H) 4.79 (t, J=5.4 Hz, 1H) 5.56 (br d, J=8.8 Hz, 1H) 5.76 (s, 1H) 5.94 (s, 2H) 6.47 (br d, J=8.5 Hz, 1H) 7.01 (br d, J=7.9 Hz, 1H) 7.34 (d, J=8.2 Hz, 1H) 7.44 (d, J=8.5 Hz, 2H) 7.55 (br d, J=8.2 Hz, 2H) 8.03 (br s, 1H)

LC/MS (method LC-A): R$_t$ 3.36 min, MH$^+$ 537

Melting point: 162° C.

Enantiomer 3A:

$^1$H NMR (500 MHz, DMSO-d$_6$) δ ppm 3.08-3.25 (m, 2H) 3.60-3.68 (m, 5H) 3.79-3.89 (m, 2H) 4.05 (td, J=10.4, 7.3 Hz, 1H) 4.52 (td, J=10.4, 6.3 Hz, 1H) 4.79 (t, J=5.5 Hz, 1H) 5.56 (d, J=8.8 Hz, 1H) 5.76 (t, J=2.0 Hz, 1H) 5.94 (d, J=1.9 Hz, 2H) 6.47 (d, J=8.5 Hz, 1H) 7.01 (dd, J=8.0, 1.7 Hz, 1H) 7.33 (d, J=8.2 Hz, 1H) 7.44 (d, J=8.5 Hz, 2H) 7.55 (d, J=8.5 Hz, 2H) 8.03 (s, 1H) LC/MS (method LC-A): R$_t$ 3.36 min, MH$^+$ 537

[α]$_D^{20}$: +51.9° (c 0.2736, DMF)

Chiral SFC (method SFC-C): R$_t$ 2.55 min, MH$^+$ 537, chiral purity 100%.

Enantiomer 3B:

$^1$H NMR (500 MHz, DMSO-d$_6$) δ ppm 3.08-3.26 (m, 2H) 3.59-3.68 (m, 5H) 3.80-3.90 (m, 2H) 4.05 (td, J=10.4, 7.3 Hz, 1H) 4.52 (td, J=10.4, 6.3 Hz, 1H) 4.79 (t, J=5.5 Hz, 1H) 5.56 (d, J=8.8 Hz, 1H) 5.76 (t, J=2.0 Hz, 1H) 5.94 (d, J=1.6 Hz, 2H) 6.47 (d, J=8.5 Hz, 1H) 7.01 (dd, J=8.2, 1.6 Hz, 1H) 7.34 (d, J=8.2 Hz, 1H) 7.44 (d, J=8.5 Hz, 2H) 7.55 (d, J=8.5 Hz, 2H) 8.03 (s, 1H)

LC/MS (method LC-A): $R_t$ 3.36 min, MH$^+$ 537
$[\alpha]_D^{20}$: −51.1° (c 0.2973, DMF)
Chiral SFC (method SFC-C): $R_t$ 3.56 min. MH$^+$ 537, chiral purity 99.58%.

Example 3.2: Synthesis of 2-(4-chlorophenyl)-2-((3-(2-hydroxyethoxy)-5-methoxy-phenyl)amino)-1-(6-(trifluoromethoxy)indolin-1-yl)ethanone (Compound 3) and Chiral Separation into Enantiomers 3A and 3B

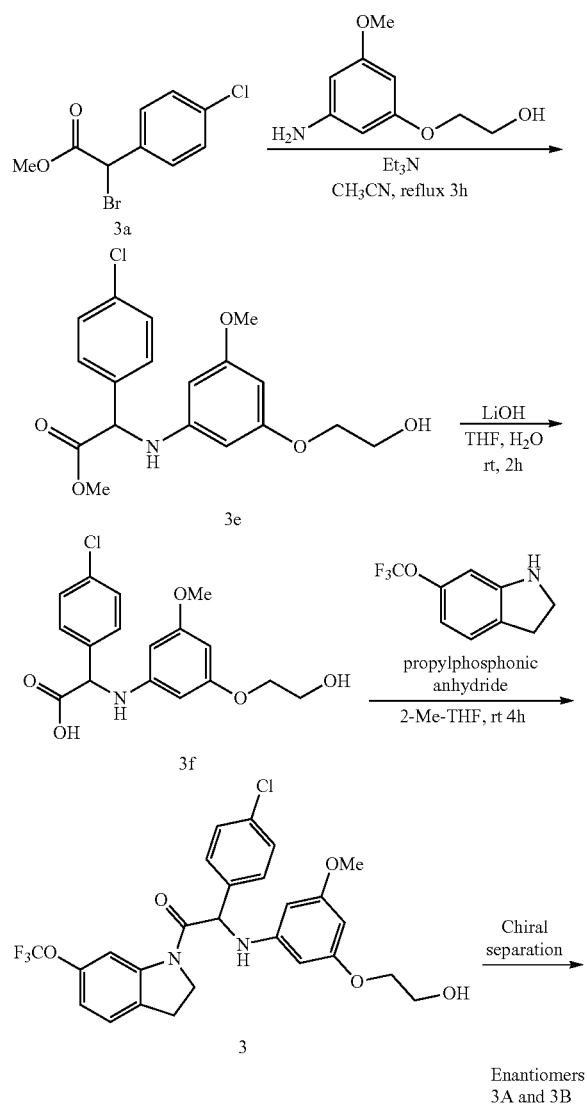

Synthesis of Intermediate 3e:

A mixture of methyl 2-bromo-2-(4-chlorophenyl)acetate 3a (19.2 g, 72.9 mmol), 2-(3-amino-5-methoxyphenoxy)ethanol [CAS 725237-16-1] (13.4 g, 72.9 mmol) and triethylamine (15.2 mL, 109.3 mmol) in CH$_3$CN (115 mL) was heated under reflux for 3 h. The mixture was concentrated under reduced pressure, diluted with EtOAc and washed with 1N HCl. The organic phase was separated, dried over MgSO$_4$, filtered, and the solvent was evaporated under reduced pressure to give crude intermediate 3e (30 g). This fraction was combined with another batch of crude intermediate 3e (total amount: 37 g) and purified by flash chromatography on silica gel (15-40 μm, 400 g, heptane/EtOAc 60/40). The pure fractions were combined and evaporated to dryness to give methyl 2-(4-chlorophenyl)-2-((3-(2-hydroxy-ethoxy)-5-methoxyphenyl)amino)acetate 3e (26 g).

Synthesis of Intermediate 3f:

A mixture of methyl 2-(4-chlorophenyl)-2-((3-(2-hydroxyethoxy)-5-methoxyphenyl)-amino)acetate 3e (10 g, 27.3 mmol) and LiOH (3.44 g, 82.0 mmol) in THF/water (1/1) (200 mL) was stirred at room temperature for 2 h. The mixture was diluted with water. The aqueous layer was slowly acidified with 3N HCl and extracted with EtOAc. The organic layers were washed with water, separated, dried over MgSO$_4$, filtered, and the solvent was evaporated under reduced pressure to give 2-(4-chlorophenyl)-2-((3-(2-hydroxyethoxy)-5-methoxyphenyl)amino)acetic acid 3f (9.5 g). The compound was used as such in the next step.

Synthesis of Compound 3 and Chiral Separation into Enantiomers 3A and 3B:

Under N$_2$ flow at 5° C., propylphosphonic anhydride (2.56 mL, 4.26 mmol) was added dropwise to a mixture of 6-(trifluoromethoxy)indoline [CAS 953906-76-8](577 mg, 2.84 mmol), 2-(4-chlorophenyl)-2-((3-(2-hydroxyethoxy)-5-methoxy-phenyl)amino)acetic acid 3f (1.3 g, 3.70 mmol) and diisopropylethylamine (1.03 mL, 6.25 mmol) in 2-Me-THF (30 mL). The mixture was stirred at room temperature for 4 h. Water was added and the mixture was extracted with EtOAc. The organic layer was washed with a 10% solution of K$_2$CO$_3$ in water and then with water, dried over MgSO$_4$, filtered, and the solvent was evaporated under reduced pressure. Purification was carried out by flash chromatography on silica gel, (15-40 μm, 40 g, CH$_2$Cl$_2$/MeOH 99/1). The pure fractions were combined and evaporated to dryness, to give 2-(4-chlorophenyl)-2-((3-(2-hydroxyethoxy)-5-methoxyphenyl)amino)-1-(6-(trifluoromethoxy)indolin-1-yl)ethanone (Compound 3, 800 mg) as a racemic mixture. This fraction was combined with another batch (total amount: 1.4 g) and crystallized from diisopropyl ether to give 1.03 g of Compound 3. The enantiomers were separated via Preparative Chiral SFC (Stationary phase: Chiralpak® IA 5 μm 250×20 mm, Mobile phase: 55% CO$_2$, 45% EtOH (+0.3% iPrNH$_2$)). The first eluted enantiomer was further purified via reverse phase chromatography (stationary phase: X-bridge-C-18 10 μm 30×150 mm, mobile phase: 0.2% NH$_4$HCO$_3$/CH$_3$CN gradient 60/40 to 0/100) to give Enantiomer 3A (312 mg). The second eluted Enantiomer 3B (436 mg) was not further purified.

Example 4: Synthesis of 2-(4-chlorophenyl)-2-((3-(2-hydroxyethoxy)-5-methoxy-phenyl)amino)-1-(6-(trifluoromethyl)indolin-1-yl)ethanone (Compound 4) and Chiral Separation into Enantiomers 4A and 4B

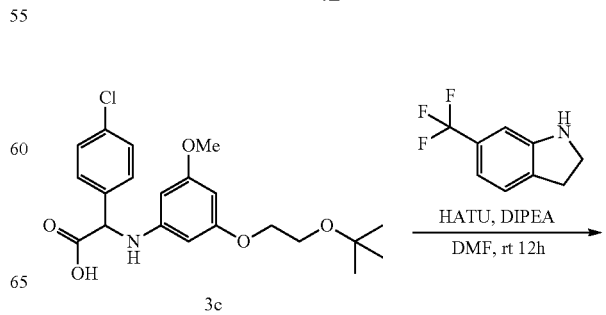

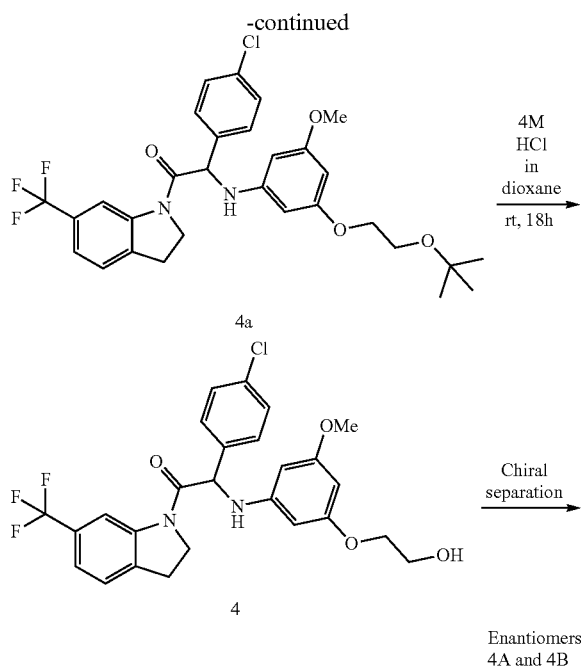

Synthesis of Intermediate 4a:

HATU (2.24 g, 5.88 mmol) was added to a mixture of 6-(trifluoromethyl)indoline [CAS 181513-29-1] (734 mg, 3.92 mmol), 2-((3-(2-(tert-butoxy)ethoxy)-5-methoxy-phenyl)amino)-2-(4-chlorophenyl)acetic acid 3c (1.6 g, 3.92 mmol) and diisopropylethylamine (1.95 mL, 11.8 mmol) in DMF (30 mL). The resulting mixture was stirred at room temperature for 12 h. The mixture was diluted with water and EtOAc. The organic layer was separated, washed with a 10% solution of $K_2CO_3$ in water, washed with brine, dried over $MgSO_4$, filtered, and the solvent was concentrated under reduced pressure. The crude residue was purified by column chromatography on silica gel (15-40 μm, 40 g, heptane/EtOAc 85/15). The pure fractions were combined and the solvent was concentrated under reduced pressure to give 2-((3-(2-(tert-butoxy)ethoxy)-5-methoxyphenyl)amino)-2-(4-chloro-phenyl)-1-(6-(trifluoromethyl)indolin-1-yl)ethanone 4a (1.38 g).

Synthesis of Compound 4 and Chiral Separation into Enantiomers 4A and 4B:

2-((3-(2-(tert-Butoxy)ethoxy)-5-methoxyphenyl)amino)-2-(4-chlorophenyl)-1-(6-(trifluoromethyl)indolin-1-yl)ethanone 4a (1.38 g, 2.39 mmol) was mixed with 4M HCl in dioxane (25 mL) stirred at room temperature for 18 h. The mixture was diluted with water and basified with $K_2CO_3$. The aqueous layer was extracted with EtOAc. The organic layer was washed with water, dried over $MgSO_4$, filtered, and the solvent was evaporated under reduced pressure. Purification was carried out by flash chromatography on silica gel (15-40 μm, 40 g, $CH_2Cl_2$/MeOH/$NH_4OH$ 99/1/0.1). The pure fractions were combined and evaporated to dryness to afford 2-(4-chlorophenyl)-2-((3-(2-hydroxyethoxy)-5-methoxyphenyl)amino)-1-(6-(trifluoromethyl)indolin-1-yl)ethanone (Compound 4, 1.08 g) as a racemic mixture. The enantiomers were separated via Preparative Chiral SFC (Stationary phase: Chiralcel® OJ-H 5 μm 250×20 mm, Mobile phase: 60% $CO_2$, 40% EtOH (+0.3% iPrNH$_2$)). The first eluted enantiomer (413 mg) was solidified in heptane/to give Enantiomer 4A (327 mg). The second eluted enantiomer (410 mg) was solidified in heptane/diisopropyl ether to give Enantiomer 4B (330 mg).

Compound 4:

$^1$H NMR (500 MHz, DMSO-d$_6$) δ ppm 3.16-3.32 (m, 2H) 3.59-3.68 (m, 5H) 3.79-3.90 (m, 2H) 4.03 (td, J=10.4, 6.9 Hz, 1H) 4.53 (td, J=10.3, 6.5 Hz, 1H) 4.79 (t, J=5.5 Hz, 1H) 5.58 (d, J=8.5 Hz, 1H) 5.76 (t, J=2.0 Hz, 1H) 5.95 (s, 2H) 6.44 (d, J=8.5 Hz, 1H) 7.37-7.41 (m, 1H) 7.43-7.49 (m, 3H) 7.56 (d, J=8.5 Hz, 2H) 8.38 (s, 1H)

LC/MS (method LC-A): R$_t$ 3.31 min. MH$^+$ 521

Melting point: 160° C.

Enantiomer 4A:

$^1$H NMR (400 MHz, DMSO-d$_6$) δ ppm 3.15-3.29 (m, 2H) 3.58-3.70 (m, 5H) 3.79-3.89 (m, 2H) 4.03 (td, J=10.4, 7.6 Hz, 1H) 4.53 (td, J=10.2, 6.3 Hz, 1H) 4.78 (br s, 1H) 5.57 (d, J=9.1 Hz, 1H) 5.74-5.80 (m, 1H) 5.95 (d, J=1.0 Hz, 2H) 6.43 (br d, J=8.6 Hz, 1H) 7.36-7.41 (m, 1H) 7.42-7.49 (m, 3H) 7.56 (d, J=8.6 Hz, 2H) 8.38 (s, 1H)

LC/MS (method LC-B): R$_t$ 3.03 min, MH$^+$ 521

[α]$_D^{20}$: +52.0° (c 0.3036, DMF)

Chiral SFC (method SFC-D): R$_t$ 1.82 min, MH$^+$ 521, chiral purity 100%.

Enantiomer 4B:

$^1$H NMR (400 MHz, DMSO-d$_6$) δ ppm 3.18-3.29 (m, 2H) 3.59-3.70 (m, 5H) 3.84 (m, 2H) 3.97-4.10 (m, 1H) 4.46-4.59 (m, 1H) 4.78 (br s, 1H) 5.57 (br d, J=8.6 Hz, 1H) 5.76 (s, 1H) 5.95 (s, 2H) 6.43 (br d, J=8.6 Hz, 1H) 7.35-7.50 (m, 4H) 7.56 (br d, J=8.6 Hz, 2H) 8.38 (s, 1H)

LC/MS method LC-B): R$_t$ 3.03 min, MH$^+$ 521

[α]$_D^{20}$: −51.8° (c 0.3418, DMF)

Chiral SFC (method SFC-D): R$_t$ 3.17 min, MH$^+$ 521, chiral purity 99.56%.

Example 5: Synthesis of 2-(4-chloro-2-methoxyphenyl)-2-((3-(2-hydroxyethoxy)-5-methoxyphenyl)amino)-1-(6-(trifluoromethoxy)indolin-1-yl)ethanone (Compound 5) and Chiral Separation into Enantiomers 5A and 5B

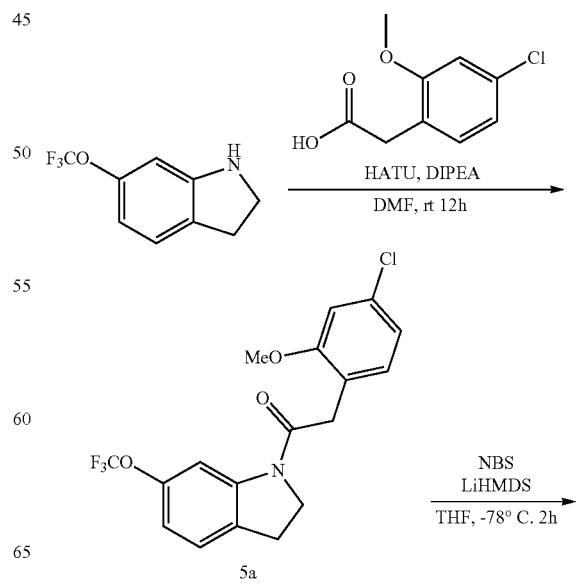

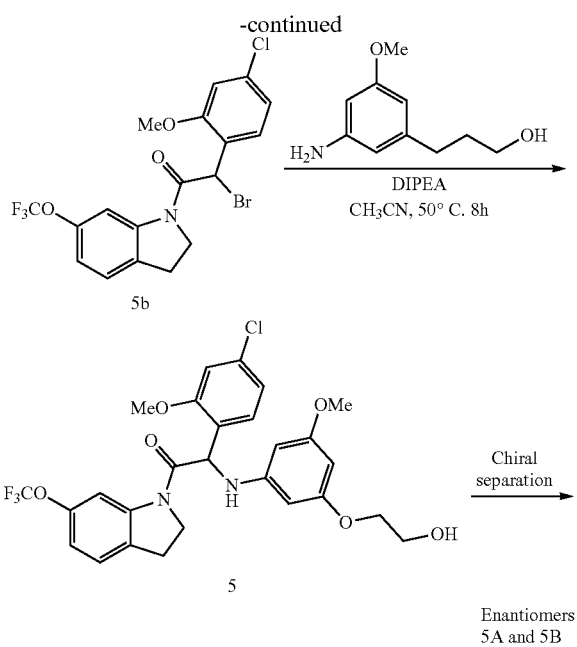

Synthesis of Intermediate 5a:

A mixture of 6-(trifluoromethoxy)indoline [CAS 953906-76-8] (1 g, 4.92 mmol), 2-(4-chloro-2-methoxyphenyl)acetic acid [CAS 170737-95-8] (1.09 g, 5.41 mmol), HATU (2.81 g, 7.38 mmol) and diisopropylethylamine (2.44 mL, 14.8 mmol) in DMF (10 mL) was stirred at room temperature for 12 h. Water and EtOAc were added and the layers were separated. The organic layer was washed with water, dried over $MgSO_4$, filtered, and the solvent was evaporated under reduced pressure. The residue was purified by chromatography on silica gel (15-40 µm, 80 g, heptane/EtOAc 85/15). The pure fractions were combined and the solvent was concentrated under reduced pressure to give, after crystallization from $CH_3CN$/heptane, 2-(4-chloro-2-methoxyphenyl)-1-(6-(trifluoromethoxy)indolin-1-yl)ethanone 5a (1.53 g).

Synthesis of Intermediate 5b:

At −78° C., under a $N_2$ flow, LiHMDS 1M in THF (7.93 mL, 7.93 mmol) was added dropwise to a mixture of 2-(4-chloro-2-methoxyphenyl)-1-(6-(trifluoromethoxy)-indolin-1-yl)ethanone 5a (1.53 g, 3.97 mmol) in THF (12 mL). The mixture was stirred for 15 min at −78° C. and a solution of NBS (776 mg, 4.36 mmol) in THF (10 mL) was added dropwise. After stirring for 2 h at −78° C., the reaction was quenched by the addition of a saturated aqueous solution of $NH_4Cl$. The mixture was extracted with EtOAc, dried over $MgSO_4$, filtered, and the solvent was evaporated under reduced pressure to give 2-bromo-2-(4-chloro-2-methoxyphenyl)-1-(6-(trifluoromethoxy)indolin-1-yl)ethanone 5b (1.70 g). The compound was used as such in the next step.

Synthesis of Compound 5 and Chiral Separation into Enantiomers 5A and 5B:

A mixture of 2-bromo-2-(4-chloro-2-methoxyphenyl)-1-(6-(trifluoromethoxy)indolin-1-yl)ethanone 5b (1.37 g, 2.95 mmol), 2-(3-amino-5-methoxyphenoxy)ethanol [CAS 725237-16-1] (810 mg, 4.42 mmol) and diisopropylethylamine (762 µL, 4.42 mmol) in $CH_3CN$ (20 mL) was stirred at 50° C. for 8 h. The mixture was concentrated under reduced pressure, diluted with EtOAc and washed with 1N HC. The organic phase was separated, dried over $MgSO_4$, filtered, and the solvent was evaporated under reduced pressure. The compound was purified by flash chromatography on silica gel (15-40 µm, 80 g, $CH_2Cl_2$/MeOH 98.5/1.5). The pure fractions were combined and evaporated to dryness to give, after crystallization from $CH_3CN$, 2-(4-chloro-2-methoxyphenyl)-2-((3-(2-hydroxyethoxy)-5-methoxyphenyl)amino)-1-(6-(trifluoromethoxy)indolin-1-yl)ethanone (Compound 5, 500 mg) as a racemic mixture. This batch was combined with another batch (total amount: 903 mg). The enantiomers were separated via Preparative Chiral SFC (Stationary phase: Chiralpak® IC 5 µm 250×30 mm, Mobile phase: 65% $CO_2$, 35% iPrOH (+0.3% iPrNH$_2$)). The first eluted enantiomer (453 mg) was solidified in petroleum ether/diisopropyl ether to give Enantiomer 5A (355 mg). The second eluted enantiomer (436 mg) was solidified in petroleum ether/diisopropyl ether to give Enantiomer 5B (342 mg).

Compound 5:
$^1$H NMR (500 MHz, DMSO-$d_6$) δ ppm 3.11-3.23 (m, 2H) 3.59-3.67 (m, 5H) 3.79-3.87 (m, 2H) 3.90 (s, 3H) 4.01-4.09 (m, 1H) 4.32-4.41 (m, 1H) 4.79 (t, J=5.5 Hz, 1H) 5.59 (d, J=8.5 Hz, 1H) 5.76 (s, 1H) 5.87 (br s, 2H) 6.46 (br d, J=8.8 Hz, 1H) 6.98-7.06 (m, 2H) 7.14 (d, J=1.6 Hz, 1H) 7.30-7.35 (m, 2H) 8.02 (s, 1H)

LC/MS (method LC-A): $R_t$ 3.38 min, MH$^+$ 567
Melting point: 162° C.

Enantiomer 5A:
$^1$H NMR (500 MHz, DMSO-$d_6$) δ ppm 3.10-3.25 (m, 2H) 3.59-3.67 (m, 5H) 3.78-3.88 (m, 2H) 3.90 (s, 3H) 4.04 (td, J=10.3, 7.1 Hz, 1H) 4.37 (td, J=10.2, 6.8 Hz, 1H) 4.79 (t, J=5.5 Hz, 1H) 5.59 (d, J=8.5 Hz, 1H) 5.76 (t, J=2.0 Hz, 1H) 5.84-5.89 (m, 2H) 6.46 (d, J=8.5 Hz, 1H) 6.99-7.05 (m, 2H) 7.14 (d, J=2.2 Hz, 1H) 7.31 (d, J=8.2 Hz, 1H) 7.34 (d, J=8.2 Hz, 1H) 8.02 (s, 1H)

LC/MS (method LC-A): $R_t$ 3.39 min, MH$^+$ 567
$[α]_D^{20}$: +31.1° (c 0.2736, DMF)
Chiral SFC (method SFC-E): $R_t$ 2.02 min, MH$^+$ 567, chiral purity 100%.

Enantiomer 5B:
$^1$H NMR (500 MHz, DMSO-$d_6$) δ ppm 3.09-3.25 (m, 2H) 3.60-3.67 (m, 5H) 3.78-3.87 (m, 2H) 3.90 (s, 3H) 4.04 (td, J=10.2, 6.9 Hz, 1H) 4.37 (td, J=10.2, 6.8 Hz, 1H) 4.79 (t, J=5.5 Hz, 1H) 5.59 (d, J=8.5 Hz, 1H) 5.76 (t, J=1.9 Hz, 1H) 5.87 (br s, 2H) 6.47 (d, J=8.5 Hz, 1H) 6.99-7.05 (m, 2H) 7.14 (d, J=1.9 Hz, 1H) 7.31 (d, J=8.2 Hz, 1H) 7.34 (d, J=8.2 Hz, 1H) 8.02 (s, 1H)

LC/MS (method LC-A): $R_t$ 3.39 min, MH$^+$ 567
$[α]_D^{20}$: −31.0° (c 0.2773, DMF)
Chiral SFC (method SFC-E): $R_t$ 3.00 min. MH$^+$ 567, chiral purity 100%.

Example 6.1: Synthesis of 2-(4-chloro-2-fluorophenyl)-2-((3-(2-hydroxyethoxy)-5-methoxyphenyl)amino)-1-(6-(trifluoromethoxy)indolin-1-yl)ethanone (Compound 6)

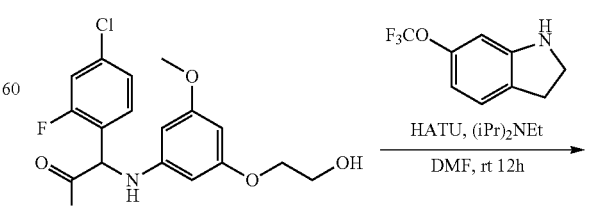

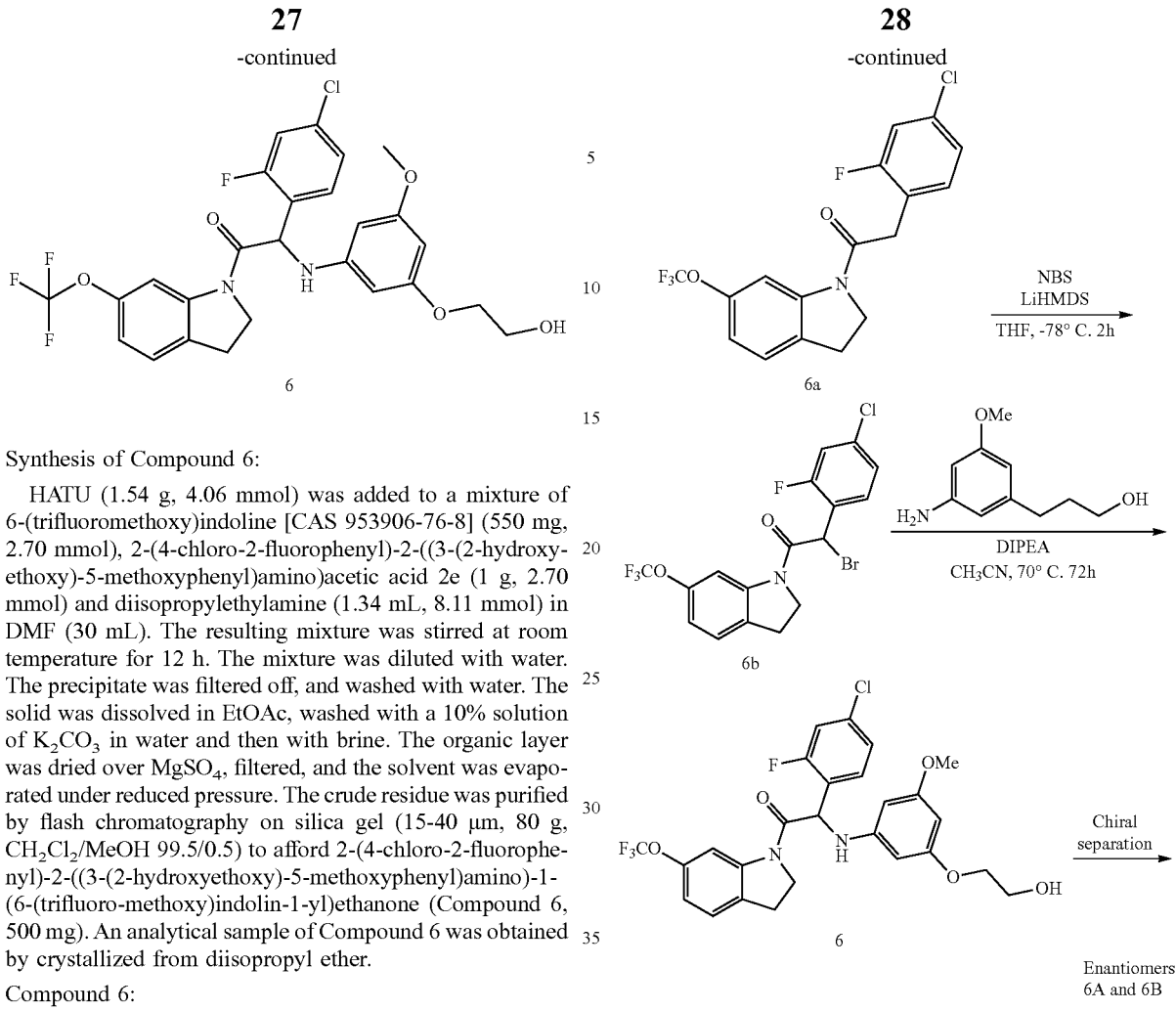

Synthesis of Compound 6:

HATU (1.54 g, 4.06 mmol) was added to a mixture of 6-(trifluoromethoxy)indoline [CAS 953906-76-8] (550 mg, 2.70 mmol), 2-(4-chloro-2-fluorophenyl)-2-((3-(2-hydroxyethoxy)-5-methoxyphenyl)amino)acetic acid 2e (1 g, 2.70 mmol) and diisopropylethylamine (1.34 mL, 8.11 mmol) in DMF (30 mL). The resulting mixture was stirred at room temperature for 12 h. The mixture was diluted with water. The precipitate was filtered off, and washed with water. The solid was dissolved in EtOAc, washed with a 10% solution of $K_2CO_3$ in water and then with brine. The organic layer was dried over $MgSO_4$, filtered, and the solvent was evaporated under reduced pressure. The crude residue was purified by flash chromatography on silica gel (15-40 µm, 80 g, $CH_2Cl_2$/MeOH 99.5/0.5) to afford 2-(4-chloro-2-fluorophenyl)-2-((3-(2-hydroxyethoxy)-5-methoxyphenyl)amino)-1-(6-(trifluoro-methoxy)indolin-1-yl)ethanone (Compound 6, 500 mg). An analytical sample of Compound 6 was obtained by crystallized from diisopropyl ether.

Compound 6:

$^1$H NMR (500 MHz, DMSO-$d_6$) δ ppm 3.14-3.22 (m, 2H) 3.58-3.68 (m, 5H) 3.80-3.90 (m, 2H) 4.05-4.15 (m, 1H) 4.38-4.47 (m, 1H) 4.80 (t, J=5.5 Hz, 1H) 5.70 (d, J=9.1 Hz, 1H) 5.79 (t, J=1.9 Hz, 1H) 5.93 (d, J=1.9 Hz, 2H) 6.63 (d, J=9.1 Hz, 1H) 7.03 (dd, J=8.2, 1.6 Hz, 1H) 7.31-7.37 (m, 2H) 7.42-7.51 (m, 2H) 8.02 (s, 1H)

LC/MS (method LC-A): $R_t$ 3.39 min, MH$^+$ 555

Melting point: 166° C.

Example 6.2: Synthesis of 2-(4-chloro-2-fluorophenyl)-2-((3-(2-hydroxyethoxy)-5-methoxyphenyl)amino)-1-(6-(trifluoromethoxy)indolin-1-yl)ethanone (Compound 6) and Chiral Separation into Enantiomers 6A and 6B

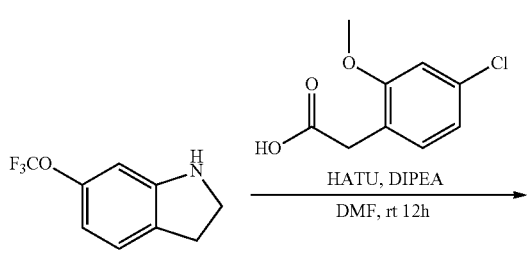

Synthesis of Intermediate 6a:

HATU (7.02 g, 18.5 mmol) was added to a mixture of 6-(trifluoromethoxy)indoline [CAS 953906-76-8] (2.5 g, 12.31 mmol), 2-(4-chloro-2-fluorophenyl)acetic acid [CAS 194240-75-0] (2.32 g, 12.3 mmol) and diisopropylethylamine (6.1 mL, 36.9 mmol) in DMF (100 mL). The resulting mixture was stirred at room temperature for 12 h. The mixture was diluted with water and the precipitate was filtered off and washed with water. The residue was taken up with EtOAc and the organic layer was washed with a 10% solution of $K_2CO_3$ in water, washed with brine, dried over $MgSO_4$, filtered, and the solvent was evaporated under reduced pressure. The crude product was crystallized from diisopropyl ether to give 2-(4-chloro-2-fluorophenyl)-1-(6-(trifluoromethoxy)indolin-1-yl)ethanone 6a (4 g).

Synthesis of Intermediate 6b:

At −78° C., under a $N_2$ flow, LiHMDS 1M in THF (21.4 mL, 21.4 mmol) was added dropwise to a mixture of 2-(4-chloro-2-fluorophenyl)-1-(6-(trifluoromethoxy)indolin-1-yl)ethanone 6a (4 g, 10.7 mmol) in THF (60 mL). The mixture was stirred for 15 min at −78° C. and a solution of NBS (2.1 g, 11.8 mmol) in THF (40 mL) was added dropwise. After stirring for 2 h at −78° C., the reaction was quenched with a saturated aqueous solution of $NH_4Cl$. The mixture was extracted with EtOAc, dried over $MgSO_4$, filtered, and the solvent was evaporated under reduced pressure to give 2-bromo-2-(4-chloro-2-fluorophenyl)-1-(6-(trifluoromethoxy)indolin-1-yl)ethanone 6b (4.8 g). The compound was used as such in the next step.

Synthesis of Compound 6 and chiral separation into Enantiomers 6A and 6B:

A mixture of 2-bromo-2-(4-chloro-2-fluorophenyl)-1-(6-(trifluoromethoxy)indolin-1-yl)ethanone 6b (4.8 g, 10.6 mmol), 2-(3-amino-5-methoxyphenoxy)ethanol [CAS 725237-16-1] (2.3 g, 12.7 mmol) and diisopropylethylamine (2.2 mL, 12.7 mmol) in $CH_3CN$ (200 mL) was stirred at 70° C. for 72 h. The mixture was concentrated under reduced pressure, diluted with EtOAc and washed with 1N HCl and water. The organic phase was separated, dried over $MgSO_4$, filtered, and the solvent was evaporated under reduced pressure. The compound was purified by flash chromatography on silica gel (15-40 µm, 80 g, $CH_2Cl_2$/MeOH 99.5/0.5). The pure fractions were combined and evaporated to dryness to give racemic 2-(4-chloro-2-fluorophenyl)-2-((3-(2-hydroxyethoxy)-5-methoxyphenyl)amino)-1-(6-(trifluoromethoxy)indolin-1-yl)ethanone (Compound 6, 3 g) after crystallization from $CH_3CN$/diisopropyl ether. The enantiomers were separated via Preparative Chiral SFC (Stationary phase: Chiralcel® OD-H 5 µm 250×30 mm, Mobile phase: 60% $CO_2$, 40% EtOH (+0.3% $iPrNH_2$)). The first eluted enantiomer (1.45 g) was solidified by trituration with MeOH/water to give Enantiomer 6A (1.409 g). The second eluted enantiomer (1.41 g) was solidified by trituration with MeOH/water to give Enantiomer 6B (1.37 g).

Enantiomer 6A:
$^1$H NMR (400 MHz, DMSO-$d_6$) δ ppm 3.13-3.21 (m, 2H) 3.60-3.68 (m, 5H) 3.78-3.91 (m, 2H) 4.04-4.14 (m, 1H) 4.37-4.48 (m, 1H) 4.77 (t, J=5.6 Hz, 1H) 5.69 (d, J=9.1 Hz, 1H) 5.80 (s, 1H) 5.93 (d, J=1.5 Hz, 2H) 6.60 (br d, J=9.1 Hz, 1H) 7.02 (br d, J=8.1 Hz, 1H) 7.30-7.38 (m, 2H) 7.41-7.51 (m, 2H) 8.02 (s, 1H)

LC/MS (method LC-A): $R_t$ 3.41 min, MH$^+$ 555
[α]D20: −25.9° (c 0.27, DMF)
Chiral SFC (method SFC-F): $R_t$ 4.08 min, MH$^+$ 555, chiral purity 100%.

Enantiomer 6B:
$^1$H NMR (400 MHz, DMSO-$d_6$) δ ppm 3.13-3.20 (m, 2H) 3.59-3.68 (m, 5H) 3.79-3.91 (m, 2H) 4.04-4.14 (m, 1H) 4.38-4.49 (m, 1H) 4.77 (t, J=5.6 Hz, 1H) 5.69 (d, J=9.1 Hz, 1H) 5.80 (s, 1H) 5.93 (d, J=2.0 Hz, 2H) 6.60 (d, J=8.6 Hz, 1H) 7.02 (br d, J=9.1 Hz, 1H) 7.29-7.38 (m, 2H) 7.42-7.50 (m, 2H) 8.02 (s, 1H)

LC/MS (method LC-A): $R_t$ 3.41 min, MH$^+$ 555
$[α]_D^{20}$: +23.3° (c 0.27, DMF)
Chiral SFC (method SFC-F): $R_t$ 2.25 min, MH$^+$ 555, chiral purity 99.42%.

Example 7.1: Synthesis of 2-(4-chlorophenyl)-2-((3-(2-hydroxyethoxy)-5-methoxy-phenyl)amino)-1-(5-methoxy-6-(trifluoromethyl)indolin-1-yl)ethanone (Compound 7)

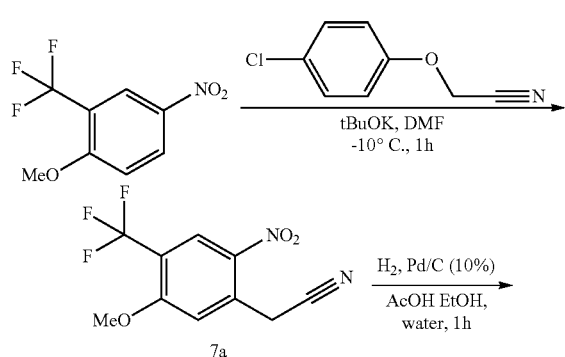

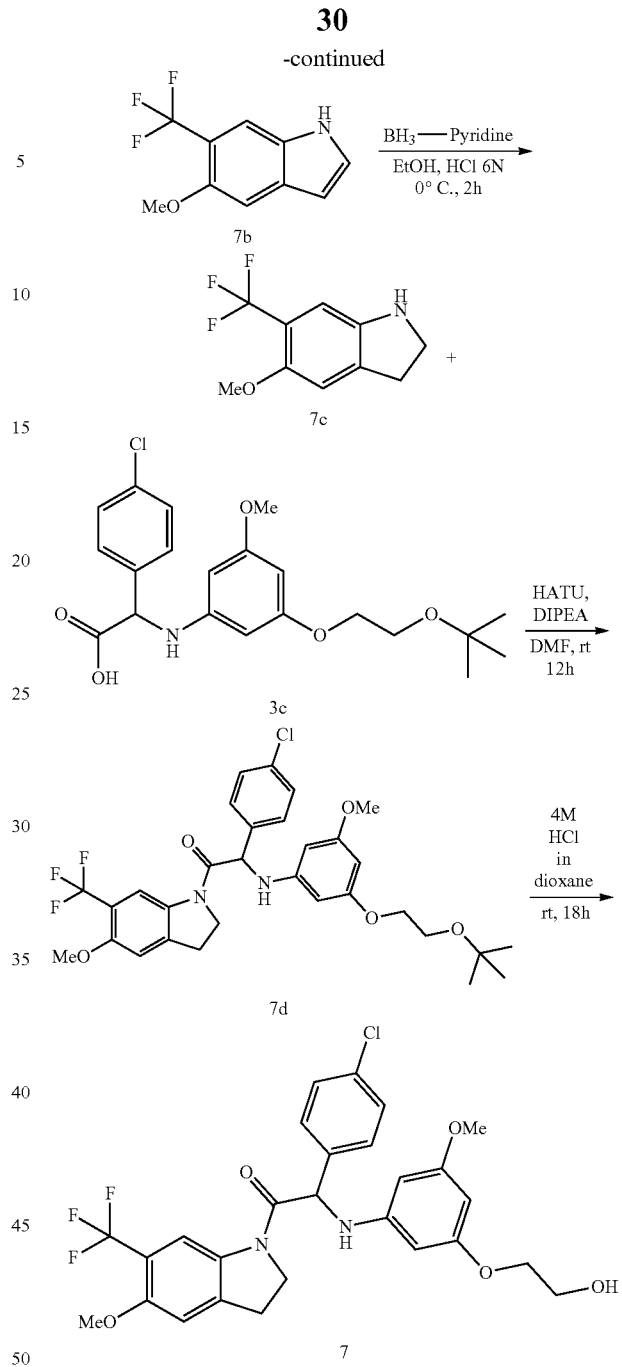

Synthesis of Intermediate 7a:

A mixture of 1-methoxy-4-nitro-2-(trifluoromethyl)benzene [CAS 654-76-2] (24.5 g, 110.8 mmol) and 4-chlorophenoxyacetonitrile [CAS 3598-13-8] (20.4 g, 121.9 mmol) in DMF (100 mL) was added dropwise over 30 min to a stirred solution of tBuOK (27.4 g, 243.7 mmol) in DMF (100 mL) at −10° C. After addition, the purple solution was maintained at −10° C. for 1 h. Ice-water (500 mL) and 6N HCl (500 mL) were added and the precipitate was filtered off, washed with water and dried under vacuum to afford 2-(5-methoxy-2-nitro-4-(trifluoromethyl)-phenyl)acetonitrile 7a (40.4 g) which was used as such in the next step.

Synthesis of Intermediate 7b:

A solution of 2-(5-methoxy-2-nitro-4-(trifluoromethyl)phenyl)acetonitrile 7a (26 g, 99.9 mmol) in ethanol/water (9/1) (500 mL) and AcOH (5.2 mL) was hydrogenated for 1 h under pressure (3.5 Bar) with 10% Pd/C (15.3 g) as the catalyst. The reaction mixture was filtered through a pad of Celite® and the filter cake was washed with a mixture of $CH_2Cl_2$ and $CH_3OH$. The combined filtrates were concentrated under reduced pressure. The crude residue was filtered through a pad of silica (60-200 μm) using heptane/EtOAc 80/20 as the eluent. The fractions containing the expected compound were combined and the solvent was concentrated under reduced pressure to give 5-methoxy-6-(trifluoromethyl)-1H-indole 7b (15.6 g).

Synthesis of Intermediate 7c:

At 0° C., $BH_3$—Pyridine (23.5 mL, 232.4 mmol) was added dropwise to a solution of 5-methoxy-6-(trifluoromethyl)-1H-indole 7b (10 g, 46.5 mmol) in EtOH (60 mL). 6N HCl (140 mL) was slowly added while maintaining the reaction temperature below 10° C. The mixture was stirred at 0° C. for 2 h. Water (200 mL) was added and the mixture was basified until pH 8-9 with a concentrated solution of NaOH in water, while keeping the reaction temperature below 20° C. The precipitate was filtered off, washed with water (twice) and co-evaporated under reduced pressure with toluene to give 5-methoxy-6-(trifluoromethyl)indoline 7c (9 g).

Synthesis of Intermediate 7d:

HATU (0.84 g, 2.21 mmol) was added to a mixture of 5-methoxy-6-(trifluoro-methyl)indoline 7c (320 mg, 1.47 mmol), 2-((3-(2-(tert-butoxy)ethoxy)-5-methoxy-phenyl)amino)-2-(4-chlorophenyl)acetic acid 3c (631 mg, 1.55 mmol) and diisopropylethylamine (731 μL, 4.42 mmol) in DMF (18 mL). The reaction mixture was stirred at room temperature for 12 h. The reaction was diluted with water and EtOAc. The organic layer was separated, washed with a 10% solution of $K_2CO_3$ in water, dried over $MgSO_4$, filtered and the solvent was evaporated under reduced pressure. The crude residue was purified by flash chromatography on silica gel (15-40 μm, 80 g, $CH_2Cl_2$/MeOH 99.5/0.5) to give 2-((3-(2-(tert-butoxy)ethoxy)-5-methoxyphenyl)amino)-2-(4-chlorophenyl)-1-(5-methoxy-6-(trifluoromethyl)-indolin-1-yl)ethanone 7d (839 mg).

Synthesis of Compound 7:

2-((3-(2-(tert-Butoxy)ethoxy)-5-methoxyphenyl)amino)-2-(4-chlorophenyl)-1-(5-methoxy-6-(trifluoromethyl)indolin-1-yl)ethanone 7d (1.15 g, 1.89 mmol) was added to 4M HCl in dioxane (20 mL) and the mixture was stirred at room temperature for 18 h. The mixture was diluted with water and was basified with $K_2CO_3$. The aqueous layer was extracted with EtOAc. The organic layer was washed with water, dried over $MgSO_4$, filtered, and the solvent was evaporated under reduced pressure. Purification was carried out by flash chromatography on silica gel (15-40 μm, 40 g, $CH_2Cl_2$/MeOH/$NH_4OH$ 99/1/0.1). The pure fractions were combined and evaporated to dryness to afford 2-(4-chlorophenyl)-2-((3-(2-hydroxyethoxy)-5-methoxyphenyl)amino)-1-(5-methoxy-6-(trifluoromethyl)-indolin-1-yl)ethanone (Compound 7, 915 mg). An analytical sample of Compound 7 was obtained by crystallized from $CH_3CN$.

Compound 7:

$^1$H NMR (500 MHz, DMSO-$d_6$) δ ppm 3.15-3.29 (m, 2H) 3.60-3.68 (m, 5H) 3.79-3.90 (m, 5H) 3.96-4.07 (m, 1H) 4.51 (td, J=10.4, 6.0 Hz, 1H) 4.78 (t, J=5.0 Hz, 1H) 5.54 (d, J=8.5 Hz, 1H) 5.76 (s, 1H) 5.95 (s, 2H) 6.40 (br d, J=8.5 Hz, 1H) 7.23 (s, 1H) 7.44 (d, J=8.5 Hz, 2H) 7.56 (d, J=8.5 Hz, 2H) 8.34 (s, 1H)

LC/MS (method LC-A): $R_t$ 3.21 min, MH$^+$ 551

Melting point: 188° C.

Example 7.2: Synthesis of 2-(4-chlorophenyl)-2-((3-(2-hydroxyethoxy)-5-methoxy-phenyl)amino)-1-(5-methoxy-6-(trifluoromethyl)indolin-1-yl)ethanone (Compound 7) and Chiral Separation into Enantiomers 7A and 7B

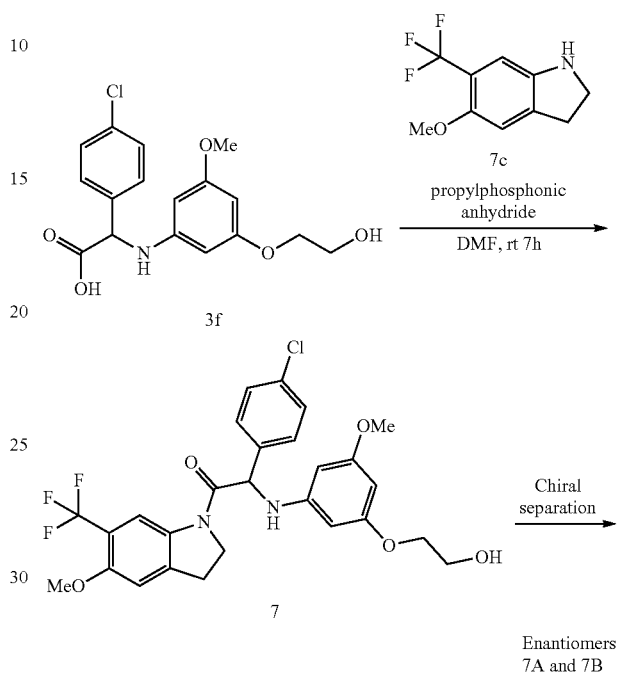

Synthesis of Compound 7 and Chiral Separation into Enantiomers 7A and 7B:

Under $N_2$ flow, at 5° C., propylphosphonic anhydride (4.15 mL, 6.91 mmol) was added dropwise to a mixture of 5-methoxy-6-(trifluoromethyl)indoline 7c (1 g, 4.60 mmol), 2-(4-chlorophenyl)-2-((3-(2-hydroxyethoxy)-5-methoxyphenyl)amino)acetic acid 3f (1.94 g, 5.53 mmol) and diisopropylethylamine (1.67 mL, 10.1 mmol) in DMF (20 mL). The mixture was stirred at room temperature for 7 h. Water was added and the mixture was extracted with EtOAc. The organic layer was washed with a 10% solution of $K_2CO_3$ in water, and then with water. The organic layer was dried over $MgSO_4$, filtered and the solvent was evaporated under reduced pressure. Purification was carried out by flash chromatography on silica gel, (15-40 μm, 90 g, $CH_2Cl_2$/MeOH 99/1). The pure fractions were combined and evaporated to dryness, to give 2-(4-chlorophenyl)-2-((3-(2-hydroxyethoxy)-5-methoxyphenyl)amino)-1-(5-methoxy-6-(trifluoromethyl)indolin-1-yl)ethanone (Compound 7, 2.17 g) as a racemic mixture. The enantiomers were separated via Preparative Chiral SFC (Stationary phase: Chiralpak® IA 5 μm 250×20 mm, Mobile phase: 45% $CO_2$, 55% iPrOH (+0.3% iPrNH$_2$)). The first eluted enantiomer (980 mg) was crystallized from MeOH to afford Enantiomer 7A (711 mg). The second eluted enantiomer (1.08 g) was further purified by flash chromatography on silica gel (15-40 μm, 40 g, $CH_2Cl_2$/MeOH 99.5/0.5). The pure fractions were combined and evaporated to dryness (950 mg) to afford, after crystallization from MeOH, Enantiomer 7B (770 mg).

Enantiomer 7A:

¹H NMR (500 MHz, DMSO-d₆) δ ppm 3.15-3.31 (m, 2H) 3.60-3.68 (m, 5H) 3.79-3.90 (m, 5H) 3.95-4.04 (m, 1H) 4.51 (td, J=10.4, 6.3 Hz, 1H) 4.80 (t, J=5.4 Hz, 1H) 5.54 (d, J=8.5 Hz, 1H) 5.76 (s, 1H) 5.95 (s, 2H) 6.41 (d, J=8.5 Hz, 1H) 7.24 (s, 1H) 7.44 (d, J=8.2 Hz, 2H) 7.56 (d, J=8.5 Hz, 2H) 8.34 (s, 1H)

LC/MS (method LC-A): $R_t$ 3.22 min, MH⁺ 551

[α]D20: −45.2° (c 0.314, DMF)

Chiral SFC (method SFC-G): $R_t$ 2.35 min, MH⁺ 551, chiral purity 100%.

Melting point: 112° C.

Enantiomer 7B:

¹H NMR (500 MHz, DMSO-d₆) δ ppm 3.15-3.31 (m, 2H) 3.60-3.68 (m, 5H) 3.79-3.90 (m, 5H) 3.95-4.05 (m, 1H) 4.51 (td, J=10.3, 6.5 Hz, 1H) 4.80 (br t, J=5.0 Hz, 1H) 5.54 (d, J=8.8 Hz, 1H) 5.76 (s, 1H) 5.95 (s, 2H) 6.41 (d, J=8.8 Hz, 1H) 7.24 (s, 1H) 7.44 (d, J=8.5 Hz, 2H) 7.56 (d, J=8.5 Hz, 2H) 8.34 (s, 1H)

LC/MS (method LC-A): $R_t$ 3.21 min, MH⁺ 551

[α]D20: +43.8° (c 0.27, DMF)

Chiral SFC (method SFC-G): $R_t$ 3.84 min, MH⁺ 551, chiral purity 100%.

Melting point: 112° C.

Example 8.1: Synthesis of 2-(4-chloro-2-fluorophenyl)-2-((3-(2-hydroxyethoxy)-5-methoxyphenyl)amino)-1-(5-methoxy-6-(trifluoromethyl)indolin-1-yl)ethanone (Compound 8)

The organic layer was washed with a 10% solution of K₂CO₃ in water and with brine, dried over MgSO₄, filtered, and the solvent was evaporated under reduced pressure. The crude residue was purified by flash chromatography on silica gel (15-40 μm, 80 g, CH₂Cl₂/MeOH 99.5/0.5). The residue was crystallized from Et₂O/diisopropyl ether to give 2-(4-chloro-2-fluorophenyl)-2-((3-(2-hydroxyethoxy)-5-methoxyphenyl)amino)-1-(5-methoxy-6-(trifluoromethyl)indolin-1-yl)ethanone (Compound 8, 35 mg).

Compound 8:

¹H NMR (500 MHz, DMSO-d₆) δ ppm 3.19-3.28 (m, 2H) 3.59-3.69 (m, 5H) 3.85 (m, 5H) 3.99-4.08 (m, 1H) 4.37-4.47 (m, 1H) 4.80 (t, J=5.4 Hz, 1H) 5.68 (br d, J=9.1 Hz, 1H) 5.79 (s, 1H) 5.93 (s, 2H) 6.58 (br d, J=9.1 Hz, 1H) 7.26 (s, 1H) 7.33 (br d, J=7.6 Hz, 1H) 7.42-7.52 (m, 2H) 8.33 (s, 1H)

LC/MS (method LC-A): $R_t$ 3.27 min, MH⁺ 569

Melting point: 176° C.

Example 8.2: Synthesis of 2-(4-chloro-2-fluorophenyl)-2-((3-(2-hydroxyethoxy)-5-methoxyphenyl)amino)-1-(5-methoxy-6-(trifluoromethyl)indolin-1-yl)ethanone (Compound 8) and Chiral Separation into Enantiomers 8A and 8B

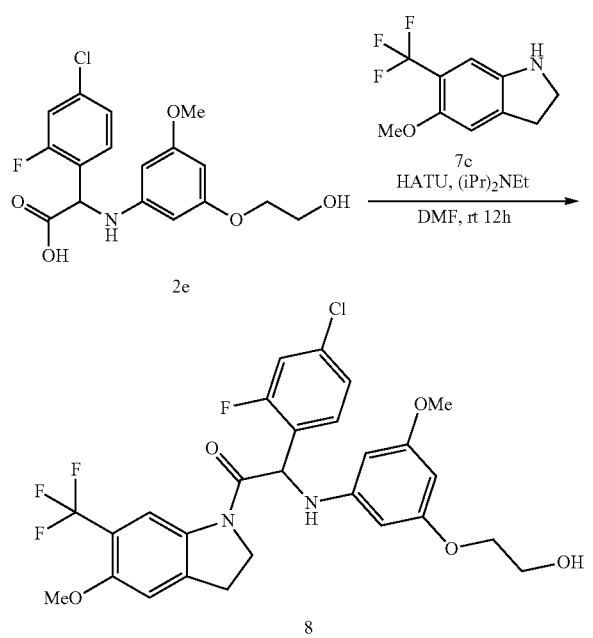

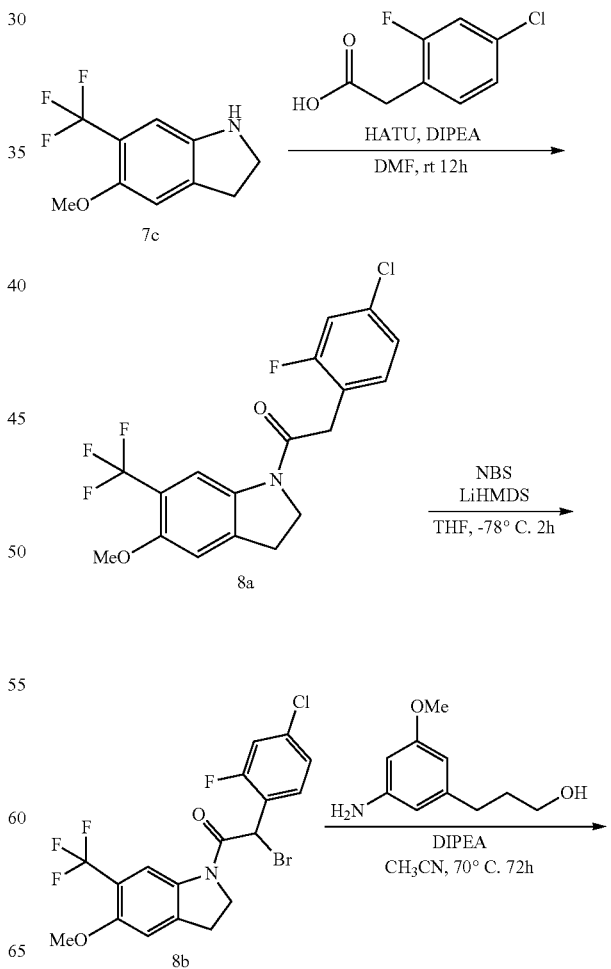

Synthesis of Compound 8:

HATU (308 mg, 0.81 mmol) was added to a mixture of 5-methoxy-6-(trifluoro-methyl)indoline 7c (117 mg, 0.54 mmol), 2-(4-chloro-2-fluorophenyl)-2-((3-(2-hydroxyethoxy)-5-methoxyphenyl)amino)acetic acid 2e (200 mg, 0.54 mmol) and diisopropylethylamine (0.267 mL, 1.61 mmol) in DMF (10 mL). The reaction mixture was stirred at room temperature for 12 h. The reaction was diluted with water, causing precipitation. The precipitate was filtered off and washed with water. The solid was dissolved in EtOAc.

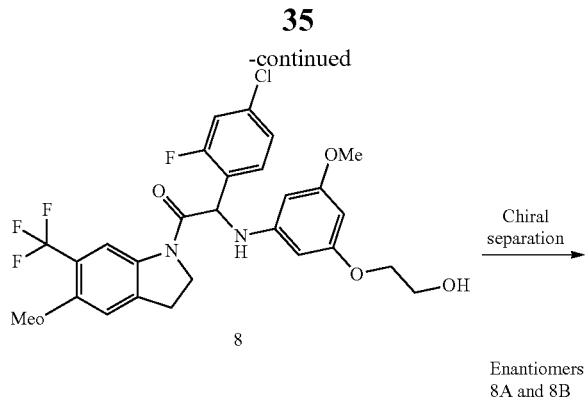

Synthesis of intermediate 8a:

HATU (2.9 g, 7.6 mmol) was added to a mixture of 5-methoxy-6-(trifluoromethyl)-indoline 7c (1.1 g, 5.06 mmol), 2-(4-chloro-2-fluorophenyl)acetic acid [CAS 194240-75-0] (1.05 g, 5.57 mmol) and diisopropylethylamine (2.51 mL, 15.2 mmol) in DMF (30 mL). The reaction mixture was stirred at room temperature for 12 h. The mixture was diluted with water, causing precipitation. The precipitate was filtered off and washed with water. The residue was taken up with EtOAc and the organic solution was washed with a 10% solution of $K_2CO_3$ in water and then with brine. The organic solution was dried over $MgSO_4$, filtered, and the solvent was evaporated under reduced pressure. The crude residue was purified by flash chromatography on silica gel (15-40 μm, 80 g, heptane/EtOAc 90/10 to 60/40). The pure fractions were combined and the solvent was evaporated under reduced pressure to give 2-(4-chloro-2-fluorophenyl)-1-(5-methoxy-6-(trifluoromethyl)-indolin-1-yl)ethanone 8a (1.8 g).

Synthesis of Intermediate 8b:

At −78° C., under a $N_2$ flow, LiHMDS 1M in THF (9.3 mL, 9.3 mmol) was added dropwise to a mixture of 2-(4-chloro-2-fluorophenyl)-1-(5-methoxy-6-(trifluoro-methyl)indolin-1-yl)ethanone 8a (1.8 g, 4.65 mmol) in THF (25 mL). TMSCl (0.7 mL, 0.86 mmol) was added dropwise. The mixture was stirred for 15 min at −78° C. and a solution of NBS (1 g, 5.57 mmol) in THF (15 mL) was added dropwise. After stirring for 2 h at −78° C., the reaction was quenched by the addition of a saturated aqueous solution of $NH_4Cl$. The mixture was extracted with EtOAc. The organic layer was dried over $MgSO_4$, filtered, and the solvent was evaporated under reduced pressure to give 2-bromo-2-(4-chloro-2-fluorophenyl)-1-(5-methoxy-6-(trifluoromethyl)indolin-1-yl)ethanone 8b (2.1 g). The compound was used as such in the next step.

Synthesis of Compound 8 and Chiral Separation into Enantiomers 8A and 8B:

A mixture of 2-bromo-2-(4-chloro-2-fluorophenyl)-1-(5-methoxy-6-(trifluoromethyl)-indolin-1-yl)ethanone 8b (2.1 g, 4.5 mmol), 2-(3-amino-5-methoxyphenoxy)-ethanol [CAS 725237-16-1] (0.99 g, 5.4 mmol) and diisopropylethylamine (1.16 mL, 6.75 mmol) in $CH_3CN$ (80 mL) was stirred at 70° C. for 72 h. The mixture was concentrated under reduced pressure, diluted with EtOAc and washed with 1N HCl and water. The organic phase was separated, dried over $MgSO_4$, filtered and the solvent was evaporated under reduced pressure. The compound was purified by flash chromatography on silica gel (15-40 μm, 80 g, $CH_2Cl_2$). The pure fractions were combined and evaporated to dryness to give racemic 2-(4-chloro-2-fluoro-phenyl)-2-((3-(2-hydroxyethoxy)-5-methoxyphenyl)amino)-1-(5-methoxy-6-(trifluoromethyl)indolin-1-yl)ethanone (Compound 8, 850 mg) after crystallization from $CH_3CN$. This fraction was combined with another batch (total amount: 1.3 g). The enantiomers were separated via Preparative Chiral SFC (Stationary phase: Chiralpak® IA 5 μm 250×20 mm, Mobile phase: 70% $CO_2$, 30% EtOH (+0.3% $iPrNH_2$)). The first eluted enantiomer (680 mg) was solidified by trituration with $CH_3CN$ to give Enantiomer 8A (590 mg). The second eluted enantiomer (630 mg) was solidified by trituration with $CH_3CN$ to give Enantiomer 8B (569 mg).

Enantiomer 8A:

$^1$H NMR (400 MHz, DMSO-$d_6$) δ ppm 3.19-3.27 (m, 2H) 3.59-3.69 (m, 5H) 3.78-3.91 (m, 5H) 3.98-4.08 (m, 1H) 4.35-4.47 (m, 1H) 4.77 (t, J=5.6 Hz, 1H) 5.67 (d, J=9.1 Hz, 1H) 5.79 (t, J=1.8 Hz, 1H) 5.93 (d, J=2.0 Hz, 2H) 6.55 (d, J=9.1 Hz, 1H) 7.25 (s, 1H) 7.31 (dd, J=8.3, 1.8 Hz, 1H) 7.42-7.50 (m, 2H) 8.32 (s, 1H)

LC/MS (method LC-A): $R_t$ 3.26 min, MH$^+$ 569

$[α]_D^{20}$: −28.9° (c 0.225, DMF)

Chiral SFC (method SFC-H): $R_t$ 4.51 min, MH$^+$ 569, chiral purity 100%.

Enantiomer 8B:

$^1$H NMR (400 MHz, DMSO-$d_6$) δ ppm 3.19-3.27 (m, 2H) 3.59-3.68 (m, 5H) 3.80-3.90 (m, 5H) 3.98-4.09 (m, 1H) 4.35-4.47 (m, 1H) 4.77 (t, J=5.3 Hz, 1H) 5.67 (d, J=9.1 Hz, 1H) 5.79 (t, J=1.8 Hz, 1H) 5.93 (d, J=1.5 Hz, 2H) 6.54 (d, J=8.6 Hz, 1H) 7.25 (s, 1H) 7.31 (dd, J=8.6, 2.0 Hz, 1H) 7.42-7.50 (m, 2H) 8.32 (s, 1H)

LC/MS (method LC-A): $R_t$ 3.26 min, MH$^+$ 569

$[α]_D^{20}$: +25.7° (c 0.2333, DMF)

Chiral SFC (method SFC-H): $R_t$ 5.81 min, MH$^+$ 569, chiral purity 100%.

Example 9: Synthesis of 2-(4-chlorophenyl)-2-((3-(2-hydroxyethoxy)-5-methoxy-phenyl)amino)-1-(4-methyl-6-(trifluoromethoxy)indolin-1-yl)ethanone (Compound 9) and Chiral Separation into Enantiomers 9A and 9B

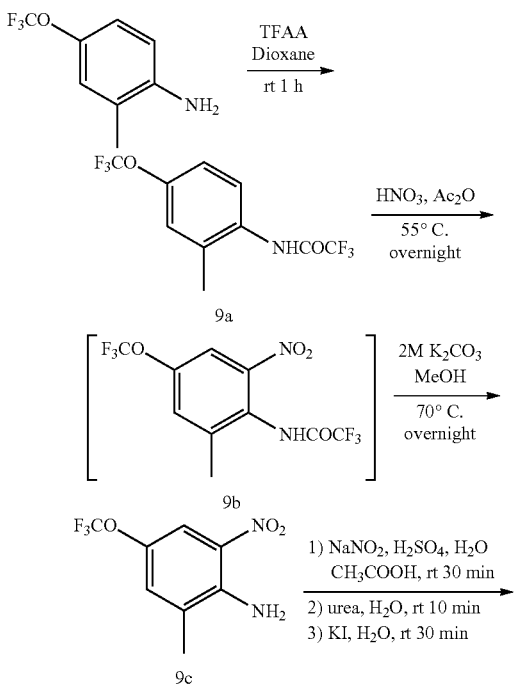

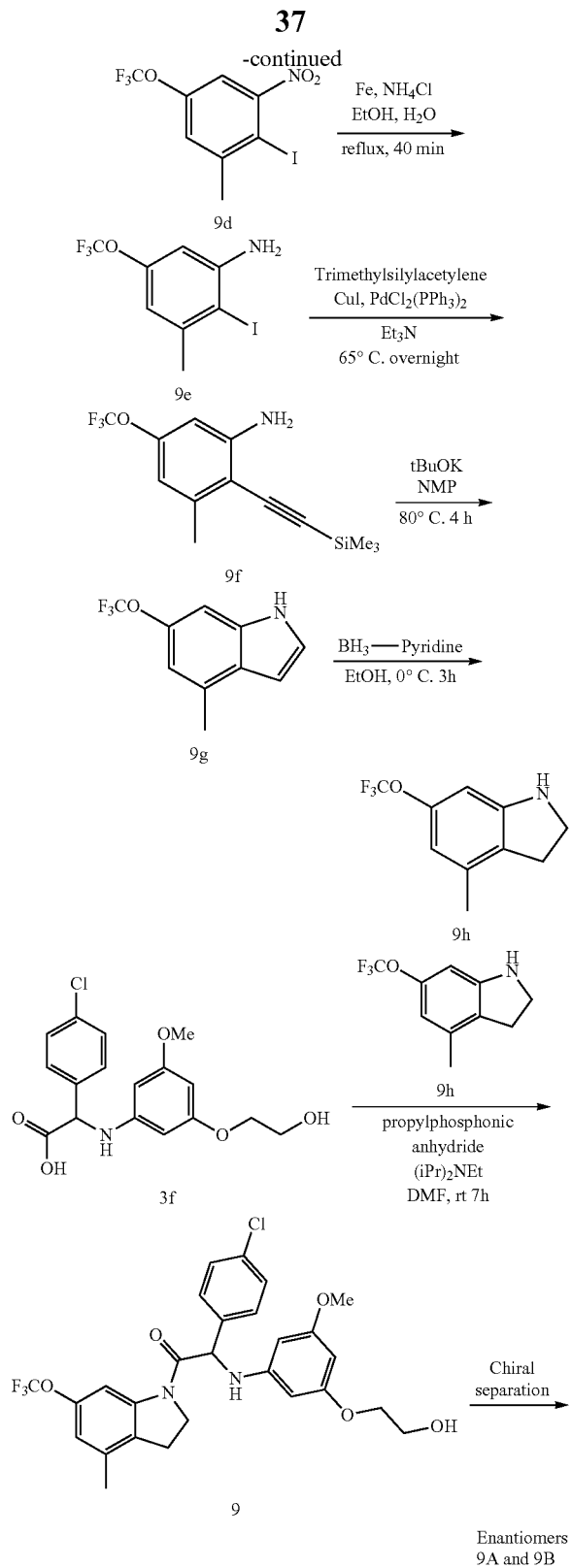

The residue was partitioned between EtOAc and 1N HCl. The phases were separated. The organic phase was washed with a saturated solution of NaHCO$_3$ in water, H$_2$O and brine, dried over Na$_2$SO$_4$, filtered and concentrated under reduced pressure to afford 14.7 g of 2,2,2-trifluoro-N-(2-methyl-4-(trifluoromethoxy)phenyl)acetamide 9a as a white powder. The compound was used in the next step without further purification.

Synthesis of Intermediate 9c:

To acetic anhydride (11.4 mL, 61.1 mmol), cooled at 0° C. was added dropwise 70% nitric acid (3.9 mL). 2,2,2-Trifluoro-N-(2-methyl-4-(trifluoromethoxy)phenyl)-acetamide 9a (5 g, 17.4 mmol) was added portionwise and the reaction mixture was heated at 55° C. for 12 h. After cooling to room temperature, the reaction mixture was diluted with EtOAc and washed with H$_2$O. The organic phase was washed with brine, dried over Na$_2$SO$_4$, filtered and concentrated under reduced pressure. The residue was dissolved in methanol (46 mL). 2M K$_2$CO$_3$ (23 mL, 46 mmol) was added and the reaction mixture was heated at 70° C. for 4 h. More 2M K$_2$CO$_3$ (10 mL, 20 mmol) was added and the reaction mixture was heated at 70° C. for 12 h. The reaction mixture was partially concentrated under reduced pressure to remove methanol. The residue was extracted with EtOAc. The organic phase was washed with H$_2$O and brine, dried over Na$_2$SO$_4$, filtered and concentrated under reduced pressure. The residue was purified by flash chromatography on silica gel using a gradient of EtOAc (20% to 50%) in heptane to afford 3.6 g of 2-methyl-6-nitro-4-(trifluoromethoxy)aniline 9c as a yellow solid.

Synthesis of Intermediate 9d:

To a solution of 2-methyl-6-nitro-4-(trifluoromethoxy)aniline 9c (1.8 g, 7.69 mmol) in acetic acid (10.9 mL) was added dropwise a solution of sodium nitrite (0.806 g, 11.7 mmol) in H$_2$SO$_4$/H$_2$O (2 mL, 1/1). The reaction mixture was stirred at room temperature for 30 min. H$_2$O (22 mL) and urea (0.802 g, 13.4 mmol) were added. After 10 min at room temperature, a solution of potassium iodide (1.7 g, 10.2 mmol) in H$_2$O (11 mL) was added dropwise. The reaction mixture was stirred at room temperature for 30 min. The yellow solid was filtered off, washed with H$_2$O and dried to give 2.4 g of 2-iodo-1-methyl-3-nitro-5-(trifluoromethoxy)benzene 9d.

Synthesis of Intermediate 9e:

To a solution of 2-iodo-1-methyl-3-nitro-5-(trifluoromethoxy)benzene 9d (3.5 g, 10.0 mmol) in EtOH (30 mL) was added a solution of NH$_4$Cl (2.7 g, 49.9 mmol) in H$_2$O (30 mL). The reaction mixture was heated at 50° C. Iron (2.6 g, 46.9 mmol) was added and the reaction mixture was heated under reflux for 40 min. After cooling to room temperature, the reaction mixture was filtered through Celite®. The solids were washed with EtOH. The filtrate was partially concentrated under reduced pressure to remove EtOH. The residue was partitioned between EtOAc and a saturated solution of NaHCO$_3$ in water. The phases were separated. The organic phase was washed with H$_2$O and brine, dried over Na$_2$SO$_4$, filtered and concentrated under reduced pressure. The residue was purified by flash chromatography on silica gel using a gradient of EtOAc (0% to 25%) in heptane to afford 2.9 g of 2-iodo-3-methyl-5-(trifluoromethoxy)aniline 9e as a yellow oil.

Synthesis of Intermediate 9f:

A solution of 2-iodo-3-methyl-5-(trifluoromethoxy)aniline 9e (2.9 g, 9.1 mmol) in triethylamine (23 mL) was degassed with argon for 15 min. Dichlorobis(triphenylphosphine)palladium(II) (0.327 g, 0.47 mmol), copper(I) iodide (0.164 g, 0.86 mmol) and trimethylsilylacetylene (1.8 mL, Synthesis of Intermediate 9a:

To a solution of 2-methyl-4-(trifluoromethoxy)aniline [CAS 86256-59-9] (10.0 g, 52.3 mmol) in dioxane (20 mL) was added trifluoroacetic anhydride (8 mL, 57.2 mmol). The reaction mixture was stirred at room temperature for 1 h. The reaction mixture was concentrated under reduced pressure.

13.1 mmol) were added. The reaction mixture was heated at 65° C. for 12 h. After cooling to room temperature, the reaction mixture was diluted with H$_2$O and extracted with EtOAc (3×). The organic phases were combined, washed with H$_2$O and brine, dried over Na$_2$SO$_4$, filtered and concentrated under reduced pressure. The residue was purified by flash chromatography on silica gel using a gradient of EtOAc (0% to 20%) in heptane to afford 2.6 g of 3-methyl-5-(trifluoromethoxy)-2-((trimethylsilyl)-ethynyl)aniline 9f as an orange oil.

Synthesis of Intermediate 9g:

To a solution of 3-methyl-5-(trifluoromethoxy)-2-((trimethylsilyl)ethynyl)aniline 9f (2.7 g, 9.3 mmol) in NMP (27 mL) was added tBuOK (3.1 g, 27.8 mmol). The reaction mixture was heated at 80° C. for 4 h. After cooling to room temperature, the reaction mixture was diluted with H$_2$O and extracted with EtOAc (2×). The organic phases were combined, washed with H$_2$O and brine, dried over Na$_2$SO$_4$, filtered and concentrated under reduced pressure. The residue was purified by flash chromatography on silica gel using a gradient of EtOAc (0% to 20%) in heptane to afford 1.7 g of 4-methyl-6-(trifluoromethoxy)-1H-indole 9g as an orange oil.

Synthesis of Intermediate 9h:

At 0° C., BH$_3$—Pyridine (1.2 mL, 11.6 mmol) was added dropwise to a solution of 4-methyl-6-(trifluoromethoxy)-1H-indole 9g (0.5 g, 2.32 mmol) in EtOH (3 mL). 6N HCl (6 mL) was slowly added dropwise while maintaining the reaction temperature below 10° C. The mixture was stirred at 0° C. for 3 h. Water (12 mL) was added and the mixture was basified until pH 8-9 with a concentrated solution of NaOH in water (the reaction temperature was kept below 20° C.). The mixture was extracted with EtOAc. The organic layer was washed with water, dried over MgSO$_4$, filtered and the solvent was evaporated under reduced pressure. Toluene was added and the solution was concentrated under reduced pressure to give 450 mg of 4-methyl-6-(trifluoromethoxy) indoline 9h.

Synthesis of Compound 9 and Chiral Separation into Enantiomers 9A and 9B:

Under N$_2$ flow at 5° C., propylphosphonic anhydride (1.87 mL, 3.11 mmol) was added dropwise to a mixture of 4-methyl-6-(trifluoromethoxy)indoline 9h (450 mg, 2.07 mmol), 2-(4-chlorophenyl)-2-((3-(2-hydroxyethoxy)-5-methoxyphenyl)-amino)acetic acid 3f (729 mg, 2.07 mmol) and diisopropylethylamine (753 µL, 4.56 mmol) in DMF (20 mL). The mixture was stirred at room temperature for 7 h. Water was added and the mixture was extracted with EtOAc. The organic layer was washed with a solution of K$_2$CO$_3$ 10% in water, then with water, dried over MgSO$_4$, filtered and the solvent was evaporated under reduced pressure. Purification was performed by flash chromatography on silica gel, (15-40 µm, 24 g, CH$_2$Cl$_2$/MeOH 99.5/0.5). The pure fractions were combined and evaporated to dryness, to give racemic 2-(4-chlorophenyl)-2-((3-(2-hydroxyethoxy)-5-methoxy-phenyl)amino)-1-(4-methyl-6-(trifluoromethoxy)indolin-1-yl)ethanone (Compound 9, 411 mg). The enantiomers of Compound 9 were separated via Preparative Chiral SFC (Stationary phase: Chiralpak® IA 5 µm 250×20 mm, Mobile phase: 50% CO$_2$, 50% iPrOH (+0.3% iPrNH$_2$)). The first eluted enantiomer (180 mg) was solidified from heptane/diisopropyl ether to afford Enantiomer 9A (121 mg). The second eluted enantiomer (180 mg) was solidified from heptane/diisopropyl ether to afford Enantiomer 9B (132 mg).

Enantiomer 9A:

$^1$H NMR (500 MHz, DMSO-d$_6$) δ ppm 2.20 (s, 3H) 2.98-3.17 (m, 2H) 3.59-3.69 (m, 5H) 3.79-3.90 (m, 2H) 4.05 (td, J=10.6, 6.9 Hz, 1H) 4.52 (td, J=10.5, 6.1 Hz, 1H) 4.77 (t, J=5.5 Hz, 1H) 5.55 (d, J=8.8 Hz, 1H) 5.76 (t, J=2.0 Hz, 1H) 5.94 (d, J=1.9 Hz, 2H) 6.43 (d, J=8.8 Hz, 1H) 6.88 (s, 1H) 7.44 (d, J=8.5 Hz, 2H) 7.55 (d, J=8.5 Hz, 2H) 7.88 (s, 1H)

LC/MS (method LC-A): R$_t$ 3.48 min, MH$^+$ 551

$[\alpha]_D^{20}$: −40.6° (c 0.2067, DMF)

Chiral SFC (method SFC-G): R$_t$ 2.08 min, MH$^+$ 551, chiral purity 100%.

Enantiomer 9B:

$^1$H NMR (500 MHz, DMSO-d$_6$) δ ppm 2.20 (s, 3H) 2.98-3.17 (m, 2H) 3.59-3.67 (m, 5H) 3.79-3.90 (m, 2H) 4.05 (td, J=10.6, 6.9 Hz, 1H) 4.52 (td, J=10.5, 6.1 Hz, 1H) 4.77 (t, J=5.5 Hz, 1H) 5.55 (d, J=8.5 Hz, 1H) 5.76 (t, J=1.9 Hz, 1H) 5.94 (d, J=1.9 Hz, 2H) 6.43 (d, J=8.8 Hz, 1H) 6.88 (s, 1H) 7.44 (d, J=8.5 Hz, 2H) 7.55 (d, J=8.5 Hz, 2H) 7.88 (s, 1H)

LC/MS (method LC-A): R$_t$ 3.48 min, MH$^+$ 551

$[\alpha]_D^{20}$ +42.6° (c 0.2392, DMF)

Chiral SFC (method SFC-G): R$_t$ 3.34 min, MH$^+$ 551, chiral purity 99.7%.

Example 10: Synthesis of 2-(4-chlorophenyl)-2-((3-(2-hydroxyethoxy)-5-methoxy-phenyl)amino)-1-(4-methyl-6-(trifluoromethyl)indolin-1-yl)ethanone (Compound 10) and Chiral Separation into Enantiomers 10A and 10B

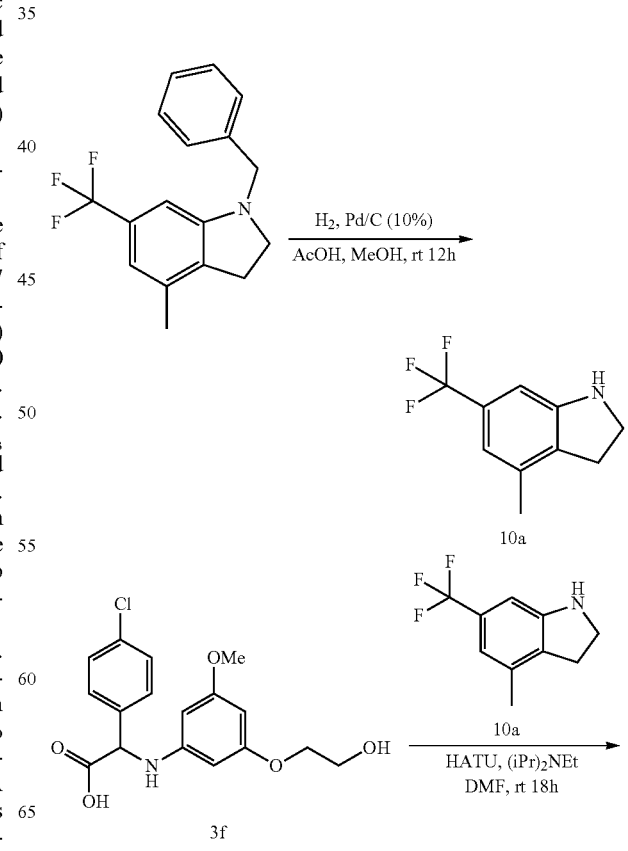

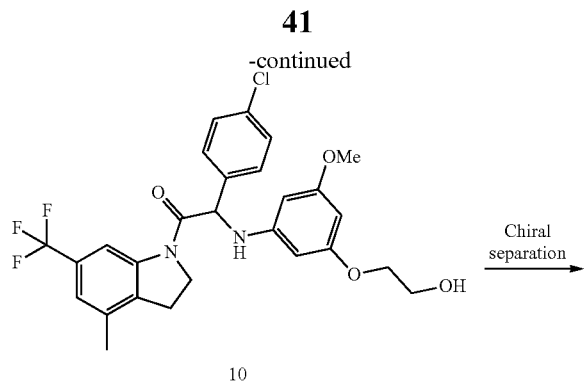

Synthesis of Intermediate 10a:

Pd/C (10%) (1.18 g) was added to a solution of 1-benzyl-4-methyl-6-(trifluoro-methyl)indoline [CAS 1156512-79-6] (11.8 g, 40.5 mmol) in AcOH (11.8 mL) and MeOH (118 mL). The reaction was stirred at room temperature for 12 h under $H_2$ atmosphere. The mixture was filtered through a pad of Celite® and concentrated under reduced pressure. The residue was taken up with $CH_2Cl_2$, washed with water, brine, dried over $MgSO_4$, filtered and concentrated under reduced pressure. The residue was purified by flash chromatography on silica gel (heptane/EtOAc 9/1). The pure fractions were combined and the solvent was evaporated to dryness to give 8.2 g of 4-methyl-6-(trifluoromethyl)indoline 10a.

Synthesis of Compound 10 and Chiral Separation into Enantiomers 10A and 10B:

A mixture of 4-methyl-6-(trifluoromethyl)indoline 10a (515 mg, 2.56 mmol), 2-(4-chlorophenyl)-2-((3-(2-hydroxyethoxy)-5-methoxyphenyl)amino)acetic acid 3f (900 mg, 2.56 mmol), diisopropylethylamine (1.27 mL, 7.67 mmol) and HATU (1.46 g, 3.84 mmol) in DMF (7 mL) was stirred at room temperature for 18 h. Water was added and the mixture was extracted with EtOAc. The organic layer was washed with water (several times), dried over $MgSO_4$, filtered and the solvent was evaporated under reduced pressure. Purification was performed by flash chromatography on silica gel, (15-40 μm, 40 g, heptane/EtOAc 50/50). This fraction was combined with another batch (total amount: 640 mg) and further purified by reverse phase chromatography (Stationary phase: X-Bridge® C18 μm 30×150 mm, Mobile phase: gradient from 60% $NH_4HCO_3$ 0.2%, 40% $CH_3CN$ to 0% $NH_4HCO_3$ 0.2%, 100% $CH_3CN$). The pure fractions were combined and evaporated to dryness, to give racemic 2-(4-chlorophenyl)-2-((3-(2-hydroxy-ethoxy)-5-methoxyphenyl)amino)-1-(4-methyl-6-(trifluoromethyl)indolin-1-yl)-ethanone (Compound 10, 425 mg). The enantiomers of Compound 10 were separated via Preparative Chiral SFC (Stationary phase: Chiralpak© IA 5 μm 250×20 mm, Mobile phase: 50% $CO_2$, 50% EtOH (+0.3% $iPrNH_2$)). The first eluted enantiomer (180 mg) was solidified from heptane/diisopropyl ether to afford Enantiomer 10A (145 mg). The second eluted enantiomer (170 mg) was solidified from heptane/diisopropyl ether to afford Enantiomer 10B (113 mg).

Enantiomer 10A:

$^1$H NMR (500 MHz, DMSO-$d_6$) δ ppm 2.25 (s, 3H) 3.05-3.24 (m, 2H) 3.60-3.68 (m, 5H) 3.80-3.90 (m, 2H) 4.04 (td, J=10.6, 6.9 Hz, 1H) 4.54 (td, J=10.5, 6.1 Hz, 1H) 4.78 (t, J=5.5 Hz, 1H) 5.57 (d, J=8.5 Hz, 1H) 5.76 (t, J=2.0 Hz, 1H) 5.95 (d, J=0.9 Hz, 2H) 6.42 (d, J=8.5 Hz, 1H) 7.25 (s, 1H) 7.44 (d, J=8.5 Hz, 2H) 7.56 (d, J=8.5 Hz, 2H) 8.23 (s, 1H)

LC/MS (method LC-A): $R_t$ 3.43 min, MH$^+$ 535

$[α]_D^{20}$: −46.2° (c 0.2275, DMF)

Chiral SFC (method SFC-1): $R_t$ 2.26 min, MH$^+$ 535, chiral purity 100%.

Enantiomer 10B:

$^1$H NMR (500 MHz, DMSO-$d_6$) δ ppm 2.25 (s, 3H) 3.05-3.24 (m, 2H) 3.59-3.68 (m, 5H) 3.80-3.91 (m, 2H) 4.04 (td, J=10.5, 7.1 Hz, 1H) 4.54 (td, J=10.4, 6.3 Hz, 1H) 4.78 (t, J=5.5 Hz, 1H) 5.57 (d, J=8.5 Hz, 1H) 5.76 (t, J=2.0 Hz, 1H) 5.95 (d, J=0.9 Hz, 2H) 6.42 (d, J=8.8 Hz, 1H) 7.25 (s, 1H) 7.44 (d, J=8.5 Hz, 2H) 7.56 (d, J=8.2 Hz, 2H) 8.23 (s, 1H)

LC/MS (method LC-A): $R_t$ 3.43 min, MH$^+$ 535

$[α]_D^{20}$: +43.0° (c 0.2092, DMF)

Chiral SFC (method SFC-1): $R_t$ 3.61 min. MH$^+$ 535, chiral purity 100%.

Example 11: Synthesis of 2-(4-chloro-2-methoxyphenyl)-2-((3-(2-hydroxyethoxy)-5-methoxyphenyl)amino)-1-(5-methoxy-6-(trifluoromethyl)indolin-1-yl)ethanone (Compound 11) and Chiral Separation into Enantiomers 11A and 11B

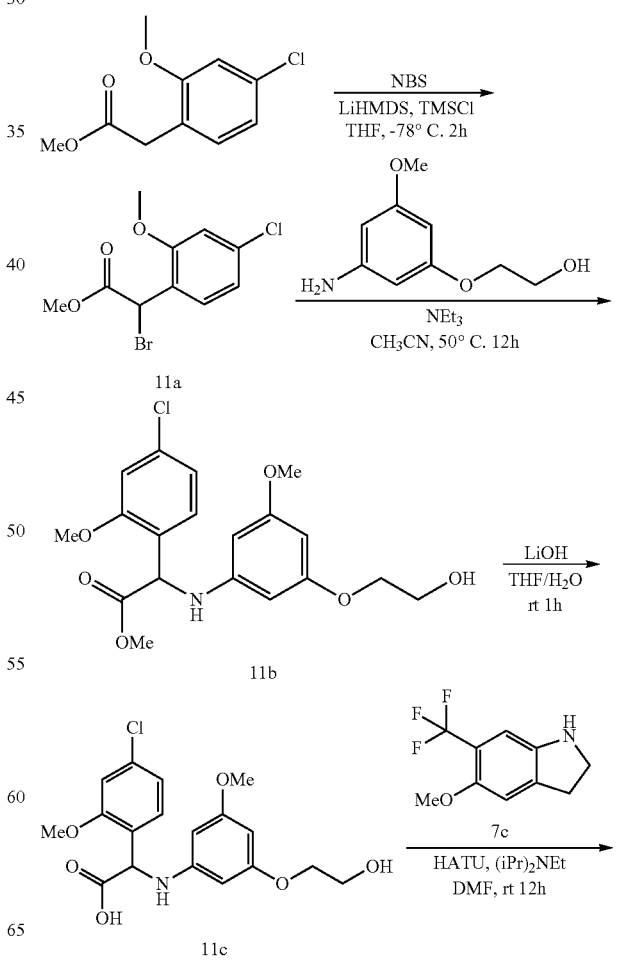

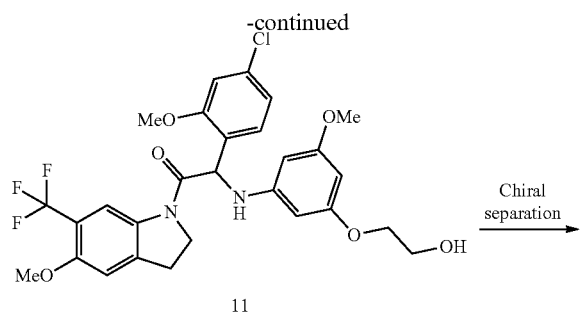

Synthesis of Intermediate 11a:

At −78° C., under a N₂ flow, LiHMDS 1.5 M in THF (6.2 mL, 9.32 mmol) was added dropwise to a mixture of methyl 2-(4-chloro-2-methoxyphenyl)acetate [CAS 193290-23-2] (1 g, 4.66 mmol) in THF (30 mL). A solution of TMSCl (0.95 mL, 7.45 mmol) in THF (10 mL) was added dropwise. The mixture was stirred for 15 min at −78° C. and NBS (0.912 g, 5.13 mmol) in THF (10 mL) was added dropwise. After stirring for 2 h at −78° C., the reaction was quenched with a saturated solution of NH₄Cl. The mixture was extracted with EtOAc, dried over MgSO₄, filtered and the solvent was evaporated under reduced pressure to give methyl 2-bromo-2-(4-chloro-2-methoxyphenyl)acetate 11a (1.4 g). The compound was used as such in the next step.

Synthesis of Intermediate 11b:

A mixture of methyl 2-bromo-2-(4-chloro-2-methoxyphenyl)acetate 11a (0.5 g, 1.71 mmol), 2-(3-amino-5-methoxyphenoxy)ethanol [CAS 725237-16-1] (328 mg, 1.79 mmol), trimethylamine (355 µL, 2.56 mmol) in CH₃CN (10 mL) was stirred at 50° C. for 12 h. The mixture was diluted with EtOAc and washed with water. The organic phase was separated, dried over MgSO₄, filtered and the solvent was evaporated under reduced pressure. The residue was purified by flash chromatography on silica gel (15-40 µm, 40 g, CH₂Cl₂/MeOH 99/1). The pure fractions were combined and evaporated to dryness to give methyl 2-(4-chloro-2-methoxyphenyl)-2-((3-(2-hydroxyethoxy)-5-methoxyphenyl)amino)acetate 11b (510 mg).

Synthesis of Intermediate 11c:

Methyl 2-(4-chloro-2-methoxyphenyl)-2-((3-(2-hydroxyethoxy)-5-methoxyphenyl)-amino)acetate 11b (1.2 g, 3.03 mmol) and LiOH (382 mg, 9.10 mmol) in THF/water (1/1) (20 mL) was stirred at room temperature for 1 h. The mixture was diluted with water. The aqueous layer was slowly acidified with 3N HCl and extracted with EtOAc. The combined organic layers were dried over MgSO₄, filtered and the solvent was evaporated under reduced pressure to give 2-(4-chloro-2-methoxyphenyl)-2-((3-(2-hydroxyethoxy)-5-methoxyphenyl)amino)acetic acid 11c (1.12 g). The compound was used as such in the next step.

Synthesis of Compound 11 and Chiral Separation into Enantiomers 11A and 11B:

HATU (0.692 g, 1.82 mmol) was added to a mixture of 5-methoxy-6-(trifluoro-methyl)indoline 7c (264 mg, 1.21 mmol), 2-(4-chloro-2-methoxyphenyl)-2-((3-(2-hydroxyethoxy)-5-methoxyphenyl)amino)acetic acid 11c (520 mg, 1.36 mmol) and diisopropylethylamine (0.602 mL, 3.64 mmol) in DMF (14 mL). The resulting mixture was stirred at room temperature for 12 h. The mixture was diluted with water and EtOAc. The organic layer was separated, washed with a 10% solution of K₂CO₃ in water and then with brine.

The organic layer was dried over MgSO₄, filtered and the solvent was evaporated under reduced pressure. The crude product was purified by flash chromatography on silica gel (15-40 µm, 40 g, CH₂Cl₂/MeOH 99.5/0.5). The pure fraction were combined and evaporated to dryness to afford racemic 2-(4-chloro-2-methoxyphenyl)-2-((3-(2-hydroxyethoxy)-5-methoxyphenyl)amino)-1-(5-methoxy-6-(trifluoromethyl)indolin-1-yl)ethanone (Compound 11, 398 mg). This batch was combined with another batch (total amount: 535 mg). The enantiomers were separated via Preparative Chiral SFC (Stationary phase: Chiralpak® IA 5 µm 250×20 mm, Mobile phase: 70% CO₂, 30% iPrOH (+0.3% iPrNH₂)). The first eluted enantiomer (240 mg) was crystallized from CH₃CN/diisopropyl ether to give Enantiomer 11A (194 mg). The second eluted enantiomer (240 mg) was crystallized from CH₃CN/diisopropyl ether to give Enantiomer 11B (189 mg).

Compound 11:

¹H NMR (500 MHz, DMSO-d₆) δ ppm 3.19-3.29 (m, 2H) 3.59-3.69 (m, 5H) 3.78-3.88 (m, 5H) 3.91 (s, 3H) 3.95-4.04 (m, 1H) 4.31-4.41 (m, 1H) 4.80 (t, J=5.4 Hz, 1H) 5.59 (br d, J=8.5 Hz, 1H) 5.73-5.78 (m, 1H) 5.87 (br s, 2H) 6.41 (br d, J=8.5 Hz, 1H) 7.03 (dd, J=8.2, 1.3 Hz, 1H) 7.15 (d, J=1.3 Hz, 1H) 7.25 (s, 1H) 7.33 (d, J=8.2 Hz, 1H) 8.33 (s, 1H)

LC/MS (method LC-A): $R_t$ 3.22 min, MH⁺ 581

Melting point: 224° C.

Enantiomer 11A:

¹H NMR (500 MHz, DMSO-d₆) δ ppm 3.16-3.30 (m, 2H) 3.60-3.68 (m, 5H) 3.77-3.88 (m, 5H) 3.90 (s, 3H) 3.99 (td, J=10.2, 7.3 Hz, 1H) 4.35 (td, J=10.2, 6.6 Hz, 1H) 4.79 (t, J=5.5 Hz, 1H) 5.58 (d, J=8.5 Hz, 1H) 5.73-5.78 (m, 1H) 5.87 (s, 2H) 6.41 (d, J=8.8 Hz, 1H) 7.02 (dd, J=8.2, 1.9 Hz, 1H) 7.14 (d, J=1.9 Hz, 1H) 7.24 (s, 1H) 7.32 (d, J=8.5 Hz, 1H) 8.33 (s, 1H)

LC/MS (method LC-A): $R_t$ 3.25 min, MH⁺ 581

[α]D20: −31.4° (c 0.274, DMF)

Chiral SFC (method SFC-H): $R_t$ 3.60 min, MH⁺ 581, chiral purity 100%.

Melting point: 175° C.

Enantiomer 11B:

¹H NMR (500 MHz, DMSO-d₆) δ ppm 3.17-3.30 (m, 2H) 3.59-3.68 (m, 5H) 3.78-3.88 (m, 5H) 3.91 (s, 3H) 3.99 (td, J=10.2, 7.3 Hz, 1H) 4.35 (td, J=10.2, 6.6 Hz, 1H) 4.79 (t, J=5.5 Hz, 1H) 5.58 (d, J=8.5 Hz, 1H) 5.73-5.78 (m, 1H) 5.87 (s, 2H) 6.41 (d, J=8.8 Hz, 1H) 7.02 (dd, J=8.2, 1.9 Hz, 1H) 7.14 (d, J=1.9 Hz, 1H) 7.24 (s, 1H) 7.32 (d, J=8.2 Hz, 1H) 8.33 (s, 1H)

LC/MS (method LC-A): $R_t$ 3.25 min, MH⁺ 581

[α]D20: +29.4° (c 0.272, DMF)

Chiral SFC (method SFC-H): $R_t$ 4.96 min, MH⁺ 581, chiral purity 100%.

Melting point: 175° C.

Example 12: Synthesis of 2-(4-chlorophenyl)-1-(5-fluoro-6-(trifluoromethyl)indolin-1-yl)-2-((3-(2-hydroxyethoxy)-5-methoxyphenyl)amino)ethanone (Compound 12) and Chiral Separation into Enantiomers 12A and 12B

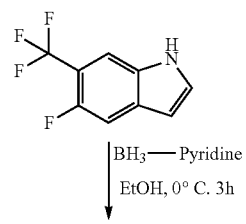

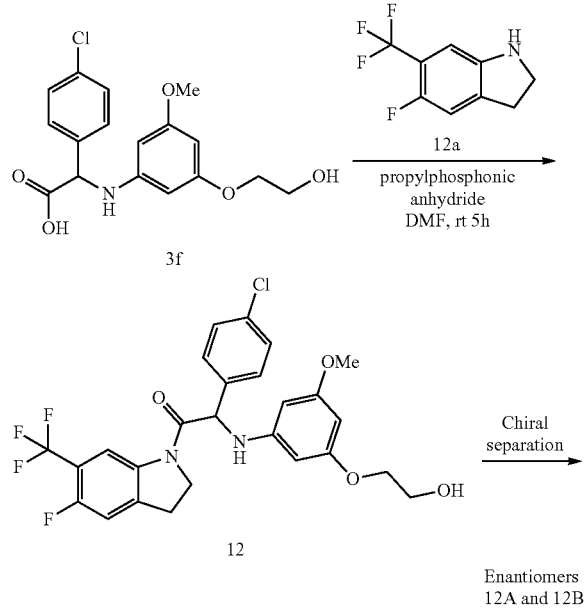

Synthesis of Intermediate 12a:

At 0° C., BH₃—Pyridine (10.5 mL, 103.5 mmol) was added dropwise to a solution of 5-fluoro-6-(trifluoromethyl)-1H-indole [CAS 1493800-10-4] (7 g, 34.5 mmol) in EtOH (45 mL). 6N HCl (105 mL) was slowly added dropwise while maintaining the reaction temperature below 10° C. The mixture was stirred at 0° C. for 3 h. Water (210 mL) was added and the mixture was basified until pH 8-9 with a concentrated solution of NaOH in water (the reaction temperature was kept below 20° C.). The mixture was extracted with EtOAc. The organic layer was washed with water, dried over MgSO₄, filtered and the solvent was evaporated under reduced pressure. Toluene was added and the solution was concentrated under reduced pressure. Purification was performed by flash chromatography on silica gel, (15-40 μm, 120 g, heptane/EtOAc 85/15). The pure fractions were combined and evaporated to dryness to give 3.5 g of 5-fluoro-6-(trifluoromethyl)indoline 12a.

Synthesis of Compound 12 and Chiral Separation into Enantiomers 12A and 12B:

Under N₂ flow, at 5° C., propylphosphonic anhydride (1.76 mL, 2.93 mmol) was added dropwise to a mixture of 5-fluoro-6-(trifluoromethyl)indoline 12a (400 mg, 1.95 mmol), 2-(4-chlorophenyl)-2-((3-(2-hydroxyethoxy)-5-methoxyphenyl)-amino)acetic acid 3f (823 mg, 2.34 mmol) and diisopropylethylamine (709 μL, 4.29 mmol) in DMF (30 mL). The mixture was stirred at room temperature for 5 h. Water was added and the precipitate was filtered off and washed with a 10% solution of K₂CO₃ in water. The solid was taken up with EtOAc. The organic layer was washed with water, dried over MgSO₄, filtered and the solvent was evaporated under reduced pressure. Purification was performed by flash chromatography on silica gel, (15-40 μm, 40 g, CH₂Cl₂/MeOH 99.5/0.5). The pure fractions were combined and evaporated to dryness, to give racemic 2-(4-chloro-phenyl)-1-(5-fluoro-6-(trifluoromethyl)indolin-1-yl)-2-((3-(2-hydroxyethoxy)-5-methoxyphenyl)amino) ethanone (Compound 12, 825 mg). Crystallization from CH₃CN/diisopropyl ether afforded Compound 12 (448 mg) as a crystalline fraction. The enantiomers of Compound 12 were separated via Preparative Chiral SFC (Stationary phase: Chiralcel® OJ-H 5 μm 250×20 mm, Mobile phase: 60% CO₂, 40% EtOH (+0.3% iPrNH₂)). The first eluted enantiomer (193 mg) was solidified from heptane/diisopropyl ether to give Enantiomer 12A (164 mg). The second eluted enantiomer (190 mg) was solidified from heptane/diisopropyl ether to give Enantiomer 12B (131 mg).

Compound 12:
¹H NMR (500 MHz, DMSO-d₆) δ ppm 3.18-3.31 (m, 2H) 3.62 (s, 3H) 3.63-3.67 (m, 2H) 3.80-3.89 (m, 2H) 4.03 (td, J=10.3, 7.4 Hz, 1H) 4.54 (td, J=10.2, 6.3 Hz, 1H) 4.79 (br t, J=5.0 Hz, 1H) 5.57 (d, J=8.5 Hz, 1H) 5.76 (s, 1H) 5.94 (s, 2H) 6.44 (d, J=8.8 Hz, 1H) 7.42-7.48 (m, 3H) 7.55 (d, J=8.2 Hz, 2H) 8.39 (d, J=6.6 Hz, 1H)

LC/MS (method LC-A): $R_t$ 3.37 min, MH⁺ 539

Melting point: 130° C.

Enantiomer 12A:
¹H NMR (500 MHz, DMSO-d₆) δ ppm 3.17-3.32 (m, 2H) 3.62 (s, 3H) 3.64 (q, J=5.6 Hz, 2H) 3.79-3.90 (m, 2H) 4.03 (td, J=10.2, 7.3 Hz, 1H) 4.54 (td, J=10.4, 6.3 Hz, 1H) 4.79 (t, J=5.5 Hz, 1H) 5.57 (d, J=8.5 Hz, 1H) 5.76 (s, 1H) 5.94 (s, 2H) 6.44 (d, J=8.8 Hz, 1H) 7.41-7.48 (m, 3H) 7.55 (d, J=8.5 Hz, 2H) 8.39 (d, J=6.3 Hz, 1H)

LC/MS (method LC-A): $R_t$ 3.37 min, MH⁺ 539

[α]D20: +50.2° (c 0.299, DMF)

Chiral SFC (method SFC-D): $R_t$ 1.91 min, MH⁺ 539, chiral purity 100%.

Enantiomer 12B:
¹H NMR (500 MHz, DMSO-d₆) δ ppm 3.18-3.32 (m, 2H) 3.62 (s, 3H) 3.65 (q, J=5.3 Hz, 2H) 3.78-3.90 (m, 2H) 4.03 (td, J=10.2, 7.3 Hz, 1H) 4.54 (td, J=10.2, 6.3 Hz, 1H) 4.79 (t, J=5.4 Hz, 1H) 5.57 (d, J=8.8 Hz, 1H) 5.76 (s, 1H) 5.94 (s, 2H) 6.44 (d, J=8.5 Hz, 1H) 7.41-7.49 (m, 3H) 7.55 (d, J=8.2 Hz, 2H) 8.39 (d, J=6.6 Hz, 1H)

LC/MS (method LC-A): $R_t$ 3.38 min. MH⁺ 539

$[α]_D^{20}$: −51.0° (c 0.3, DMF)

Chiral SFC (method SFC-D): $R_t$ 3.93 min, MH⁺ 539, chiral purity 99.52%.

Example 13: Synthesis of 2-(4-chlorophenyl)-2-((3-(2-hydroxyethoxy)-5-methoxy-phenyl)amino)-1-(5-methoxy-6-(trifluoromethoxy)indolin-1-yl)ethanone (Compound 13) and Chiral Separation into Enantiomers 13A and 13B

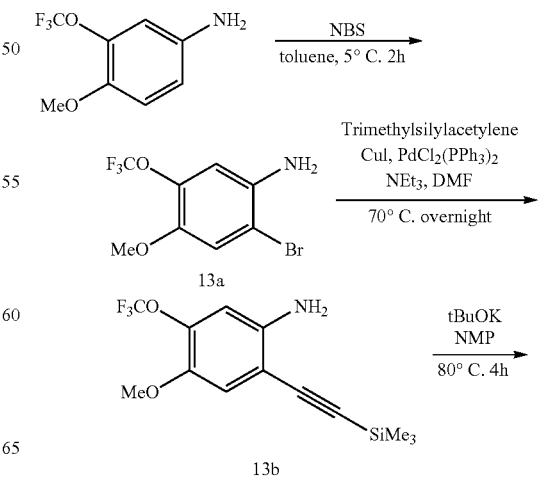

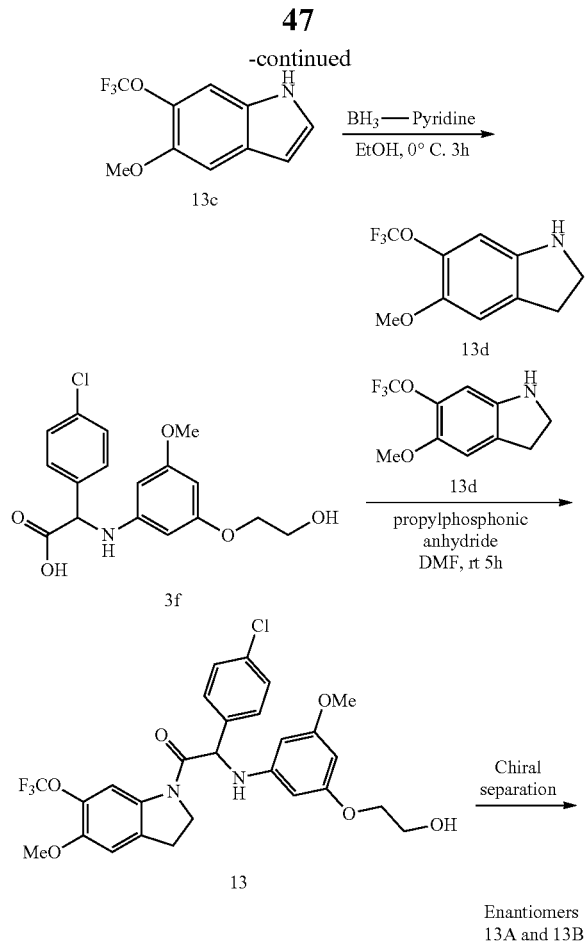

Synthesis of Intermediate 13c:

To a solution of 4-methoxy-5-(trifluoromethoxy)-2-((trimethylsilyl)ethynyl)aniline 13b (1.2 g, 3.96 mmol) in NMP (11 mL) under $N_2$ flow, was added tBuOK (1.33 g, 11.9 mmol) in one portion. The reaction mixture was heated at 80° C. for 4 h, then poured out into ice/water and acidified with 3N HCl until pH 4-5. The reaction mixture was extracted with EtOAc. The organic phases were combined, washed with $H_2O$, dried over $MgSO_4$, filtered and concentrated under reduced pressure. The residue was purified by flash chromatography on silica gel (15-40 μm, 40 g, heptane/EtOAc 85/15). The pure fractions were combined and evaporated to dryness to give 5-methoxy-6-(trifluoromethoxy)-1H-indole 13c (490 mg).

Synthesis of Intermediate 13d:

At 0° C., $BH_3$—Pyridine (10.5 mL, 103.82 mmol) was added dropwise to a solution of 5-methoxy-6-(trifluoromethoxy)-1H-indole 13c (8 g, 34.6 mmol) in EtOH (45 mL). 6N HCl (6 mL) was slowly added dropwise while maintaining the temperature below 10° C. The mixture was stirred at 0° C. for 3 h. Water (210 mL) was added and the mixture was basified until pH 8-9 with a concentrated solution of NaOH in water (the reaction temperature was kept below 20° C.). The mixture was extracted with EtOAc. The organic layer was washed with water, dried over $MgSO_4$, filtered and the solvent was evaporated under reduced pressure. Toluene was added and the solution was concentrated under reduced pressure to give 7.5 g of 5-methoxy-6-(trifluoromethoxy)indoline 13d.

Synthesis of Compound 13 and Chiral Separation into Enantiomers 13A and 13B:

Under $N_2$ flow at 5° C., propylphosphonic anhydride (2.1 mL, 3.35 mmol) was added dropwise to a mixture of 5-methoxy-6-(trifluoromethoxy)indoline 13d (552 mg, 2.37 mmol), 2-(4-chlorophenyl)-2-((3-(2-hydroxyethoxy)-5-methoxy-phenyl)amino)acetic acid 3f (1 g, 2.84 mmol) and diisopropylethylamine (861 μL, 5.21 mmol) in DMF (40 mL). The mixture was stirred at room temperature for 5 h. Water was added and the precipitate was filtered off and washed with a 10% solution of $K_2CO_3$ in water. The solid was taken up with EtOAc. The organic layer was washed with water, dried over $MgSO_4$, filtered and the solvent was evaporated under reduced pressure. Purification was performed by flash chromatography on silica gel, (15-40 μm, 40 g, $CH_2Cl_2$/MeOH 99.5/0.5). Pure fractions were combined and evaporated to dryness, to give, after crystallization from diisopropyl ether, racemic 2-(4-chlorophenyl)-2-((3-(2-hydroxyethoxy)-5-methoxyphenyl)amino)-1-(5-methoxy-6-(trifluoromethoxy)indolin-1-yl)ethanone (Compound 13, 970 mg). The enantiomers of Compound 13 were separated via Preparative Chiral SFC (Stationary phase: Chiralpak® IC 5 μm 250×30 mm, Mobile phase: 55% $CO_2$, 45% EtOH (+0.3% $iPrNH_2$)). The first eluted enantiomer (400 mg) was solidified from heptane/diisopropyl ether to give Enantiomer 13A (332 mg). The second eluted enantiomer (397 mg) was solidified from heptane/diisopropyl ether to give Enantiomer 13B (344 mg).

Compound 13:

$^1$H NMR (500 MHz, DMSO-$d_6$) δ ppm 3.10-3.26 (m, 2H) 3.62 (s, 3H) 3.65 (q, J=5.4 Hz, 2H) 3.81 (s, 3H) 3.82-3.88 (m, 2H) 4.03 (td, J=10.3, 7.1 Hz, 1H) 4.49 (td, J=10.3, 6.5 Hz, 1H) 4.80 (t, J=5.4 Hz, 1H) 5.53 (d, J=8.8 Hz, 1H) 5.75 (s, 1H) 5.94 (d, J=1.6 Hz, 2H) 6.45 (d, J=8.5 Hz, 1H) 7.20 (s, 1H) 7.44 (d, J=8.2 Hz, 2H) 7.55 (d, J=8.5 Hz, 2H) 8.06 (s, 1H)

LC/MS (method LC-A): $R_t$ 3.30 min, MH$^+$ 567

Melting point: 165° C.

Enantiomer 13A:

¹H NMR (500 MHz, DMSO-d₆) δ ppm 3.10-3.26 (m, 2H) 3.62 (s, 3H) 3.65 (q, J=5.4 Hz, 2H) 3.81 (s, 3H) 3.82-3.88 (m, 2H) 4.03 (td, J=10.3, 7.1 Hz, 1H) 4.49 (td, J=10.3, 6.5 Hz, 1H) 4.80 (t, J=5.4 Hz, 1H) 5.53 (d, J=8.8 Hz, 1H) 5.75 (s, 1H) 5.94 (d, J=1.6 Hz, 2H) 6.45 (d, J=8.5 Hz, 1H) 7.20 (s, 1H) 7.44 (d, J=8.2 Hz, 2H) 7.55 (d, J=8.5 Hz, 2H) 8.06 (s, 1H)

LC/MS (method LC-A): $R_t$ 3.31 min, MH⁺ 567

[α]D20: +43.2° (c 0.285, DMF)

Chiral SFC (method SFC-J): $R_t$ 1.82 min, MH⁺ 567, chiral purity 100%.

Enantiomer 13B:

¹H NMR (500 MHz, DMSO-d₆) δ ppm 3.09-3.26 (m, 2H) 3.61 (s, 3H) 3.64 (q, J=5.3 Hz, 2H) 3.81 (s, 3H) 3.82-3.88 (m, 2H) 4.02 (td, J=10.4, 6.9 Hz, 1H) 4.48 (td, J=10.3, 6.1 Hz, 1H) 4.79 (t, J=5.5 Hz, 1H) 5.53 (d, J=8.5 Hz, 1H) 5.75 (s, 1H) 5.94 (d, J=1.6 Hz, 2H) 6.44 (d, J=8.5 Hz, 1H) 7.20 (s, 1H) 7.43 (d, J=8.2 Hz, 2H) 7.55 (d, J=8.5 Hz, 2H) 8.06 (s, 1H)

LC/MS (method LC-A): $R_t$ 3.31 min MH⁺ 567

$[α]_D^{20}$: −45.90 (c 0.301, DMF)

Chiral SFC (method SFC-J): $R_t$ 3.15 min MH⁺ 567, chiral purity 98.96%.

TABLE

| Compound | Structure | Optical rotation |
|---|---|---|
| 1 | 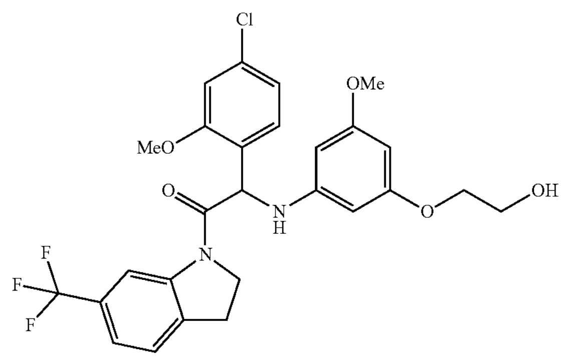 [SMILES: COc1cc(NC(C(=O)N2CCc3ccc(C(F)(F)F)cc32)c2ccc(Cl)cc2OC)cc(OCCO)c1] | racemic |
| 1A | 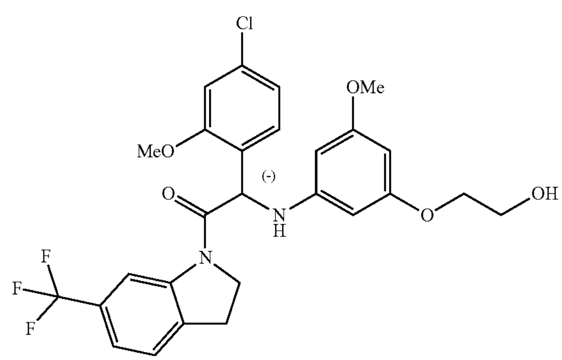 [SMILES: COc1cc(NC(C(=O)N2CCc3ccc(C(F)(F)F)cc32)c2ccc(Cl)cc2OC)cc(OCCO)c1] | $[α]_D^{20}$ = −26.5° |
| 1B | | $[α]_D^{20}$ = +28.8° | compounds prepared as described above

TABLE-continued
compounds prepared as described above
| Compound | Structure | Optical rotation |
|---|---|---|
| 2 | 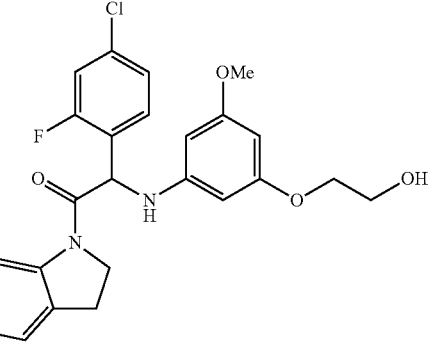 | racemic |
| 2A | 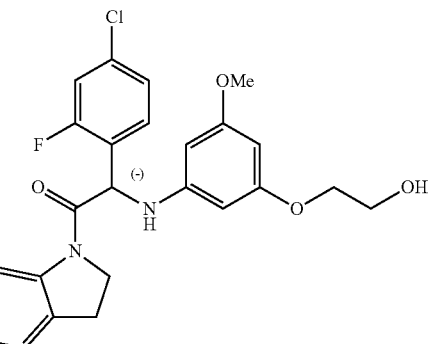 | $[\alpha]_D^{20} = -26.4°$ |
| 2B | 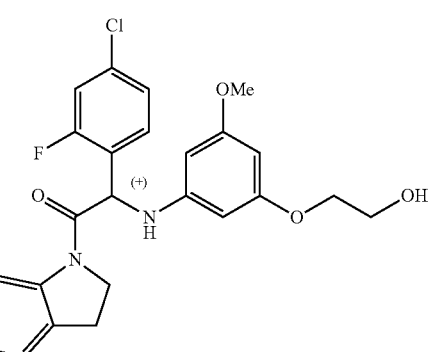 | $[\alpha]_D^{20} = +27.3°$ |
| 3 | 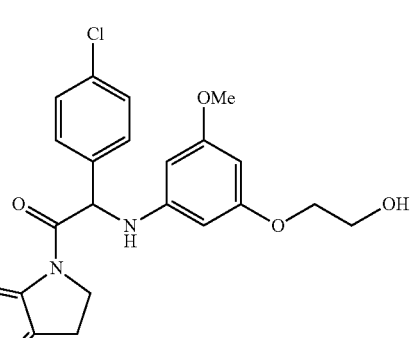 | racemic |

TABLE-continued compounds prepared as described above

| Compound | Structure | Optical rotation |
|---|---|---|
| 3A | 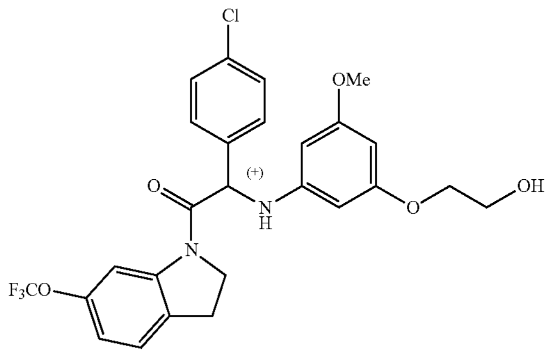 [SMILES: COc1cc(NC(C(=O)N2CCc3ccc(OC(F)(F)F)cc32)c2ccc(Cl)cc2)cc(OCCO)c1] | $[\alpha]_D^{20} = +51.9°$ |
| 3B | 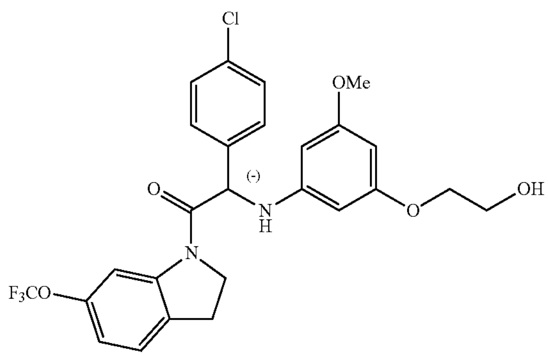 [SMILES: COc1cc(NC(C(=O)N2CCc3ccc(OC(F)(F)F)cc32)c2ccc(Cl)cc2)cc(OCCO)c1] | $[\alpha]_D^{20} = -51.1°$ |
| 4 | 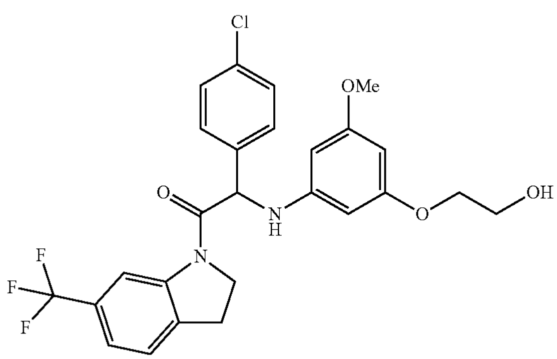 [SMILES: COc1cc(NC(C(=O)N2CCc3ccc(C(F)(F)F)cc32)c2ccc(Cl)cc2)cc(OCCO)c1] | racemic |
| 4A | 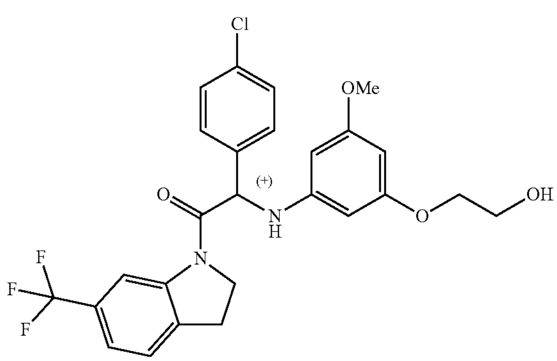 [SMILES: COc1cc(NC(C(=O)N2CCc3ccc(C(F)(F)F)cc32)c2ccc(Cl)cc2)cc(OCCO)c1] | $[\alpha]_D^{20} = +52.0°$ |

TABLE-continued compounds prepared as described above

| Compound | Structure | Optical rotation |
| --- | --- | --- |
| 4B | (structure) | $[\alpha]_D^{20} = -51.8°$ |
| 5 | (structure) | racemic |
| 5A | (structure) | $[\alpha]_D^{20} = +31.1°$ |
| 5B | (structure) | $[\alpha]_D^{20} = -31.0°$ |

TABLE-continued compounds prepared as described above

| Compound | Structure | Optical rotation |
| --- | --- | --- |
| 6 | 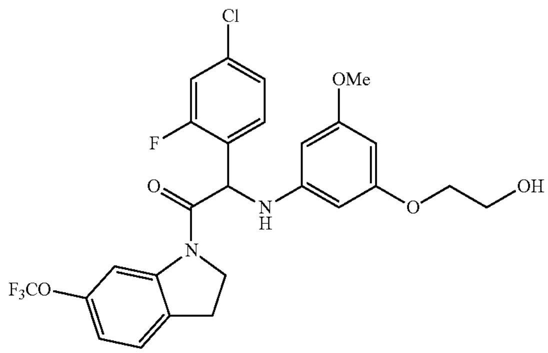 [SMILES: COc1cc(NC(C(=O)N2CCc3ccc(OC(F)(F)F)cc32)c2ccc(Cl)cc2F)cc(OCCO)c1] | racemic |
| 6A | 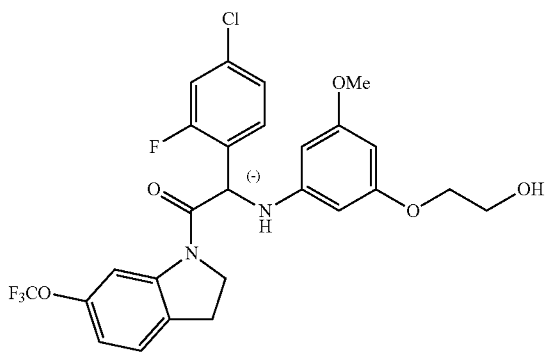 [SMILES: COc1cc(NC(C(=O)N2CCc3ccc(OC(F)(F)F)cc32)c2ccc(Cl)cc2F)cc(OCCO)c1] | $[\alpha]_D^{20} = -25.9°$ |
| 6B | 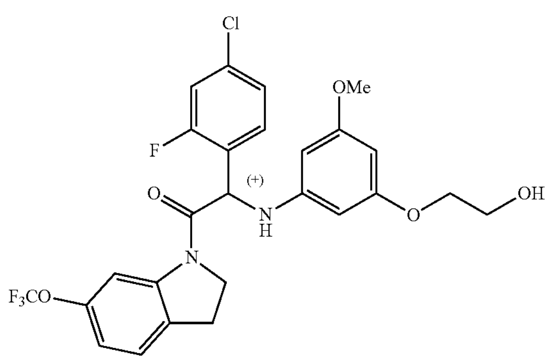 [SMILES: COc1cc(NC(C(=O)N2CCc3ccc(OC(F)(F)F)cc32)c2ccc(Cl)cc2F)cc(OCCO)c1] | $[\alpha]_D^{20} = +23.3°$ |
| 7 | 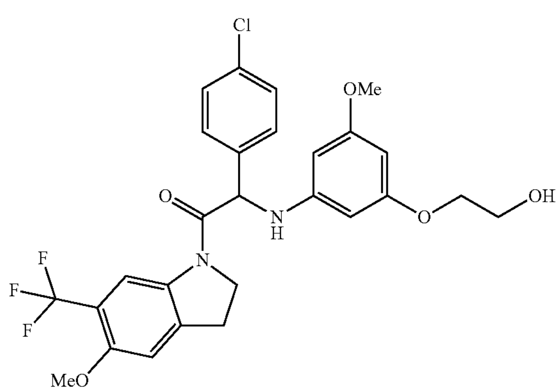 [SMILES: COc1cc(NC(C(=O)N2CCc3cc(OC)c(C(F)(F)F)cc32)c2ccc(Cl)cc2)cc(OCCO)c1] | racemic |

TABLE-continued compounds prepared as described above

| Compound | Structure | Optical rotation |
|---|---|---|
| 7A | 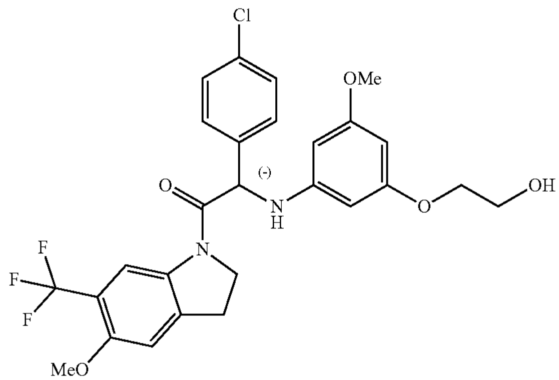 [SMILES: COc1cc(NC(C(=O)N2CCc3cc(OC)c(C(F)(F)F)cc32)c2ccc(Cl)cc2)cc(OCCO)c1] | $[\alpha]_D^{20} = -45.2°$ |
| 7B | 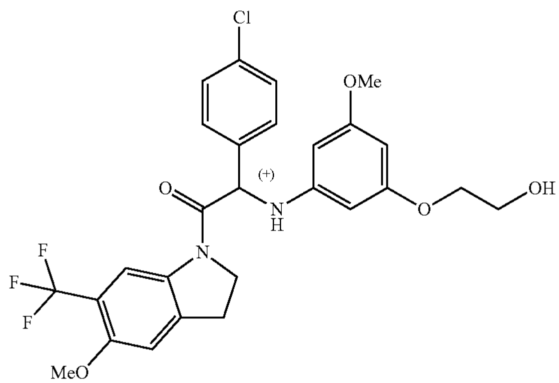 [SMILES: COc1cc(NC(C(=O)N2CCc3cc(OC)c(C(F)(F)F)cc32)c2ccc(Cl)cc2)cc(OCCO)c1] | $[\alpha]_D^{20} = +43.8°$ |
| 8 | 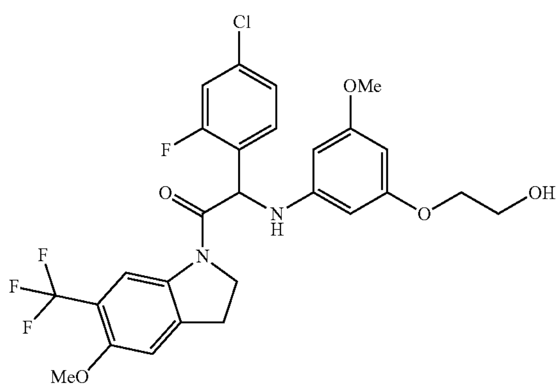 [SMILES: COc1cc(NC(C(=O)N2CCc3cc(OC)c(C(F)(F)F)cc32)c2ccc(Cl)cc2F)cc(OCCO)c1] | racemic |
| 8A | 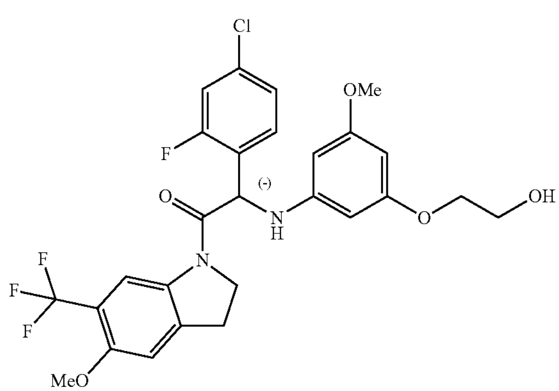 [SMILES: COc1cc(NC(C(=O)N2CCc3cc(OC)c(C(F)(F)F)cc32)c2ccc(Cl)cc2F)cc(OCCO)c1] | $[\alpha]_D^{20} = -28.9°$ |

TABLE-continued compounds prepared as described above

| Compound | Structure | Optical rotation |
|---|---|---|
| 8B | 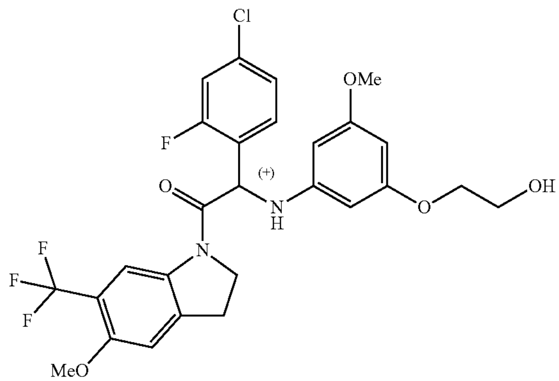 [SMILES: COc1cc(NC(C(=O)N2CCc3cc(OC)c(C(F)(F)F)cc32)c2ccc(Cl)cc2F)cc(OCCO)c1] | $[\alpha]_D^{20} = +25.7°$ |
| 9 | 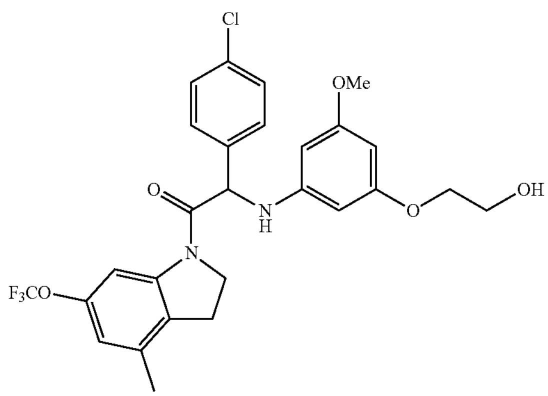 [SMILES: COc1cc(NC(C(=O)N2CCc3c(C)cc(OC(F)(F)F)cc32)c2ccc(Cl)cc2)cc(OCCO)c1] | racemic |
| 9A | 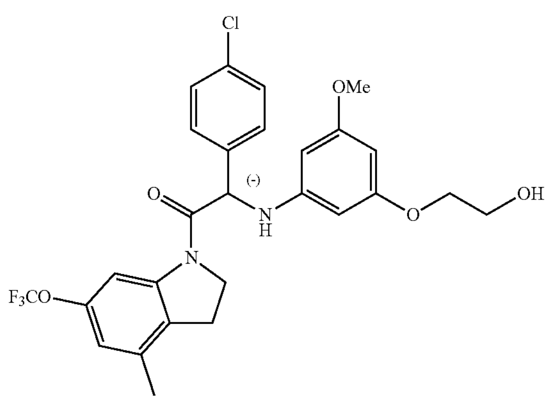 [SMILES: COc1cc(NC(C(=O)N2CCc3c(C)cc(OC(F)(F)F)cc32)c2ccc(Cl)cc2)cc(OCCO)c1] | $[\alpha]_D^{20} = -40.6°$ |
| 9B | 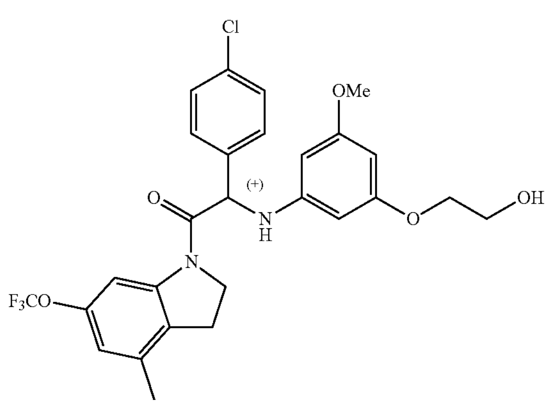 [SMILES: COc1cc(NC(C(=O)N2CCc3c(C)cc(OC(F)(F)F)cc32)c2ccc(Cl)cc2)cc(OCCO)c1] | $[\alpha]_D^{20} = +42.6°$ |

TABLE-continued compounds prepared as described above

| Compound | Structure | Optical rotation |
|---|---|---|
| 10 | 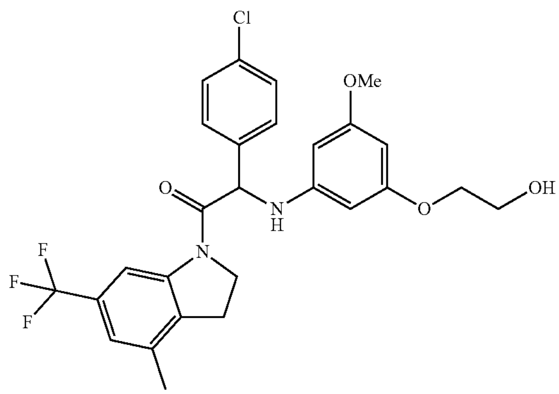 [SMILES: COc1cc(NC(C(=O)N2CCc3c(C)cc(C(F)(F)F)cc32)c2ccc(Cl)cc2)cc(OCCO)c1] | racemic |
| 10A | 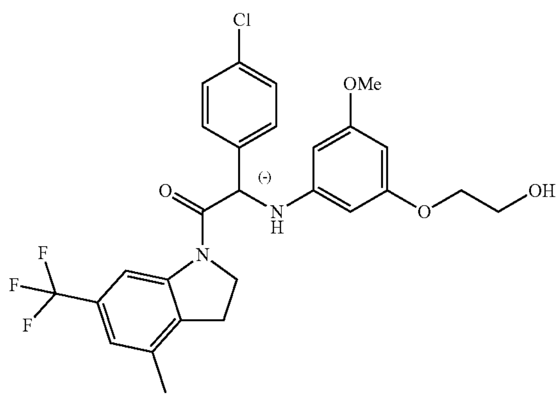 [SMILES: COc1cc(NC(C(=O)N2CCc3c(C)cc(C(F)(F)F)cc32)c2ccc(Cl)cc2)cc(OCCO)c1] | $[\alpha]_D^{20} = -46.2°$ |
| 10B | 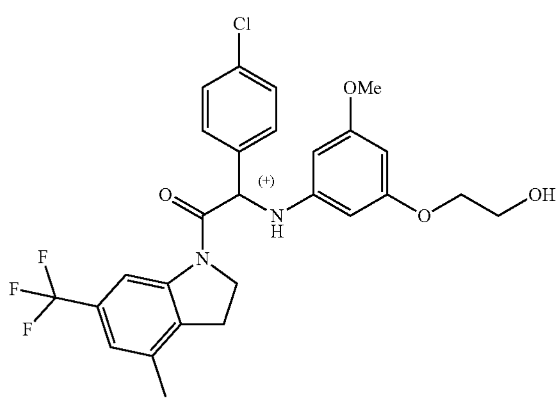 [SMILES: COc1cc(NC(C(=O)N2CCc3c(C)cc(C(F)(F)F)cc32)c2ccc(Cl)cc2)cc(OCCO)c1] | $[\alpha]_D^{20} = +43.0°$ |
| 11 | 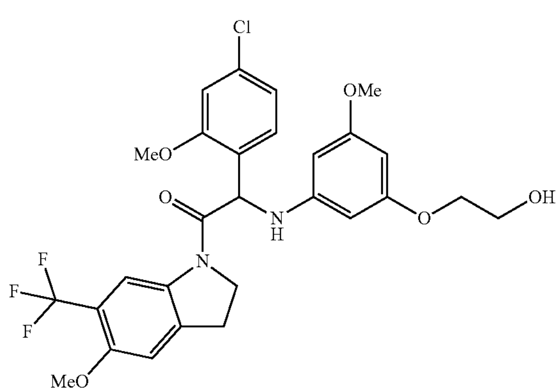 [SMILES: COc1cc(NC(C(=O)N2CCc3cc(OC)c(C(F)(F)F)cc32)c2ccc(Cl)cc2OC)cc(OCCO)c1] | racemic |

TABLE-continued compounds prepared as described above

| Compound | Structure | Optical rotation |
|---|---|---|
| 11A | 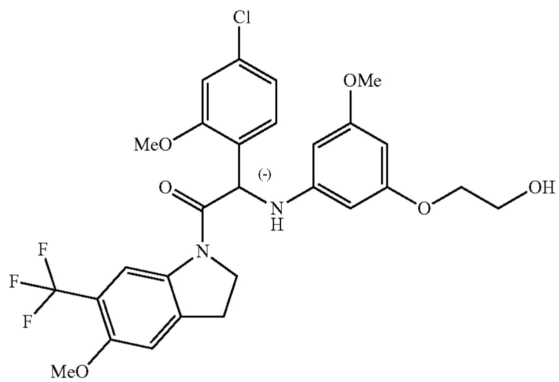 [SMILES: COc1cc(NC(C(=O)N2CCc3cc(OC)c(C(F)(F)F)cc32)c2ccc(Cl)cc2OC)cc(OCCO)c1] | $[\alpha]_D^{20} = -31.4°$ |
| 11B | 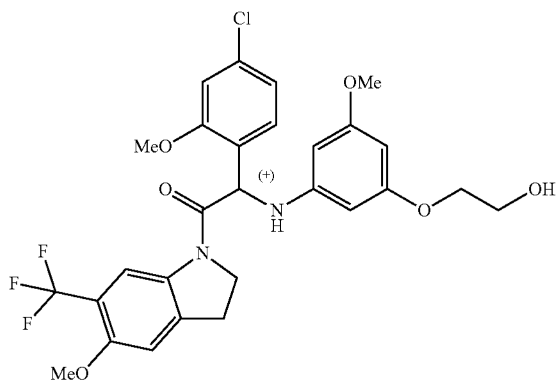 [SMILES: COc1cc(NC(C(=O)N2CCc3cc(OC)c(C(F)(F)F)cc32)c2ccc(Cl)cc2OC)cc(OCCO)c1] | $[\alpha]_D^{20} = +29.4°$ |
| 12 | 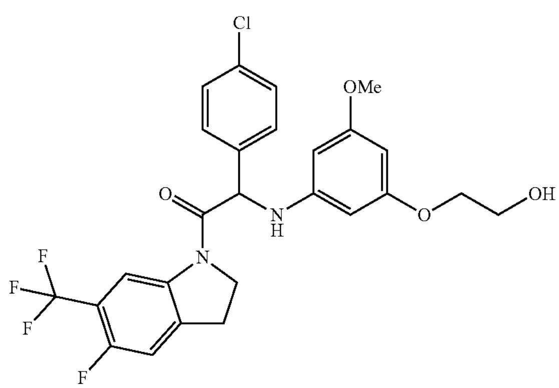 [SMILES: COc1cc(NC(C(=O)N2CCc3cc(F)c(C(F)(F)F)cc32)c2ccc(Cl)cc2)cc(OCCO)c1] | racemic |
| 12A | 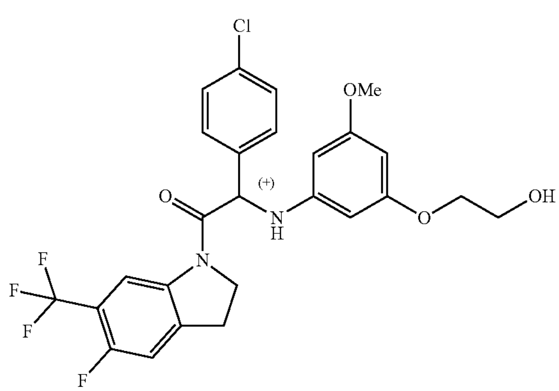 [SMILES: COc1cc(NC(C(=O)N2CCc3cc(F)c(C(F)(F)F)cc32)c2ccc(Cl)cc2)cc(OCCO)c1] | $[\alpha]_D^{20} = +50.2°$ |

TABLE-continued compounds prepared as described above

| Compound | Structure | Optical rotation |
|---|---|---|
| 12B | (structure) | $[\alpha]_D^{20} = -51.0°$ |
| 13 | (structure) | racemic |
| 13A | (structure) | $[\alpha]_D^{20} = +43.2°$ |
| 13B | (structure) | $[\alpha]_D^{20} = -45.9°$ |

Antiviral Activity of the Compounds of the Invention
DENV-2 Antiviral Assay

The antiviral activity of all the compounds of the invention was tested the against DENV-2 16681 strain which was labeled with enhanced green fluorescent protein (eGPF). The culture medium consists of minimal essential medium supplemented with 2% of heat-inactivated fetal calf serum, 0.04% gentamycin (50 mg/mL) and 2 mM of L-glutamine. Vero cells, obtained from ECACC, were suspended in culture medium and 25 μL was added to 384-well plates (2500 cells/well), which already contain the antiviral compounds. Typically, these plates contain a 5-fold serial dilution of 9 dilution steps of the test compound at 200 times the final concentration in 100% DMSO (200 nL). In addition, each compound concentration is tested in quadruplicate (final concentration range: 25 μM-0.000064 μM or 2.5 μM-0.0000064 μM for the most active compounds). Finally, each plate contains wells which are assigned as virus controls (containing cells and virus in the absence of compound), cell controls (containing cells in the absence of virus and compound) and medium controls (containing medium in the absence of cells, virus and compounds). To the wells assigned as medium control, 25 μL of culture medium was added instead of Vero cells. Once the cells were added to the plates, the plates were incubated for 30 minutes at room temperature to allow the cells to distribute evenly within the wells. Next, the plates were incubated in a fully humidified incubator (37° C., 5% $CO_2$) until the next day. Then, DENV-2 strain 16681, labeled with eGFP, was added at a multiplicity of infection (MOI) of 0.5. Therefore, 15 μL of virus suspension was added to all the wells containing test compound and to the wells assigned as virus control. In parallel, 15 μL of culture medium was added to the medium and cell controls. Next, the plates were incubated for 3 days in a fully humidified incubator (37° C., 5% $CO_2$). At the day of the read out, the eGFP fluorescence was measured using an automated fluorescence microscope at 488 nm (blue laser). Using an in-house LIMS system, inhibition dose response curves for each compound were calculated and the half maximal effective concentration ($EC_{50}$) was determined. Therefore, the percent inhibition (I) for every test concentration is calculated using the following formula: $I=100*(S_T-S_{CC})/(S_{VC}-S_{CC})$; $S_T$, $S_{CC}$ and $S_{VC}$ are the amount of eGFP signal in the test compound, cell control and virus control wells, respectively. The $EC_{50}$ represents the concentration of a compound at which the virus replication is inhibited with 50%, as measured by a 50% reduction of the eGFP fluorescent intensity compared to the virus control. The $EC_{50}$ is calculated using linear interpolation (Table 1).

In parallel, the toxicity of the compounds was assessed on the same plates. Once the read-out for the eGFP signal was done, 40 μL of ATPlite, a cell viability stain, was added to all wells of the 384-well plates. ATP is present in all metabolically active cells and the concentration declines very rapidly when the cells undergo necrosis or apoptosis. The ATPLite assay system is based on the production of light caused by the reaction of ATP with added luciferase and D-luciferin. The plates were incubated for 10 minutes at room temperature. Next, the plates were measured on a ViewLux. The half maximal cytotoxic concentration ($CC_{50}$) was also determined, defined as the concentration required to reduce the luminescent signal by 50% compared to that of the cell control wells. Finally, the selectivity index (SI) was determined for the compounds, which was calculated as followed: $SI=CC_{50}/EC_{50}$.

TABLE 1

$EC_{50}$, $CC_{50}$, and SI for the compounds of the invention in the DENV-2 antiviral assay

| compound # | $EC_{50}$ (μM) | N | $CC_{50}$ (μM) | N | SI | N |
|---|---|---|---|---|---|---|
| 1 | 0.0056 | 4 | 13 | 4 | 2070 | 4 |
| 1A | 0.22 | 3 | 13 | 3 | 50 | 3 |
| 1B | 0.0036 | 6 | 12 | 6 | 3578 | 6 |
| 2 | 0.0089 | 4 | 12 | 4 | 1400 | 4 |
| 2A | 0.32 | 3 | 18 | 3 | 46 | 3 |
| 2B | 0.0025 | 3 | 13 | 5 | 3750 | 3 |
| 3 | 0.0055 | 4 | 9.5 | 4 | 1760 | 4 |
| 3A | 0.0023 | 4 | 9.6 | 7 | 4530 | 4 |
| 3B | 0.59 | 3 | 12 | 3 | 19 | 3 |
| 4 | 0.0067 | 3 | 9.7 | 3 | 1440 | 3 |
| 4A | 0.0036 | 4 | 12 | 6 | 3878 | 4 |
| 4B | 1.1 | 3 | 14 | 3 | 11 | 3 |
| 5 | 0.0046 | 3 | 9.3 | 3 | 2040 | 3 |
| 5A | 0.0014 | 4 | 9.8 | 4 | 7000 | 4 |
| 5B | 0.76 | 3 | 14 | 4 | 19 | 3 |
| 6 | 0.0062 | 4 | 14 | 4 | 1940 | 4 |
| 6A | 0.28 | 4 | 17 | 4 | 49 | 4 |
| 6B | 0.0025 | 10 | 12 | 10 | 4900 | 10 |
| 7 | 0.0023 | 3 | 11 | 3 | 4670 | 3 |
| 7A | 0.79 | 5 | 21 | 5 | 26 | 5 |
| 7B | 0.0010 | 9 | 12 | 10 | 10000 | 9 |
| 8 | 0.0044 | 3 | >25 | 3 | >6100 | 3 |
| 8A | 0.46 | 6 | >25 | 6 | >81 | 6 |
| 8B | 0.0019 | 7 | 76 | 7 | >49900 | 7 |
| 9A | 1.0 | 3 | 13 | 3 | 12 | 3 |
| 9B | 0.0014 | 3 | 11 | 3 | 8440 | 3 |
| 10A | 1.3 | 4 | 11 | 4 | 8.4 | 4 |
| 10B | 0.0022 | 3 | 11 | 3 | 5470 | 3 |
| 11 | 0.0023 | 3 | 22 | 3 | 8650 | 3 |
| 11A | 0.33 | 3 | >25 | 3 | >94 | 3 |
| 11B | 0.0016 | 3 | >25 | 3 | >33700 | 3 |
| 12 | 0.011 | 3 | 11 | 3 | 966 | 3 |
| 12A | 0.0023 | 3 | 12 | 3 | 5020 | 3 |
| 12B | 0.40 | 3 | 11 | 3 | 27 | 3 |
| 13 | 0.0049 | 3 | 13 | 3 | 2630 | 3 |
| 13A | 0.0035 | 3 | 12 | 3 | 3970 | 3 |
| 13B | 0.28 | 3 | >25 | 3 | >123 | 3 |

N = the number of independent experiments in which the compounds were tested.

Tetravalent Reverse Transcriptase Quantitative-PCR (RT-qPCR) Assay

The antiviral activity of the compounds of the invention was tested against DEN-1 strain TC974 #666 (NCPV), DENV-2 strain 16681, DENV-3 strain H87 (NCPV) and DENV-4 strain H241 (NCPV) in a RT-qPCR assay. Therefore, Vero cells were infected with either DEN-, or -2, or -3, or -4 in the presence or absence of test compounds. At day 3 post-infection, the cells were lysed and cell lysates were used to prepare cDNA of both a viral target (the 3'UTR of DENV; Table 2) and a cellular reference gene (β-actin, Table 2). Subsequently, a duplex real time PCR was performed on a Lightcycler480 instrument. The generated Cp value is inversely proportional to the amount of RNA expression of these targets. Inhibition of DENV replication by a test compound results in a shift of Cp's for the 3'UTR gene. On the other hand, if a test compound is toxic to the cells, a similar effect on β-actin expression will be observed. The comparative ΔΔCp method is used to calculate $EC_{50}$, which is based on the relative gene expression of the target gene (3'UTR) normalized with the cellular housekeeping gene (β-actin). In addition, $CC_{50}$ values are determined based on the Cp values acquired for the housekeeping gene β-actin.

TABLE 2

Primers and probes used for the real-time, quantitative RT-PCR.

| Primer/probe | Target | Sequence[a, b] |
|---|---|---|
| F3utr258 | DENV 3'-UTR | 5'-CGGTTAGAGGAGAC CCCTC-3' |
| R3utr425 | DENV 3'-UTR | 5'-GAGACAGCAGGATC TCTGGTC-3' |
| P3utr343 | DENV 3'-UTR | *FAM*-5'-AAGGACTAG-*ZEN*-AGGTTAGAGGAGA CCCCCC-3'-*IABkFQ* |
| Factin743 | β-actin | 5'-GGCCAGGTCATCAC CATT-3' |
| Ractin876 | β-actin | 5'-ATGTCCACGTCACA CTTCATG-3' |
| Pactin773 | β-actin | *HEX*-5'-TTCCGCTGC-*ZEN*-CCTGAGGCTCTC-3'-*IABkFQ* |

[a] Reporter dyes (FAM, HEX) and quenchers (ZEN and IABkFQ) elements are indicated in bold and italics.
[b] The nucleotide sequence of the primers and probes were selected from the conserved region in the 3'UTR region of the dengue virus genome, based on the alignment of 300 nucleotide sequences of the four dengue serotypes deposited in Genbank (Gong et al., 2013, Methods Mol Biol, Chapter 16).

The culture medium consisted of minimal essential medium supplemented with 2% of heat-inactivated fetal calf serum, 0.04% gentamycin (50 mg/mL) and 2 mM of L-glutamine. Vero cells, obtained from ECACC, were suspended in culture medium and 75 μL/well was added in 96-well plates (10000 cells/well), which already contain the antiviral compounds. Typically, these plates contain a 5-fold serial dilution of 9 dilution steps of the test compound at 200 times the final concentration in 100% DMSO (500 nL; final concentration range: 25 μM-0.000064 μM or 2.5 μM-0.0000064 μM for the most active compounds). In addition, each plate contains wells which are assigned as virus controls (containing cells and virus in the absence of compound) and cell controls (containing cells in the absence of virus and compound). Once the cells were added in the plates, the plates were incubated in a fully humidified incubator (37° C., 5% $CO_2$) until the next day. Dengue viruses serotype-1, 2, 3 and 4 were diluted in order to obtain a Cp of ~22-24 in the assay. Therefore, 25 μL of virus suspension was added to all the wells containing test compound and to the wells assigned as virus control. In parallel, 25 μL of culture medium was added to the cell controls. Next, the plates were incubated for 3 days in a fully humidified incubator (37° C., 5% $CO_2$). After 3 days, the supernatant was removed from the wells and the cells were washed twice with ice-cold PBS (~100 μL). The cell pellets within the 96-well plates were stored at −80° C. for at least 1 day. Next, RNA was extracted using the Cells-to-CT™ lysis kit, according to the manufacturer's guideline (Life Technologies). The cell lysates can be stored at −80° C. or immediately used in the reverse transcription step.

In preparation of the reverse transcription step, mix A (table 3A) was prepared and 7.57 μL/well was dispensed in a 96-well plate. After addition of 5 μL of the cell lysates, a five minute denaturation step at 75° C. was performed (table 3B). Afterwards, 7.43 μL of mix B was added (table 3C) and the reverse transcription step was initiated (table 3D) to generate cDNA.

Finally, a RT-qPCR mix was prepared, mix C (table 4A), and 22.02 μL/well was dispensed in 96-well LightCycler qPCR plates to which 3 μL of cDNA was added and the qPCR was performed according to the conditions in table 4B on a LightCycler 480.

Using the LightCycler software and an in-house LIMS system, dose response curves for each compound were calculated and the half maximal effective concentration ($EC_{50}$) and the half maximal cytotoxic concentration ($CC_{50}$) were determined (Tables 5-8).

TABLE 3 cDNA synthesis using Mix A, denaturation, Mix B and reverse transcription.

| A | Mix A | | | | | |
|---|---|---|---|---|---|---|
| | Plates | 8 | | | Reaction | |
| | Samples | 828 | | | Vol. (μl) | 20 |
| | | | Concentration | | Volume for (μl) | |
| | Mix Item | Unit | Stock | Final | 1 sample | x samples |
| | Milli-Q $H_2O$ | | | | 7.27 | 6019.56 |
| | R3utr425 | μM | 20 | 0.27 | 0.15 | 124.20 |
| | Ractin876 | μM | 20 | 0.27 | 0.15 | 124.20 |
| | | | Volume mix/well (μl) | | 7.57 | |
| | | | Cell lysates | | 5.00 | |
| B | Denaturation step: | | | | | |
| | Step | | Temp | | Time | |
| | Denaturation | | 75° C. | | 5' | |
| | Hold | | 4° C. | | hold | |
| C | Mix B | | | | | |
| | Samples | 864 | | | | |
| | | | Concentration | | Volume for (μl) | |
| | Mix Item | Unit | Stock | Final | 1 sample | x samples |
| | Expand HIFI buffer 2 | X | 10.00 | 1.00 | 2.00 | 1728.0 |

TABLE 3-continued cDNA synthesis using Mix A, denaturation, Mix B and reverse transcription.

| | | | | | |
|---|---|---|---|---|---|
| $MgCl_2$ | mM | 25.00 | 3.50 | 2.80 | 2419.2 |
| dNTPs | mM | 10.00 | 1.00 | 2.00 | 1728.0 |
| Rnase inhibitor | U/μl | 40.00 | 1.00 | 0.50 | 432.0 |
| Expand RT | U/μl | 50.00 | 0.33 | 0.13 | 112.3 |
| | | Total Volume Mix (μl) | | 7.43 | |

D  Protocol cDNA synthesis

| Step | Temp | Time |
|---|---|---|
| Rev transc | 42° C. | 30' |
| Denaturation | 99° C. | 5' |
| Hold | 4° C. | hold |

TABLE 4 qPCR mix and protocol.

A  Mix C

| Samples | 833 | | Reaction Vol. (μl) | 25 |
|---|---|---|---|---|
| | | Concentration | Volume for (μl) | |
| Mix Item | Unit | Stock | Final | 1 sample | x samples |

| Mix Item | Unit | Stock | Final | 1 sample | x samples |
|---|---|---|---|---|---|
| $H_2O$ PCR grade Roche | | | | 7.74 | 6447.42 |
| Roche 2× MM mix | X | 2 | 1 | 12.50 | 10412.50 |
| F3utr258 | μM | 20 | 0.3 | 0.38 | 316.54 |
| R3utr425 | μM | 20 | 0.3 | 0.38 | 316.54 |
| P3utr343 | μM | 20 | 0.1 | 0.13 | 108.29 |
| Factin743 | μM | 20 | 0.3 | 0.38 | 316.54 |
| Ractin876 | μM | 20 | 0.3 | 0.38 | 316.54 |
| Pactin773 | μM | 20 | 0.1 | 0.13 | 108.29 |
| | | Volume Mix/Tube (μl) | | 22.02 | |
| | | cDNA | | 3.00 | |

B  Protocol qPCR3

| Step | Temp | Time | Ramp rate | |
|---|---|---|---|---|
| preincub/denat | 95° C. | 10 min | 4.4 | |
| Denaturation | 95° C. | 10 sec | 4.4 | 40 cycles |
| annealing | 58° C. | 1 min | 2.2 | |
| Elongation | 72° C. | 1 sec | 4.4 | |
| Cooling | 40° C. | 10 sec | 1.5 | |

TABLE 5

$EC_{50}$, $CC_{50}$, and SI for the compounds against serotype 1 in the RT-qPCR assays

| | Protocol A RT-qPCR serotype 1 TC974#666 | | | | | |
|---|---|---|---|---|---|---|
| compound# | $EC_{50}$ (μM) | N | $CC_{50}$ (μM) | N | SI | N |
| 1B | 0.0044 | 5 | 5.1 | 4 | 1110 | 4 |
| 2B | 0.0024 | 3 | 4.8 | 2 | 2670 | 2 |
| 3A | 0.0036 | 3 | 4.5 | 3 | 1210 | 3 |
| 4A | 0.0039 | 3 | 4.4 | 3 | 1270 | 3 |
| 4B | 0.70 | 3 | >2.5 | 4 | >4.6 | 3 |
| 5A | 0.0026 | 4 | 4.7 | 4 | 1650 | 4 |
| 6B | 0.0031 | 10 | 4.8 | 10 | 1590 | 10 |
| 7B | 0.0051 | 3 | 4.1 | 3 | 802 | 3 |
| 8B | 0.0081 | 3 | >2.5 | 3 | >454 | 3 |
| 9B | 0.0027 | 3 | >2.5 | 3 | >1800 | 3 |
| 10B | 0.0017 | 3 | >2.5 | 3 | >1810 | 3 |
| 11B | 0.0078 | 3 | >2.5 | 3 | >352 | 3 |
| 12A | 0.0033 | 3 | >2.5 | 2 | >934 | 2 |
| 13A | 0.0063 | 3 | >2.5 | 2 | >416 | 2 |

N = the number of independent experiments in which the compounds were tested.

TABLE 6

EC$_{50}$, CC$_{50}$, and SI for the compounds against serotype 2 in the RT-qPCR assays Protocol A
RT-qPCR serotype 2 16681

| compound# | EC$_{50}$ (μM) | N | CC$_{50}$ (μM) | N | SI | N |
|---|---|---|---|---|---|---|
| 1B | 0.0036 | 4 | 3.8 | 4 | 1100 | 4 |
| 2B | 0.0032 | 3 | 5.3 | 2 | 1880 | 2 |
| 3A | 0.0022 | 4 | 9.5 | 4 | 4860 | 4 |
| 4A | 0.0043 | 3 | 3.4 | 3 | 894 | 3 |
| 4B | 1.0 | 3 | 13 | 3 | 17 | 3 |
| 5A | 0.0030 | 3 | 7.6 | 3 | 2680 | 3 |
| 6B | 0.0020 | 11 | 7.9 | 11 | 4400 | 11 |
| 7B | 0.00096 | 4 | 5.0 | 4 | 5780 | 4 |
| 8B | 0.0023 | 4 | 14 | 4 | 5510 | 4 |
| 9B | 0.0012 | 3 | 12 | 3 | 11900 | 3 |
| 10B | 0.0023 | 3 | 10 | 3 | 2670 | 3 |
| 11B | 0.0020 | 3 | 16 | 3 | 4840 | 3 |
| 12A | 0.0044 | 3 | >2.5 | 3 | .794 | 3 |
| 13A | 0.0015 | 3 | >2.5 | 3 | >4280 | 3 |

N = the number of independent experiments in which the compounds were tested.

TABLE 7

EC$_{50}$, CC$_{50}$, and SI for the compounds against serotype 3 in the RT-qPCR assays Protocol A
RT-qPCR serotype 3 H87

| compound# | EC$_{50}$ (μM) | N | CC$_{50}$ (μM) | N | SI | N |
|---|---|---|---|---|---|---|
| 1B | 0.056 | 5 | 2.4 | 4 | 46 | 4 |
| 2B | 0.029 | 3 | 3.6 | 2 | 156 | 2 |
| 3A | 0.029 | 3 | 4.0 | 3 | 169 | 3 |
| 4A | 0.027 | 3 | 3.6 | 3 | 179 | 3 |
| 4B | >1.9 | 3 | 8.6 | 4 | 7.6 | 1 |
| 5A | 0.020 | 3 | 4.3 | 3 | 214 | 3 |
| 6B | 0.028 | 10 | 4.5 | 9 | 253 | 9 |
| 7B | 0.030 | 3 | 3.7 | 2 | 155 | 2 |
| 8B | 0.050 | 3 | >2.5 | 3 | >83 | 3 |
| 9B | 0.016 | 3 | >2.5 | 3 | >191 | 3 |
| 10B | 0.016 | 3 | >2.5 | 3 | >199 | 3 |
| 11B | 0.034 | 3 | >2.5 | 3 | >139 | 3 |
| 12A | 0.040 | 3 | >2.5 | 3 | >67 | 3 |
| 13A | 0.043 | 3 | >2.5 | 3 | >78 | 3 |

N = the number of independent experiments in which the compounds were tested.

TABLE 8

EC50, CC50, and SI for the compounds against serotype 4 in the RT-qPCR assays

Protocol A
RT-qPCR serotype 4 H241

| compound# | EC$_{50}$ (μM) | N | CC$_{50}$ (μM) | N | SI | N |
|---|---|---|---|---|---|---|
| 1B | 0.25 | 4 | 2.9 | 4 | 12 | 4 |
| 2B | 0.17 | 3 | 5.9 | 2 | 33 | 2 |
| 3A | 0.19 | 4 | 6.2 | 3 | 32 | 3 |
| 4A | 0.21 | 3 | 2.2 | 3 | 11 | 3 |
| 4B | >2.5 | 3 | 9.4 | 4 | NA | NA |
| 5A | 0.21 | 3 | 3.8 | 3 | 16 | 3 |
| 6B | 0.14 | 11 | 4.1 | 10 | 27 | 10 |
| 7B | 0.12 | 4 | 3.1 | 3 | 25 | 3 |
| 8B | 0.12 | 4 | 9.0 | 4 | 98 | 4 |
| 9B | 0.11 | 3 | 2.9 | 3 | 23 | 3 |
| 10B | 0.16 | 3 | >2.0 | 3 | >13 | 3 |
| 11B | 0.28 | 3 | 7.6 | 3 | 20 | 3 |
| 12A | 0.24 | 3 | 6.1 | 3 | 24 | 3 |
| 13A | 0.27 | 3 | 2.6 | 3 | >9.4 | 3 |

N = the number of independent experiments in which the compounds were tested.
NA = not approved.

Prior Art Examples

Compounds (56) and (170) disclosed in WO-2013/045516 have been tested in an analogous DENV-2 antiviral assay as the compounds of the present invention and their reported activity is listed below.

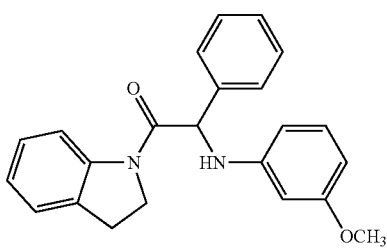 [SMILES: COc1cccc(NC(C(=O)N2CCc3ccccc32)c2ccccc2)c1]

compound (56) of WO-2013/045516

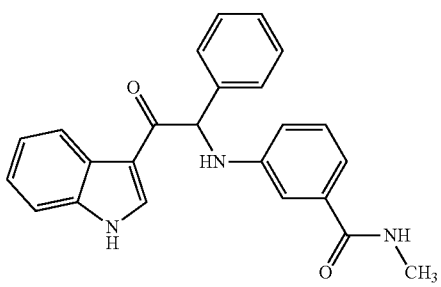 [SMILES: CNC(=O)c1cccc(NC(C(=O)c2c[nH]c3ccccc23)c2ccccc2)c1]

compound (170) of WO-2013/045516

TABLE 9

EC$_{50}$, CC$_{50}$, and SI for compounds (56) and (170) disclosed in the DENV-2 antiviral assay

| compound# | EC$_{50}$ (μM) | CC$_{50}$ (μM) | SI |
|---|---|---|---|
| (56) of WO-2013/045516 | 0.45 | >139 | >312 |
| (170) of WO-2013/045516 | 0.44 | 26 | 58 |

The invention claimed is:
1. A compound having formula (I)
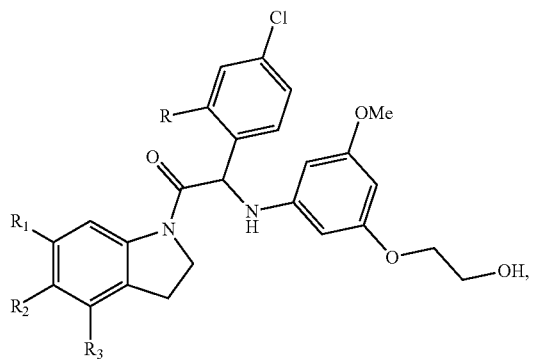
a stereoisomeric form, a pharmaceutically acceptable salt, a solvate or a polymorph thereof, wherein
$R_1$ is $CF_3$ or $OCF_3$;
$R_2$ is H, F or $OCH_3$;
$R_3$ is H or $CH_3$;
and wherein the compound is selected from the group consisting of:
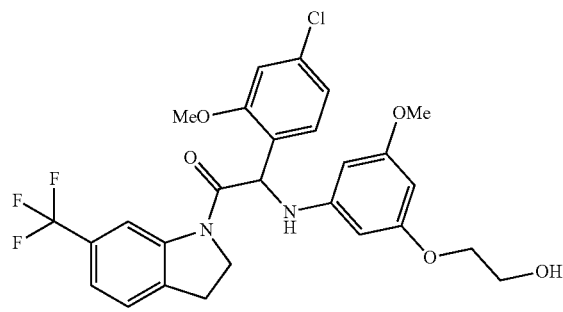
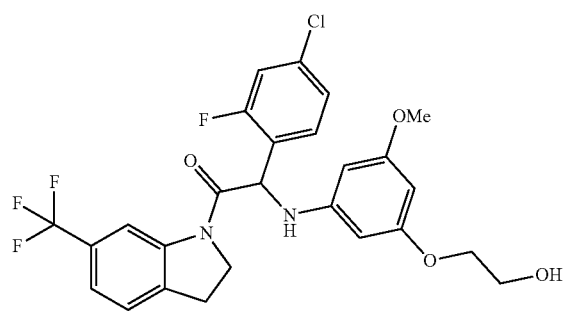
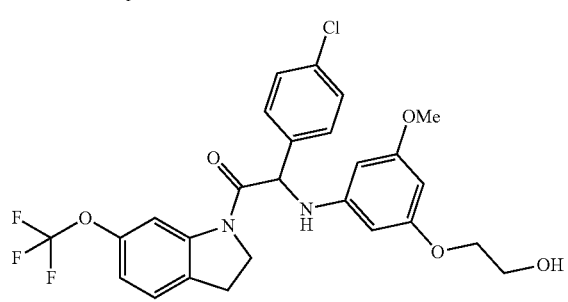
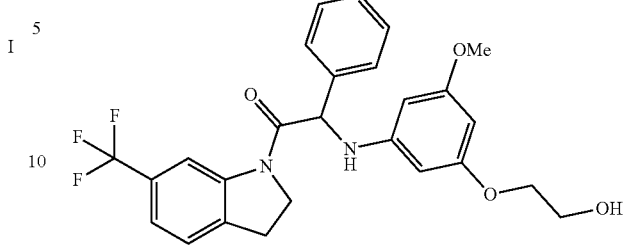
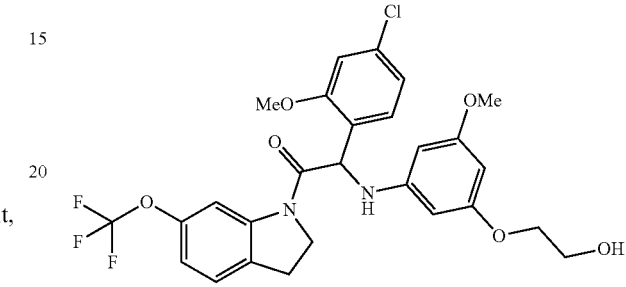
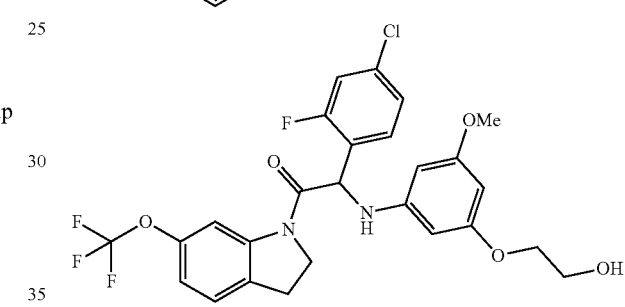
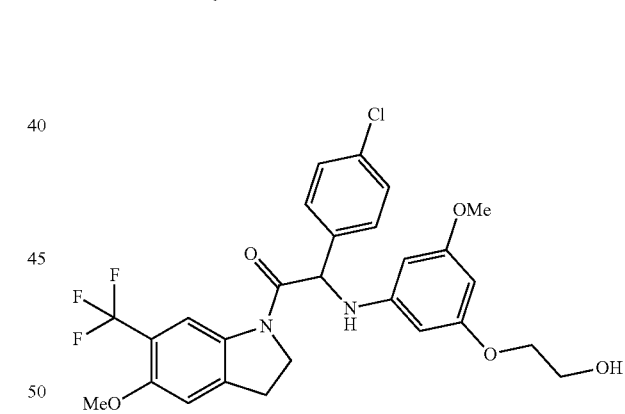
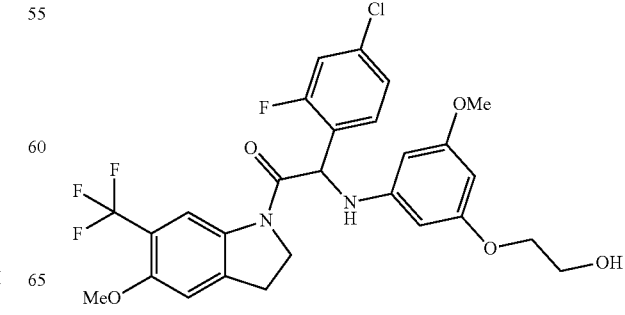

-continued

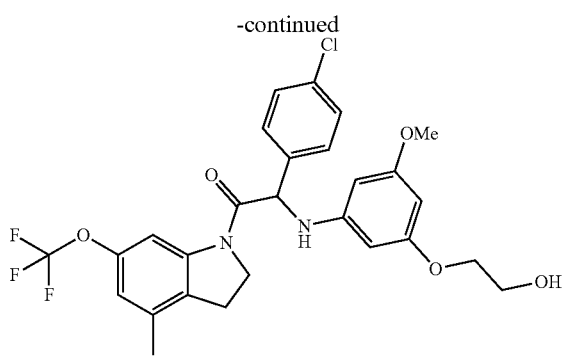

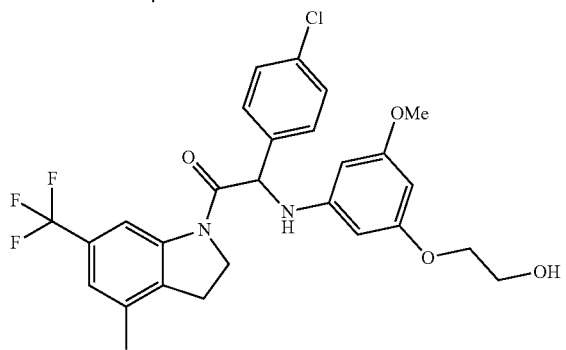

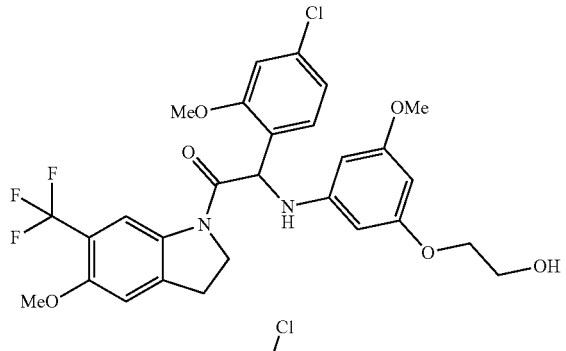

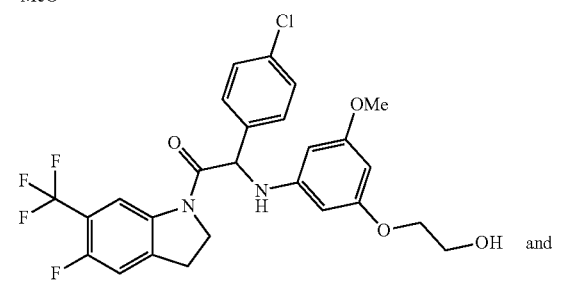

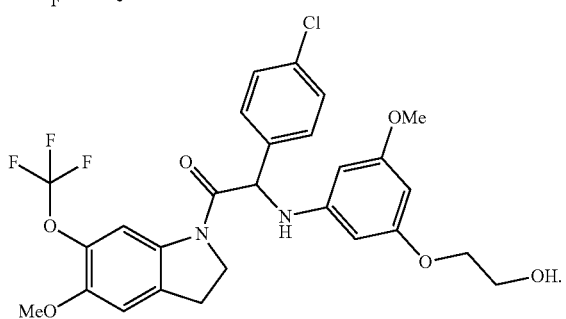

2. A pharmaceutical composition comprising a compound according to claim 1 or its stereoisomeric form, or a pharmaceutically acceptable salt, solvate or polymorph thereof, and one or more pharmaceutically acceptable excipients, diluents or carriers.

3. A method of treating a Dengue viral infection in a subject comprising administering to the subject the compound according to claim 1, or its stereoisomeric form, or a pharmaceutically acceptable salt, solvate or polymorph thereof, or a pharmaceutical composition thereof in an amount effective to treat a Dengue viral infection in a subject.

4. A method of inhibiting replication of a Dengue virus in a biological sample or in a patient comprising contacting the virus with the compound according to claim 1, or a stereoisomeric form, or a pharmaceutically acceptable salt, solvate or polymorph thereof comprising a mono- or di-substituted indole group, in an amount effective to inhibit replication of a Dengue virus in a biological sample or patient.

5. The method according to claim 3 further comprising contacting the Dengue virus with an additional therapeutic agent.

6. The method of claim 5, wherein the additional therapeutic agent is an antiviral agent, a Dengue vaccine, or both.

7. The method according to claim 4 further comprising co-administering an additional therapeutic agent.

8. The method of claim 7, wherein the additional therapeutic agent is an antiviral agent, a Dengue vaccine, or both.

9. The compound as claimed in claim 1 wherein the compound is selected from the group consisting of

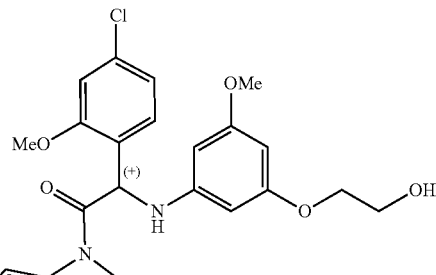

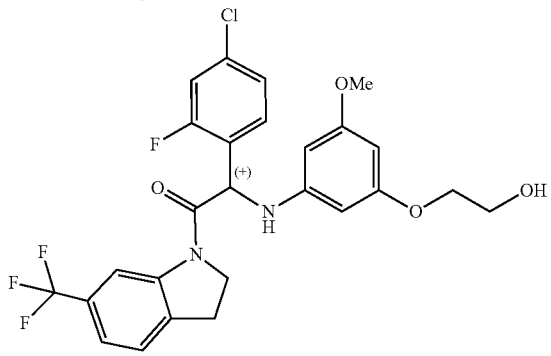

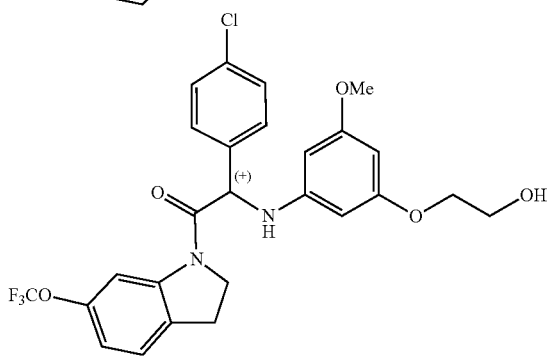

-continued
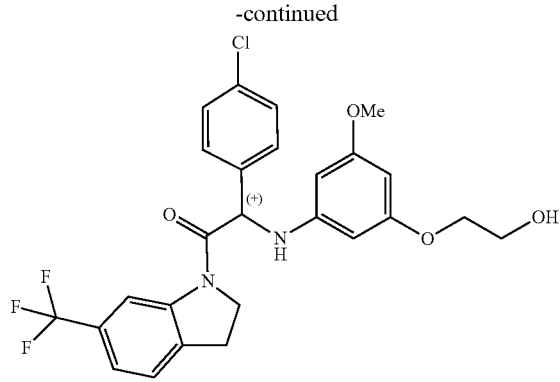
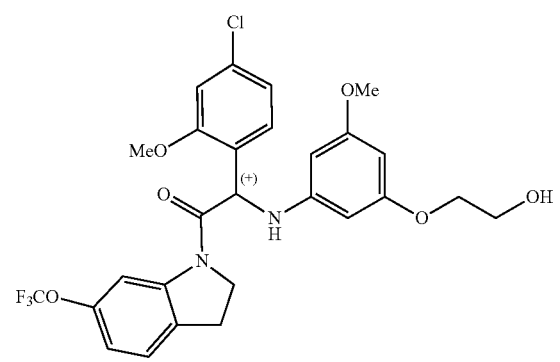
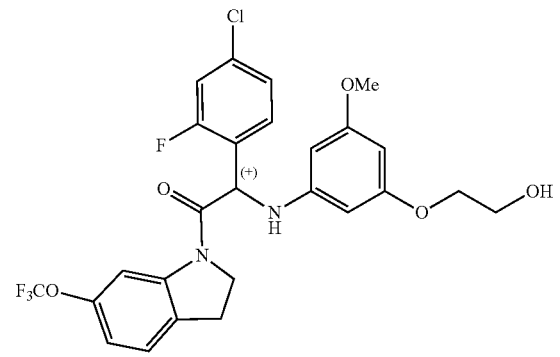
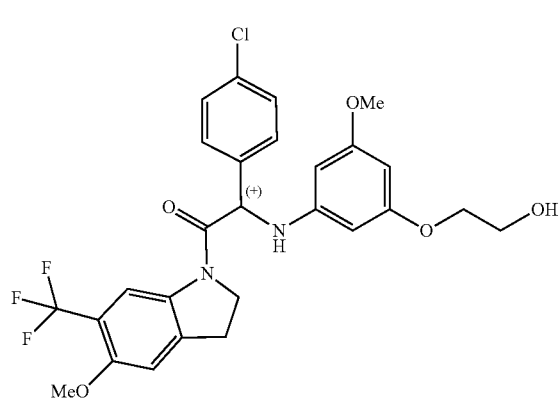
-continued
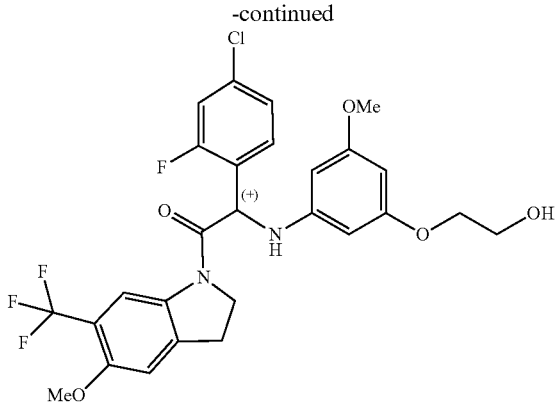
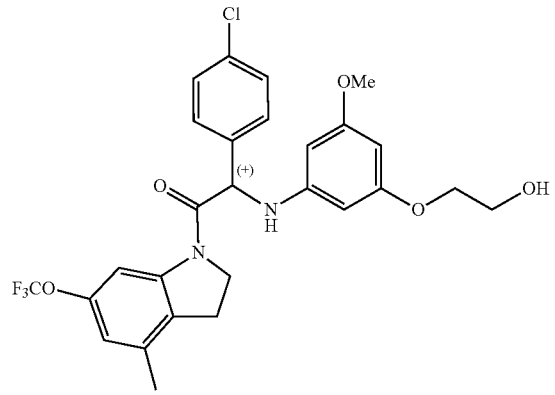
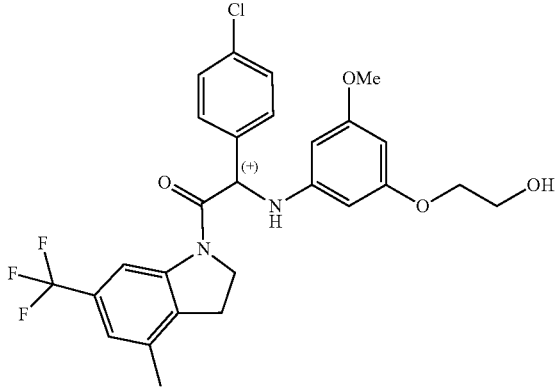
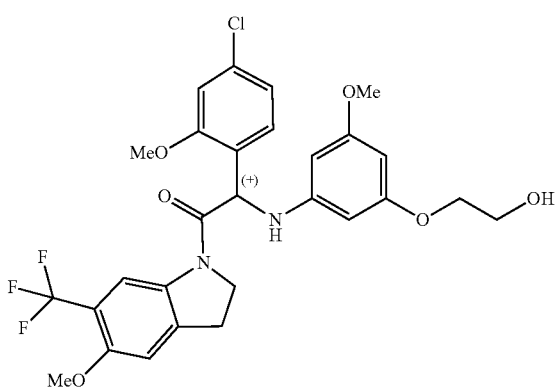

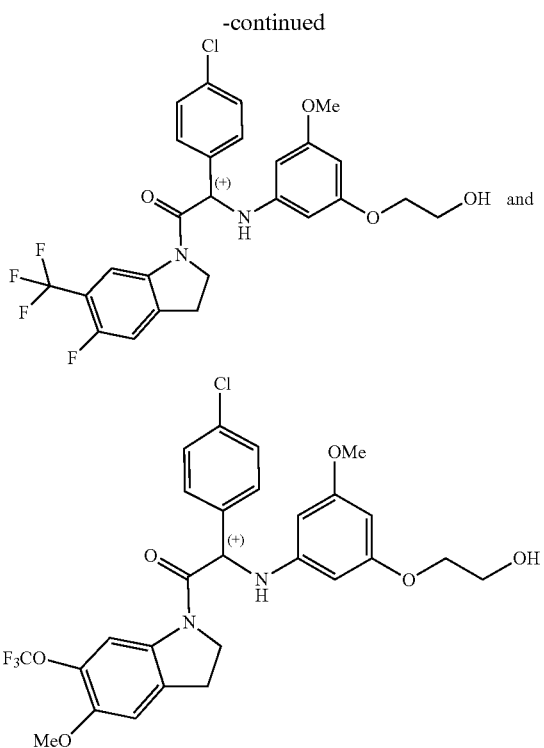

or a pharmaceutically acceptable salt, solvate or polymorph thereof.

10. A pharmaceutical composition comprising a compound according to claim 9, or a pharmaceutically acceptable salt, solvate or polymorph thereof together with one or more pharmaceutically acceptable excipients, diluents or carriers.

11. A method of treating a Dengue viral infection in a subject comprising administering to the subject the compound according to claim 9 or its stereoisomeric form, or a pharmaceutically acceptable salt, solvate or polymorph thereof, or a pharmaceutical composition thereof, in an amount effective to treat a Dengue viral infection in a subject.

12. A method of inhibiting replication of a Dengue virus in a biological sample or in a patient comprising contacting the virus with the compound according to claim 9, or a stereoisomeric form, a pharmaceutically acceptable salt, a solvate or a polymorph thereof comprising a mono- or di-substituted indole group, in an amount effective to inhibit replication of a Dengue virus in a biological sample or patient.

13. The method according to claim 11 further comprising co-administering an additional therapeutic agent.

14. The method of claim 13, wherein the additional therapeutic agent is an antiviral agent, aDengue vaccine, or both.

15. The method according to claim 12 further comprising contacting the Dengue virus with an additional therapeutic agent.

16. The method of claim 15, wherein the additional therapeutic agent is an antiviral agent, a Dengue vaccine, or both.

* * * * *